(12) United States Patent
Kaneko et al.

(10) Patent No.: US 7,335,765 B2
(45) Date of Patent: Feb. 26, 2008

(54) NUCLEOSIDE AND OLIGONUCLEOTIDE ANALOGUES

(75) Inventors: Masakatsu Kaneko, Yokohama (JP); Koji Morita, Tokyo (JP); Takeshi Imanishi, Nara (JP)

(73) Assignees: Daiichi Sankyo Company, Limited, Tokyo (JP); Mitsubishi-Kagaku Foods Corporation, Tokyo (JP)

( * ) Notice: Subject to any disclaimer, the term of this patent is extended or adjusted under 35 U.S.C. 154(b) by 225 days.

(21) Appl. No.: 09/925,673

(22) Filed: Aug. 9, 2001

(65) Prior Publication Data

US 2002/0147332 A1    Oct. 10, 2002

Related U.S. Application Data

(63) Continuation-in-part of application No. PCT/JP00/00725, filed on Feb. 10, 2000.

(30) Foreign Application Priority Data

Feb. 12, 1999   (JP)   ................... 11-033863

(51) Int. Cl.
C07H 19/00 (2006.01)
C07H 21/00 (2006.01)
C07H 19/06 (2006.01)
C70H 19/16 (2006.01)

(52) U.S. Cl. ............... 536/26.1; 536/22.1; 536/23.1; 536/26.2; 536/25.6; 536/27.81; 536/27.21; 536/27.6; 536/28.1

(58) Field of Classification Search ............... 536/26.1, 536/26.2, 23.1, 22.1, 25.6, 27.81, 27.21, 536/27.6, 28.1
See application file for complete search history.

(56) References Cited

U.S. PATENT DOCUMENTS

| | | |
|---|---|---|
| 3,687,808 A | 8/1972 | Merigan, Jr. et al. |
| 4,689,320 A | 8/1987 | Kaji |
| 4,806,463 A | 2/1989 | Goodchild et al. |
| 5,004,810 A | 4/1991 | Draper |
| 5,166,195 A | 11/1992 | Ecker |
| 5,194,428 A | 3/1993 | Agrawai et al. |
| 5,242,906 A | 9/1993 | Pagano et al. |
| 5,248,670 A | 9/1993 | Draper et al. |
| 5,442,049 A | 8/1995 | Anderson et al. |
| 5,457,189 A | 10/1995 | Crooke et al. |
| 5,514,577 A | 5/1996 | Draper et al. |
| 5,514,788 A | 5/1996 | Bennett et al. |
| 5,523,389 A | 6/1996 | Ecker et al. |
| 5,580,767 A | 12/1996 | Cowsert et al. |
| 5,582,972 A | 12/1996 | Lima et al. |
| 5,582,986 A | 12/1996 | Monia et al. |
| 5,591,600 A | 1/1997 | Ecker |
| 5,591,623 A | 1/1997 | Bennett et al. |
| 5,591,720 A | 1/1997 | Anderson et al. |

(Continued)

FOREIGN PATENT DOCUMENTS

EP    1 013 661 A1    6/2000

(Continued)

OTHER PUBLICATIONS

Obika et al., Tetrahedron Letters, vol. 39, pp. 5401-5404, 1998.*
Lawrence D. Kerr et al., "TGF-β1 Inhibition of Transin/Stromelysin Gene Expression Is mediated through a Fos Binding Sequence", *Cell*, vol. 61, pp. 267-278, Apr. 20, 1990.
Muthiah Manoharan et al., "Oligonucleotide Conjugates: Alteration of the Pharmacokinetic Properties of Antisense Agents", *Nucleosides & Nucleotides*, 14 (3-5), pp. 969-973 (1995).
Jack S. Cohen and Michael E. Hogan, "The New Genetic Medicines", *Scientfic American*, pp. 50-55, Dec. (1994).

(Continued)

*Primary Examiner*—Shaojia Anna Jiang
*Assistant Examiner*—Ganapathy Krishnan
(74) *Attorney, Agent, or Firm*—Frishauf, Holtz, Goodman & Chick, P.C.

(57) ABSTRACT

A compound of the formula (1):

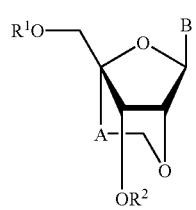

(1)

wherein $R^1$ and $R^2$ are the same or different and represent a hydrogen atom, a hydroxyl protecting group, a phosphate group, or —$P(R^3)R^4$, wherein $R^3$ and $R^4$ are the same or different and represent a hydroxyl group, an amino group, an alkoxy group having from 1 to 4 carbon atoms, a cyanoalkoxy group having from 1 to 5 carbon atoms or an amino group substituted by an alkyl group having from 1 to 4 carbon atoms; A represents an alkylene group having from 1 to 4 carbon atoms and B represents a purin-9-yl group, a 2-oxo-pyrimidin-1-yl group, a substituted purin-9-yl group or a substituted 2-oxo-pyrimidin-1-yl group having a substituent α selected from the group consisting of a hydroxyl group which may be protected, an alkoxy group having from 1 to 4 carbon atoms, a mercapto group which may be protected, an alkylthio group having from 1 to 4 carbon atoms, an alkoxy group having from 1 to 4 carbon atoms, an amino group which may be protected, a mono- or di-alkylamino group which may be substituted by an alkyl group having from 1 to 4 carbon atoms, an alkyl group having from 1 to 4 carbon atoms and a halogen atom; or a salt thereof.

60 Claims, No Drawings

U.S. PATENT DOCUMENTS

| | | | |
|---|---|---|---|
| 5,607,923 A | 3/1997 | Cook et al. | |
| 5,620,963 A | 4/1997 | Cook et al. | |
| 5,658,891 A | 8/1997 | Draper et al. | |
| 5,661,134 A | 8/1997 | Cook et al. | |
| 5,681,747 A | 10/1997 | Boggs et al. | |
| 5,681,944 A | 10/1997 | Crooke et al. | |
| 5,691,461 A | 11/1997 | Ecker et al. | |
| 5,877,309 A | 3/1999 | McKay et al. | |
| 5,955,443 A | 9/1999 | Bennett et al. | |
| 5,985,558 A | 11/1999 | Dean et al. | |
| 6,111,094 A | 8/2000 | Bennett et al. | |
| 6,127,533 A | 10/2000 | Cook et al. | |
| 6,268,490 B1 | 7/2001 | Imanishi et al. | |
| 6,670,461 B1 | 12/2003 | Wengel et al. | |
| 6,794,499 B2 * | 9/2004 | Wengel et al. | 536/23.1 |
| 7,034,133 B2 | 4/2006 | Wengel et al. | |
| 2002/0068708 A1 | 6/2002 | Wengel et al. | |
| 2003/0082807 A1 | 5/2003 | Wengel | |
| 2003/0087230 A1 | 5/2003 | Wengel | |
| 2003/0134808 A1 | 7/2003 | Wengel et al. | |
| 2003/0144231 A1 | 7/2003 | Wengel et al. | |
| 2004/0143114 A1 | 7/2004 | Imanishi et al. | |

FOREIGN PATENT DOCUMENTS

| | | | |
|---|---|---|---|
| WO | WO 94/08003 A | | 4/1994 |
| WO | WO 96/31557 A | | 10/1996 |
| WO | 98/39352 | * | 9/1998 |
| WO | WO 98/39352 A | | 9/1998 |
| WO | WO 99/14226 | | 3/1999 |
| WO | WO 99/14226 A | | 3/1999 |
| WO | WO 01/18015 A1 | | 3/2001 |

OTHER PUBLICATIONS

Genevieve Pratviel et al., "Furfural as a Marker of DNA Cleavage by Hydroxylation at the 5' Carbon of Deoxyribose", *Angewandte Chemie*, 30, No. 6, pp. 702-705 (1991).

Griffiths et al, "Keratinocyte Intercellular Adhesion Molecule-1 (ICAM-1) Expression Precedes Dermal T Lymphomatic Infiltration . . . ", *American Journal of Path.*, Dec. 1989, vol. 135, No. 6, pp. 1045-1053.

Thuong et al, "Sequence-Specific Recognition and Modification of Double-Helical DNA by Oligonucleotides", *Angew. Chem. Int. Ed. Engl.*, 1993, 32, pp. 666-690.

Manoharan et al, "Chemical Modifications to Improve Uptake and Bioavailability of Antisense Oligonucleotides", *Ann. N.Y. Acad. of Sciences*, 1992, 660, pp. 306-309.

Stetler-Stevenson et al, "Tumor Cell Interactions With the Extracellular Matrix During Invasion and Metastasis", *Annu. Rev. Cell Biol.*, 1993, 9, pp. 541-573.

Cook, "Medicinal chemistry of antisense oligonucleotides—future opportunities", *Anti-Canceer Drug Design*, 1991, 6, pp. 585-607.

Sanghvi, "Heterocyclic Base Modifications in Nucleic Acids and Their Applications in Antisense Oligonucleotides", *Antisense Research and Applications*, 1993, Chapter 15, pp. 273-288.

Shiohara et al, "Fixed Drug Eruption", *Arch Dermatol.*, Oct. 1989, vol. 125, pp. 1371-1376.

Mishra et al, "Improved leishmanicidal effect of phosphorotioate antisense oligonucleotides by LDL-mediated delivery", *Biochim. Biophys. Acta*, 1995, 1264, pp. 229-237.

Svinarchuk et al, Inhibition of HIV proliferation in MT-4 cells by antisense oligonucleotide conjugated to lipophilic groups, *Biochimie*, 1993, 75, pp. 49-54.

Manoharan et al, "Introduction of a Lipophilic Thioether Tether in the Minor Groove of Nucleic Acids for Antisense Applications", *Bioorg. Med. Chem. Lett.*, 1993, vol. 3, No. 12, pp. 2765-2770.

Manoharan et al, "Cholic Acid-Oligonucleotide Conjugates for Antisense Applications", *Bioorg. Med. Chem. Lett.*, 1994, vol. 4, No. 8, pp. 1053-1060.

Lisby et al, "Intercellular adhesion molecule-I (ICAM-I) expression correlated to inflammation", *Br. J. of Dermatol.*, 1989, 120, 479-484.

Maher III, "Prospects for the Therapeutic Use of Antigene Oligonucleotides", Cancer Investigation, *Cancer Investigation*, 1996, 14(1), pp. 66-82.

Birkedal-Hansen, "Proteolytic remodeling of extracellular matrix", *Current Op. Biol.*, 1995, 7, pp. 728-735.

LeRoith et al, "Molecular and Cellular Aspects of the Insulin-Like Growth Factor I Receptor", *Endocr. Rev.*, 1995, vol. 16, No. 2, pp. 143-163.

Kabanov et al, "A new class of antivirals: antisense oligonucleotides combined with a hydrophobic substituent . . . ", *FEBS Lett.*, Jan. 1990, vol. 259, No. 2, pp. 327-330.

DeLisser et al, "Molecular and functional aspects of PECAM-1/CD31" *Immunol. Today*, 1994, vol. 15, No. 10, pp. 490-495.

Himelstein et al, "Metalloproteinases in Tumor Progression: The Contribution of MMP-9", *Invasion Metastasis*, 1994-95, 14, pp. 246-258.

Ho et al, "Treatment of severe lichen planus with cyclosporine", *J. Am. Acad. Dermatol.*, 1990, vol. 22, No. 1, pp. 64-68.

Gum et al, "Stimulation of 92-kDa Gelatinase B Promoter Activity by ras Is Mitrogen-activated Protein Kinase . . . ", *J. Biol. Chem.*, 1996, vol. 271, No. 18, pp. 10672-10680.

Litwin et al, Novel Cytokine-independent Induction of Endothelial Adhesion Molecules Regulated by Platelet/Endothelial Cell Adhesion Molecule (CD31), *J. Cell Biol.*, 1997, vol. 139, No. 1, pp. 219-228.

Newman, "Perspective Series: Cell Adhesion in Vascular Biology", *J. Clin. Invest.*, 1997, vol. 99, No. 1, pp. 3-8.

Hakugawa et al, "The Inhibitory Effect of Anti-Adhesion Molecule Antibodies on Eosinophil . . . ", *J. Dermatol.*, 1997, vol. 24, pp. 73-79.

Demers et al, "Enhanced PCR amplification of VNTR locus D1S80 using peptide nucleic acid (PNA)", *Nucl. Acid Res.*, 1995, vol. 23, No. 15, pp. 3050-3055.

Shea et al, "Synthesis, Hybridization properties and antiviral activity of lipid-oligodeoxynucleotide conjugates", *Nucl. Acid Res.*, 1990, vol. 18, No. 13, pp. 3777-3783.

Oberhauser et al, "Effective incorporation of 2' O-methyl-oligoribonucleotides into lipsomes and enhanced cell association . . . ", *Nucl. Acid Res.*, 1992, vol. 20, No. 3, pp. 533-538.

Regezi et al, "Vascular adhesion molecules in oral lichen planus", *Oral Surg. Oral Med. Oral Pathol. Oral Radiol. Endod.*, 1996, vol. 81, No. 6, pp. 682-690.

Bernhard et al, "Direct evidence linking expression of matrix metalloproteinase 9 (92-kDa gelatinase/collagenase) . . . ", *Proc. Natl. Acad. Sci. USA*, 1994, vol. 91, pp. 4293-4297.

Dean et al, "Inhibition of protein kinase C-α expression in mice after systemic administration . . . ", *Prac. Natl. Acad. Sci. USA*, 1994, vol. 91, pp. 11762-11766.

Letsinger et al, "Cholesteryl-conjugated oligonucleotides: Synthesis, properties and activity . . . ", *Prac. Natl. Acad. Sci. USA*, 1989, vol. 86, pp. 6553-6556.

Rubin et al, "Biology of Disease—Insulin-Like Growth Factor-I Receptor", *R. Lab. Invest.*, 1995, vol. 73, No. 3, pp. 311-331.

Erwin, "The Mother of Mass Extinctions", *Sci. Amer.*, 1996, 275, pp. 72-78.

Crawford, "The Mixed Blessing of Inexpensive Oil", *Science*, 1988, vol. 242, pp. 1242-1243.

Wahlestedt et al, "Modulation of anxiety and Neuropeptide Y-Y1 Receptors by Antisense Oligodeoxynucleotides", *Science*, 1993, vol. 259, pp. 528-531.

Koshkin et al, "LNA (Locked Nucleic Acids) : Synthesis of the Adenine, Cytosine, Guanine, 5-Methylcytosine . . . " *Tetrahedron*, 1998, 54, pp. 3607-3630.

Kroschwitz, Editor, *Concise Encyclopedia of Polymer Science and Engineering*, 1990, pp. 858-859.

Berkow et al, Editors, *The Merck Manual of Diagnosis and Therapy*, 1987, 15th Edition, pp. 2263-2277.

Morassutti et al, "Reduction of *mdr1* Gene Amplification in Human Multidrug-Resistant LoV1 DX Cell Line . . . ", *Antisense & Nucleic Acid Drug Dev.*, 1999, 9, pp. 261-270.

Ebbinghaus et al, "Inhibition of Transcription Elongation in the HER-2/neu Coding Sequence . . . ", *Biochemistry*, 1999, 38, pp. 619-628.

Catapano et al, "Inhibition of Gene Expression anc Cell Proliferation of Triple Helix-Forming Oligonucleotides . . . ", *Biochemistry*, 2000, 39, pp. 5126-5138.

Yu et al, Specific Inhibition of PCR by Non-Extendable Oligonucleotides Using a 5' to 3' Exonuclease-Deficient DNA Polyerase, *Biotechniques*, 1997, vol. 23, No. 4, pp. 714-720.

Resnicoff et al, "Inhibition of rat C6 glioblastoma tumor growth by expression of insulin-like growth factor I receptor antisense mRNA", *Cancer Immunol. Immunother.*, 1996, 42, pp. 64-68.

Resnicoff et al, "Rat Glioblastoma Cells Expressing an Antisense RNA to the Insulin-like Growth . . . ", *Cancer Research*, 1994, 54, pp. 2218-2222.

Pass et al, "Inhibition of Hamster Mesothelioma Tumorigenesis by an Antisense Expression Plasmid to the Insulin-like Growth Factor-1 Receptor", *Cancer Research*, 1996, 56, pp. 4044-4048.

Hua et al, "Inhibition of Matrix Metalloproteinase 9 Expression by a Ribozyme Blocks Metastasis in a Rat Sarcoma Model System", *Cancer Research*, 1996, 56, pp. 5279-5284.

Singh et al, "LNA (locked nucleic acids) : synthesis and high-affinity nucleic acid recognition", *Chem. Communication*, 1998, 4, pp. 455-456.

Hurtenbach et al, "Prednisolone Reduces Experimental Arthritis and Inflammatory Tissue Destruction in Scid Mice Infected with *Borrelia burgdorferi*", *Int. J. Immunopharmac.*, 1996, vol. 18, No. 5, pp. 281-288.

Crooke et al, "Pharmacokinetic Properties of Several Novel Oligonucleotide Analogs in mice", *J. Pharmacol. & Exp. Ther.*, 1996, vol. 277, No. 2, pp. 923-937.

Wahlestedt et al, "Antisense oligodeoxynucleotides to NMDA-R1 receptor channel protect cortical neurons . . . " *Nature*, 1993, vol. 363, pp. 260-263.

Porreca et al, "A comparison of the potential role of the tetrodotoxin-insensitive sodium channels, . . . " *Proc. Natl. Acad. Sci. USA*, 1999, vol. 96, pp. 7640-7644.

Rininsland et al, "Suppression of insulin-like growth factor type I receptor by a triple-helix strategy . . . ", *Proc. Natl. Acad. Sci. USA*, 1997, vol. 94, pp. 5854-5859.

Giovannangeli et al, "Triple-helix formation by oligonucleotides containing the three bases thymine, cystosine, and guanine", *Proc. Natl. Acad. Sci. USA*, 1992, vol. 89, pp. 8631-8635.

Iyer et al, "A Novel Nucleoside Phosphoramidite Synthon Derived from 1R, 2s-Ephedrine", *Tetrahedron Asymmetry*, 1995, vol. 6, No. 5, pp. 1051-1054.

Manoharan et al, "Lipidic Nucleic Acids", *Tetrahedron Letters*, 1995, vol. 36, No. 21, pp. 3651-3654.

Obika et al, "Stability and structural features of the duplexes containing nucleoside analogues . . . ", *Tetrahedron Letters*, 1998, vol. 39, pp. 5401-5404.

Albert et al, "Antisense knockouts: molecular scalpels for the dissection of signal transduction", *Trends in Pharmacol. Sci.*, 1994, vol. 15, pp. 250-254.

U.S. Appl. No. 10/054,300, Imanishi et al.

Girotra, Narindar N., et al., "Novel Transformations of Zaragozic Acid A Derivatives with Cesium Fluoride", *Tetrahedron Letters*, 40(13), (1999), pp. 2485-2488.

Procopiou, Panayiotis A., et al., "The Squalestatins: Cleavage of the Bicyclic Core Via the Novel 6,8-Dioxabicyclo[3.2.1] Octane Ring System", *Journal of the Chemical Society*, Perkin Trans. 1: Organic and Bio-Organic Chemistry, (11), (1995), pp. 1341-1347.

Chan, Chuen, et al., "The Squalestatins: C-3 Decarboxylation Studies and Rearrangement to the 6,8-Dioxabicyclo [3.2.1] Octane Ring System", *Tetrahedron Letters*, 34 (38), (1993), pp. 6143-6146.

Obika S., et al., "Synthesis of 2'-O,4'-C-Methyleneuridine and -cytidine. Novel Bicyclic Nucleosides Having a Fixed $C_3$, -endo Sugar Puckering", *Tetrahedron Letters*, (1997), 38(50), 8735-8738.

Nielsen P, et al., "Synthesis of 2'-O,3'-C-Linked Bicyclic Nucleosides and Bicyclic Oligonucleotides", *J. Chem. Soc., Perkin Trans. 1*, (1997) 3423-3433.

Singh S.K., et al., "LNA (Locked Nucleic Acids): Synthesis and High-Affinity Nucleic Acid Recognition", *Chem. Commun.*, (1998), 455-456.

Koshkin A.A., et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition", *Tetrahedron*, (1998), 54, 3607-3630.

Singh S.K. et al., "University of LNA-Mediated High-Affinity Nucleic Acid Recognition", *Chem. Commun.*, (1998), 1247-1248.

Christensen N.K. et al., "A Novel Class of Oligonucleotide Analogues Containing 2'-O,3'-C-Linked [3.2.0] Bicycloarabinonucleoside Monomers: Synthesis, Thermal Affinity Studies, and Molecular Modeling", *J. Am. Chem. Soc.*, (1998), 120, 5458-5463.

Koshkin A.A., et al., "Synthesis of Novel 2',3'-Linked Bicyclic Thymine Ribonucleosides", *J. Org. Chem.*, (1998), 63, 2778-2781.

Ezzitouni A., et al., "Conformationally Locked Carbocyclic Nucleosides Built on a Bicyclo [3.1.0] Hexane Template with a Fixed Southern Conformation. Synthesis and Antiviral Activity", *J. Chem. Soc., Perkins Trans. 1*, (1997), 1073-1078.

Freier S.M., et al., "The Ups and Downs of Nucleic Acid Duplex Stability: Structure-Stability Studies on Chemically-Modified DNA:RNA Duplexes", *Nucleic Acids Research*, (1997), 25(22), 4229-4443.

Koshkin A.A., et al., "Novel Covenient Syntheses of LNA [2.2.1]Bicyclo Nucleosides", *Tetrahedron Letters*, (1998), 39, 4381-4384.

Wengel, "LNA (Locked Nucleic Acids): Synthesis and High-Affinity Nucleic Acid Recognition—Stop the Twisting!", National Seminar on Perspectives in Interfacial Areas of Chemistry and Biology, Delhi University, Jan. 20-22, 1998.

Imanishi, T., "Synthesis and Property of Novel Conformationally Constrained Nucleoside and Oligonucleotide Analogs", The Sixteenth International Congress of Heterocyclic Chemistry, Aug. 10-15, 1997.

Satoshi Obika et al., "Preparation and Properties of 2',5'-Linked Oligonucleotide Analogues Containing 3'-O,4'-C-Methyleneribonucleosides", *Bioorganic & Medicinal Chemistry Letters*, 9 (1999), 515-518.

S. Obika, D. Nanbu, K. Morio and T. Imanishi, "Synthesis and Properties of Oligonucleotides Containing Novel Bicyclic Nucleosides with a Fixed N-Form Sugar Puckering", Summary of Poster No. 32 of the 7th Symposium on Antisense, Nov. 21, 1997, Chiba City, Japan.

S. Obika, K. Morio, D. Nanbu and T. Imanishi, "Duplex and Triplex Formation of 2', 5'-Linked Oligonucleotide Analogs Having Restricted Sugar Puckering in S-Conformation", Summary of Poster No. 33 of the 7th Symposium on Antisense, Nov. 21, 1997, Chiba City, Japan.

Martin, "A New Access to 2'-O-Alkylated Ribonucleosides and Properties of 2'-O-Alkylated Oligoribonucleotides", *Helv. Chim. Acta.*, 1995, vol. 78, pp. 486-504.

Hegemann et al., "Biochemical Pharmacology of Protein Kinase C and its Relevance for Dermatology", *Pharmacol. of the Skin*, 1992, Chapter 22, pp. 357-368.

S. Obika, K. Morio, Y. Hari and T. Imanishi, "Facile Synthesis and Conformation of 3'-O,4'-C-Methyleneribonucleosides," *Chem. Commun.*, 2423-2424 (1999).

S. Obika, D. Nanbu, K. Morio and T. Imanishi, "Synthesis and Properties of Oligonucleotides Containing Novel Bicyclic Nucleosides with a Fixed N-Form Sugar Puckering," Poster No. 32 of the 7th Symposium on Antisense, Nov. 21, 1997, Chiba City, Japan.

U.S. Appl. No. 11/604,630, filed Nov. 27, 2006, Group Art Unit 1635, Confirmation No. 3790.

Makoto Koizumi et al., "Triplex formation with 2'-O,4'-C-ethylene-bridged nucleic acids (ENA) having C3'-endo conformation at physiological pH," *Nucleic Acids Research*, vol. 31, No. 12 (2003), pp. 3267-3273.

Koiji Morita et al., "Synthesis and Properties of 2'-O,4'-C-Ethylene-Bridged Nucleic Acids (ENA) as Effective Antisense Oligonucleotides," *Bioorganic & Medicinal Chemistry*, 11, (2003), pp. 2211-2226.

Satoshi Obika et al., "2'-O,4'-C-Methylene Bridged Nucleic Acid (2',4'-BNA); Synthesis and Triplex-Forming Properties," *Bioorganic & Medicinal Chemistry*, 9, (2001), pp. 1001-1011.

\* cited by examiner

NUCLEOSIDE AND OLIGONUCLEOTIDE ANALOGUES

This application is a continuation-in-part application of international application PCT/JP00/00725 filed Feb. 10, 2000 (not published in English), the entire contents of which are hereby incorporated by reference herein.

BACKGROUND OF THE INVENTION

1. Field of the Invention

The present invention relates to novel oligonucleotide analogues, which exhibit antisense or antigene activity having excellent stability, or exhibit excellent activity as a detection agent (probe) for a specific gene or as a primer for starting amplification, and to novel nucleoside analogues which are intermediates for their production.

2. Background Information

Oligonucleotide analogues, which have excellent antisense or antigene activity and which are stable in the body are expected to be useful pharmaceuticals. In addition, oligonucleotide analogues having a high degree of stable complementary chain formation ability with DNA or mRNA are useful as detection agents for a specific gene or as primers for starting amplification.

In contrast, naturally-occurring oligonucleotides are known to be quickly decomposed by various nucleases present in the blood and cells. In some cases, naturally-occurring oligonucleotides may not have sufficient sensitivity for use as detection agents for specific genes or as primers for starting amplification due to limitations on their affinity with complementary base sequences.

In order to overcome these shortcomings, various non-naturally-occurring oligonucleotide analogues have been produced, and have been attempted to be developed for use as pharmaceuticals or detection agents for specific genes. Namely, known examples of such non-naturally-occurring oligonucleotide analogues include those in which an oxygen atom attached to a phosphorus atom in a phosphodiester bond of an oligonucleotide is replaced with a sulfur atom, those in which said oxygen atom is replaced with a methyl group, those in which said oxygen atom is replaced with a boron atom, and those in which a sugar moiety or base moiety of an oligonucleotide is chemically modified. For example, ISIS Corp. has developed thioate-type oligonucleotide ISIS2922 (Vitravene) as a therapeutic agent for human cytomegalovirus retinitis and ISIS2922 has been put on the open market in the United States.

However, in consideration of the potency of the antisense or antigene activity in the above non-naturally-occurring oligonucleotide analogues, namely the ability to form a stable complementary chain with DNA or mRNA, stability with respect to various nucleases, and the manifestation of adverse side effects due to non-specific bonding with various proteins in the body, there has been a need for a non-naturally-occurring oligonucleotide analogue having even better stability in the body, a low incidence of adverse side effects and a high ability to form complementary chains.

SUMMARY OF THE INVENTION

The inventors of the present invention conducted intensive research over a long period of time on non-naturally-occurring oligonucleotide analogues having excellent antisense or antigene activity, excellent stability in the body and a low incidence of adverse side effects. As a result of that research, they found that oligonucleotide analogues or nucleoside analogues having an ether bond in said molecules are useful as an antisense or antigene pharmaceutical having excellent stability, a detection agent (probe) for a specific gene, a primer for starting amplification or as intermediates for their production, and accomplished the present invention.

In the following, the present invention will be described in detail.

The novel nucleoside analogues of the present invention are compounds of the formula (1):

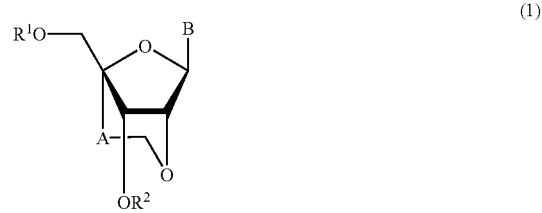

wherein $R^1$ and $R^2$ are the same or different and represent a hydrogen atom, a hydroxyl protecting group, a phosphate group, a protected phosphate group or —P($R^3$)$R^4$ wherein $R^3$ and $R^4$ are the same or different and represent a hydroxyl group, a protected hydroxyl group, a mercapto group, a protected mercapto group, an amino group, an alkoxy group having from 1 to 4 carbon atoms, an alkylthio group having from 1 to 4 carbon atoms, a cyanoalkoxy group having from 1 to 5 carbon atoms or an amino group substituted by an alkyl group having from 1 to 4 carbon atoms;

A represents an alkylene group having from 1 to 4 carbon atoms; and

B represents an unsubstituted purin-9-yl group, an unsubstituted 2-oxo-pyrimidin-1-yl group or a substituted purin-9-yl group or a substituted 2-oxo-pyrimidin-1-yl group having a substituent selected from the a group defined hereinbelow;

or salts thereof.

The oligonucleotide analogues of the present invention are oligonucleotide analogues having two or more nucleoside units, wherein at least one of the nucleoside units is a structure of the formula (2):

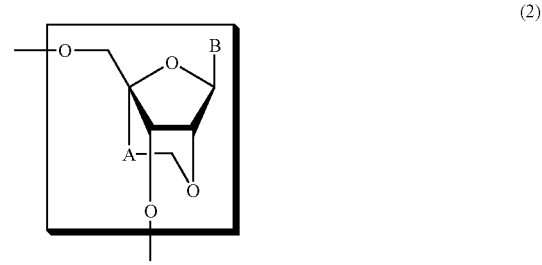

wherein A represents an alkylene group having from 1 to 4 carbon atoms; and B represents an unsubstituted purin-9-yl group, an unsubstituted 2-oxo-pyrimidin-1-yl group or a substituted purin-9-yl group or a substituted 2-oxo-pyrimidin-1-yl group having a substituent selected from the following α group;

α group:
an unprotected hydroxyl group,
a protected hydroxyl group,
an alkoxy group having from 1 to 4 carbon atoms,
an unprotected mercapto group,
a protected mercapto group,
an alkylthio group having from 1 to 4 carbon atoms,
an unprotected amino group,
a protected amino group,
an amino group substituted by an alkyl group having from 1 to 4 carbon atoms,
an alkyl group having from 1 to 4 carbon atoms, and
a halogen atom;

or a salt thereof.

DETAILED DESCRIPTION OF THE INVENTION

"The alkylene group having from 1 to 4 carbon atoms" of A in the above formula (1) or (2) may include methylene, ethylene, trimethylene and tetramethylene groups, preferably a methylene group.

The protecting group of "the hydroxyl protecting group" of $R^1$ and $R^2$ and "the protected hydroxyl group" of $R^3$ and $R^4$ or the α group in the above formula (1) or (2) refers to a protecting group which can be cleaved by a chemical method such as hydrogenolysis, decomposition, hydrolysis, electrolysis and photolysis or a biological method such as hydrolysis in the human body, and such protecting groups may include "an aliphatic acyl group" such as an alkylcarbonyl group, e.g., formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl and heneicosanoyl, a carboxylated alkylcarbonyl group, e.g., succinoyl, glutaroyl and adipoyl, a halogeno lower alkylcarbonyl group, e.g., chloroacetyl, dichloroacetyl, trichloroacetyl and trifluoroacetyl, a lower alkoxy lower alkylcarbonyl group, e.g., methoxyacetyl, and an unsaturated alkylcarbonyl group, e.g., (E)-2-methyl-2-butenoyl;

"an aromatic acyl group" such as an arylcarbonyl group, e.g., benzoyl, α-naphthoyl and β-naphthoyl, a halogenoarylcarbonyl group, e.g., 2-bromobenzoyl and 4-chloro-benzoyl, a lower alkylated arylcarbonyl group, e.g., 2,4,6-trimethylbenzoyl and 4-toluoyl, a lower alkoxylated arylcarbonyl group, e.g., 4-anisoyl, a carboxylated arylcarbonyl group, e.g., 2-carboxybenzoyl, 3-carboxybenzoyl and 4-carboxybenzoyl, a nitrated arylcarbonyl group, e.g., 4-nitrobenzoyl and 2-nitrobenzoyl, a lower alkoxy carbonylated arylcarbonyl group, e.g., 2-(methoxycarbonyl)benzoyl and an arylated arylcarbonyl group, e.g., 4-phenylbenzoyl;

"a tetrahydropyranyl group or a tetrahydrothiopyranyl group" such as tetrahydropyran-2-yl, 3-bromotetrahydropyran-2-yl, 4-methoxytetrahydropyran-4-yl, tetrahydrothiopyran-2-yl and 4-methoxytetrahydrothiopyran-4-yl;

"a tetrahydrofuranyl group or a tetrahydrothiofuranyl group" such as tetrahydrofuran-2-yl and tetrahydrothiofuran-2-yl;

"a silyl group" such as a tri-lower alkylsilyl group, e.g., trimethylsilyl, triethylsilyl, isopropyldimethylsilyl, t-butyldimethylsilyl, methyldiisopropylsilyl, methyldi-t-butylsilyl and triisopropylsilyl and a tri-lower alkylsilyl group substituted by one or two aryl groups, e.g., diphenylmethylsilyl, diphenylbutylsilyl, diphenylisopropylsilyl and phenyldiisopropylsilyl;

"a lower alkoxymethyl group" such as methoxymethyl, 1,1-dimethyl-1-methoxy-methyl, ethoxymethyl, propoxymethyl, isopropoxymethyl, butoxymethyl and t-butoxymethyl;

"a lower alkoxylated lower alkoxymethyl group" such as 2-methoxyethoxymethyl;

"a halogeno lower alkoxymethyl group" such as 2,2,2-trichloroethoxymethyl and bis(2-chloroethoxy)methyl;

"a lower alkoxylated ethyl group" such as 1-ethoxyethyl and 1-(isopropoxy)ethyl;

"a halogenated ethyl group" such as 2,2,2-trichloroethyl;

"a methyl group substituted by from 1 to 3 aryl groups" such as benzyl, α-naphthyl-methyl, β-naphthylmethyl, diphenylmethyl, triphenylmethyl, α-naphthyldiphenyl-methyl and 9-anthrylmethyl;

"a methyl group substituted by from 1 to 3 aryl groups wherein said aryl ring is substituted by a lower alkyl, lower alkoxy, halogen or cyano group" such as 4-methylbenzyl, 2,4,6-trimethylbenzyl, 3,4,5-trimethylbenzyl, 4-methoxybenzyl, 4-methoxy-phenyldiphenylmethyl, 4,4'-dimethoxytriphenylmethyl, 2-nitrobenzyl, 4-nitrobenzyl, 4-chlorobenzyl, 4-bromobenzyl and 4-cyanobenzyl;

"a lower alkoxycarbonyl group" such as methoxycarbonyl, ethoxycarbonyl, t-butoxycarbonyl and isobutoxycarbonyl;

"a lower alkoxycarbonyl group substituted by halogen or a tri-lower alkylsilyl group" such as 2,2,2-trichloroethoxycarbonyl and 2-trimethylsilylethoxycarbonyl;

"an alkenyloxycarbonyl group" such as vinyloxycarbonyl and allyloxycarbonyl; and "an aralkyloxycarbonyl group wherein said aryl ring may be substituted by one or two lower alkoxy or nitro groups" such as benzyloxycarbonyl, 4-methoxybenzyloxy-carbonyl, 3,4-dimethoxybenzyloxycarbonyl, 2-nitrobenzyloxycarbonyl and 4-nitrobenzyloxycarbonyl.

"The hydroxyl protecting group" of $R^1$ and $R^2$ may referably include "the aliphatic acyl group", "the aromatic acyl group", "the methyl group substituted by from 1 to 3 aryl groups", "the methyl group substituted by from 1 to 3 aryl groups wherein said aryl ring is substituted by a lower alkyl, lower alkoxy, halogen or cyano group" or "the silyl group"; more preferably an acetyl group, a benzoyl group, a benzyl group, a p-methoxybenzoyl group, a dimethoxytrityl group, a monomethoxytrityl group or a tert-butyldiphenylsilyl group.

The protecting group of the "protected hydroxyl group" of $R^3$ and $R^4$ or the α group may preferably include "the aliphatic acyl group" or "the aromatic acyl group", more preferably a benzoyl group.

The protecting group of "the protected phosphate group" of $R^1$ and $R^2$ in the above formula (1) represents a protecting group which can be cleaved by a chemical method such as hydrogenolysis, hydrolysis, electrolysis and photolysis and a biological method such as hydrolysis in the human body and such protecting groups may include "a lower alkyl group" such as methyl, ethyl, n-propyl, isopropyl, n-butyl, isobutyl, s-butyl, tert-butyl, n-pentyl, isopentyl, 2-methylbutyl, neopentyl, 1-ethyl-propyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl;

"a cyanated lower alkyl group" such as 2-cyanoethyl and 2-cyano-1,1-dimethylethyl;

"an ethyl group substituted by a silyl group" such as 2-methyldiphenylsilylethyl, 2-trimethylsilylethyl and 2-triphenylsilylethyl;

"a halogenated lower alkyl group" such as 2,2,2-trichloroethyl, 2,2,2-tribromoethyl, 2,2,2-trifluoroethyl and 2,2,2-trichloro-1,1-dimethylethyl;

"a lower alkenyl group" such as ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl and 5-hexenyl, "a cycloalkyl group" such as cyclopropyl, cyclobutyl, cyclopentyl, cyclohexyl, cycloheptyl, norbornyl and adamantyl;

"a cyanated lower alkenyl group" such as 2-cyanobutenyl;

"an aralkyl group" such as benzyl, α-naphthylmethyl, β-naphthylmethyl, indenylmethyl, phenanethrenylmethyl, anthracenylmethyl, diphenylmethyl, triphenylmethyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentyl, 1-phenylhexyl, 2-phenylhexyl, 3-phenylhexyl, 4-phenylhexyl, 5-phenylhexyl, 6-phenylhexyl, 1-naphthylhexyl, 2-naphthylhexyl, 3-naphthylhexyl, 4-naphthylhexyl, 5-naphthylhexyl and 6-naphthylhexyl;

"an aralkyl group wherein said aryl ring is substituted by a nitro group or a halogen atom" such as 4-chlorobenzyl, 2-(4-nitrophenyl)ethyl, o-nitrobenzyl, 4-nitrobenzyl, 2,4-di-nitrobenzyl and 4-chloro-2-nitrobenzyl;

"an aryl group" such as phenyl, indenyl, naphthyl, phenanthrenyl and anthracenyl;

and "an aryl group substituted by a lower alkyl group, a halogen atom or a nitro group" such as 2-methylphenyl, 2,6-dimethylphenyl, 2-chlorophenyl, 4-chlorophenyl, 2,4-dichlorophenyl, 2,5-dichlorophenyl, 2-bromophenyl, 4-nitrophenyl and 4-chloro-2-nitrophenyl;

preferably "the lower alkyl group", "the lower alkyl group substituted by a cyano group", "the aralkyl group" or "the aralkyl group wherein said aryl ring is substituted by a nitro group or a halogen atom"; more preferably a 2-cyanoethyl group, a 2,2,2-trichloroethyl group or a benzyl group.

"The alkoxy group having from 1 to 4 carbon atoms" of $R^3$ and $R^4$ or the α group in the above formula (1) or (2) may include methoxy, ethoxy, n-propoxy, isopropoxy, n-butoxy, isobutoxy, s-butoxy or tert-butoxy, preferably a methoxy or ethoxy group.

The protecting group of "the protected mercapto group" of $R^3$ and $R^4$ or the α group in the above formula (1) or (2) may include, in addition to the hydroxyl protecting groups mentioned above, "a group which forms a disulfide" such as an alkylthio group, e.g., methylthio, ethylthio, tert-butylthio and an aralkylthio group such as benzylthio, preferably "the aliphatic acyl group" or "the aromatic acyl group", more preferably a benzoyl group.

"The alkylthio group having from 1 to 4 carbon atoms" of $R^3$ and $R^4$ or the α group in the above formula (1) or (2) may include methylthio, ethylthio, propylthio, isopropylthio, butylthio, isobutylthio, s-butylthio and tert-butylthio, preferably a methylthio or ethylthio group.

The protecting group of "the protected amino group" of the α group in the above formula (1) or (2) may include "an aliphatic acyl group" such as an alkylcarbonyl group, e.g., formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyl-tetradecanoyl, heptadecanoyl, 15-methylhexadecanoyl, octadecanoyl, 1-methyl-heptadecanoyl, nonadecanoyl, eicosanoyl and heneicosanoyl, a carboxylated alkylcarbonyl group, e.g., succinoyl, glutaroyl and adipoyl, a halogeno lower alkylcarbonyl group, e.g., chloroacetyl, dichloroacetyl, trichloroacetyl and trifluoroacetyl, a lower alkoxy lower alkylcarbonyl group, e.g., methoxyacetyl, and an unsaturated alkylcarbonyl group, e.g., (E)-2-methyl-2-butenoyl;

"an aromatic acyl group" such as an arylcarbonyl group, e.g., benzoyl, α-naphthoyl and β-naphthoyl, a halogenoarylcarbonyl group, e.g., 2-bromobenzoyl and 4-chlorobenzoyl, a lower alkylated arylcarbonyl group, e.g., 2,4,6-trimethylbenzoyl and 4-toluoyl, a lower alkoxylated arylcarbonyl group, e.g., 4-anisoyl, a carboxylated arylcarbonyl group, e.g., 2-carboxybenzoyl, 3-carboxybenzoyl and 4-carboxybenzoyl, a nitrated arylcarbonyl group, e.g., 4-nitrobenzoyl and 2-nitrobenzoyl, a lower alkoxy carbonylated arylcarbonyl group, e.g., 2-(methoxycarbonyl)benzoyl and an arylated arylcarbonyl group, e.g., 4-phenylbenzoyl;

"a lower alkoxycarbonyl group" such as methoxycarbonyl, ethoxycarbonyl, t-butoxycarbonyl and isobutoxycarbonyl;

"a lower alkoxycarbonyl group substituted by halogen or a tri-lower alkylsilyl group" such as 2,2,2-trichloroethoxycarbonyl and 2-trimethylsilylethoxycarbonyl;

"an alkenyloxycarbonyl group" such as vinyloxycarbonyl and allyloxycarbonyl; and "an aralkyloxycarbonyl group wherein said aryl ring may be substituted by a lower alkoxy or nitro group" such as benzyloxycarbonyl, 4-methoxybenzyloxycarbonyl, 3,4-dimethoxybenzyloxycarbonyl, 2-nitrobenzyloxycarbonyl, and 4-nitrobenzyloxy-carbonyl, preferably "the aliphatic acyl group or "the aromatic acyl group", more preferably a benzoyl group.

"The amino group substituted by an alkyl group having from 1 to 4 carbon atoms" of $R^3$ and $R^4$ or the α group in the above formula (1) or (2) may include methylamino, ethylamino, propylamino, isopropylamino, butylamino, isobutylamino, s-butylamino, tert-butylamino, dimethylamino, diethylamino, dipropylamino, diisopropylamino, dibutylamino, diisobutylamino, di(s-butyl)amino and di(tert-butyl)amino, preferably methylamino, ethylamino, dimethylamino, diethylamino or diisopropylamino.

"The cyanoalkoxy group having from 1 to 5 carbon atoms" of $R^3$ and $R^4$ in the above formula (1) represents a group in which the above-described "the alkoxy group having from 1 to 4 carbon atoms" is substituted by a cyano group, and such a group may include cyanomethoxy, 2-cyanoethoxy, 3-cyanopropoxy, 4-cyanobutoxy, 3-cyano-2-methylpropoxy or 1-cyanomethyl-1,1-dimethylmethoxy, preferably a 2-cyanoethoxy group.

"The alkyl group having from 1 to 4 carbon atoms" of the α group in the above formula (1) or (2) may include methyl, ethyl, propyl, isopropyl, butyl, isobutyl, s-butyl and tert-butyl, preferably a methyl or ethyl group.

"The halogen atom" of the a group in the above formula (1) or (2) may include a fluorine atom, a chlorine atom, a bromine atom or an iodine atom, preferably a fluorine atom or a chlorine atom.

The preferred groups of "the purin-9-yl group" and "the substituted purin-9-yl group" of B in the above formula (1) or (2) may include, as a whole, 6-aminopurin-9-yl (i.e., adeninyl), 6-aminopurin-9-yl the amino group of which is protected, 2,6-diaminopurin-9-yl, 2-amino-6-chloropurin-9-yl, 2-amino-6-chloropurin-9-yl the amino group of which is protected, 2-amino-6-fluoropurin-9-yl, 2-amino-6-fluoropurin-9-yl the amino group of which is protected, 2-amino-6-bromopurin-9-yl, 2-amino-6-bromopurin-9-yl the amino group of which is protected, 2-amino-6-hydroxypurin-9-yl (i.e., guaninyl), 2-amino-6-hydroxypurin-9-yl the amino group of which is protected, 2-amino-6-hydroxypurin-9-yl the amino and hydroxyl groups of which are protected, 6-amino-2-methoxypurin-9-yl, 6-amino-2-chloropurin-9-yl, 6-amino-2-fluoropurin-9-yl, 2,6-dimethoxypurin-9-yl, 2,6-dichloropurin-9-yl or 6-mercaptopurin-9-yl, more preferably a 6-benzoylaminopurin-9-yl, adeninyl, 2-isobutyrylamino-6-hydroxypurin-9-yl or guaninyl group.

The preferred groups of "the 2-oxo-pyrimidin-1-yl group" and "the substituted 2-oxo-pyrimidin-1-yl group" of B in the above formula (1) or (2) may include, as a whole, 2-oxo-4-amino-pyrimidin-1-yl (i.e., cytosinyl), 2-oxo-4-amino-pyrimidin-1-yl the amino group of which is protected, 2-oxo-4-amino-5-fluoro-pyrimidin-1-yl, 2-oxo-4-amino-5-fluoropyrimidin-1-yl the amino group of which is protected, 4-amino-2-oxo-5-chloro-pyrimidin-1-yl, 2-oxo-4-methoxy-pyrimidin-1-yl, 2-oxo-4-mercapto-pyrimidin-1-yl, 2-oxo-4-hydroxy-pyrimidin-1-yl (i.e., uracinyl), 2-oxo-4-hydroxy-5-methylpyrimidin-1-yl (i.e., thyminyl) or 4-amino-5-methyl-2-oxo-pyrimidin-1-yl (i.e., 5-methylcytosinyl) group, more preferably 2-oxo-4-benzoylamino-pyrimidin-1-yl, cytosinyl, thyminyl, uracinyl, 2-oxo-4-benzoylamino-5-methylpyrimidin-1-yl or 5-methylcytosinyl group. "The nucleoside analogue" refers to a non-natural type of "nucleoside" in which a purine or pyrimidine group is attached to a sugar.

"The oligonucleotide analogue" refers to a non-natural type of "oligonucleotide" derivative in which from 2 or more and up to 100 and preferably 2 to 50 and more preferably 10 to 30 "nucleosides", which may be the same or different, are bonded through a phosphodiester bond and such analogues may preferably include sugar derivatives in which the sugar moiety is modified; thioate derivatives in which the phosphodiester bond moiety is thioated (phosphorothioate bond); ester products in which a terminal phosphate moiety is esterified; and amide products in which an amino group on a purine base is amidated, more preferably the sugar derivatives in which the sugar moiety (ribose or deoxyribose) is modified and the thioate derivatives in which the phosphodiester moiety is thioated.

Naturally occurring oligonucleotides are those which occur in nature, for example, ribose and deoxyribose phosphodiester oligonucleotides having adenine, guanine, cytosine, thymine and uracil nucleobases. As used herein, "oligonucleotide analogues" are oligonucleotides that contain modified sugar, internucleoside linkage and/or nucleobase moieties. Such oligonucleotide analogs are typically structurally distinguishable from, yet functionally interchangeable with, naturally occurring or synthetic wild type oligonucleotides. Thus, non-naturally occurring oligonucleotides include all such structures which function effectively to mimic the structure and/or function of a desired RNA or DNA strand, for example, by hybridizing to a target.

The nucleosides other than formula (2) in the oligonucleotide analogues of the present invention are any of the known nucleosides or not yet known nucleosides that are functionally interchangeable with naturally-occurring nucleosides. Preferably such nucleosides have the structure of a nucleobase and a sugar defined as follows.

Representative nucleobases include adenine, guanine, cytosine, uracil, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8- halo, oxa, amino, thiol, thioalkyl, hydroxyl and other 8-substituted adenines and guanines, 5-trifluoromethyl and other 5-substituted uracils and cytosines, 7-methylguanine. Further naturally and non naturally occurring nucleobases include those disclosed in U.S. Pat. No. 3,687,808 (Merigan, et al.), in chapter 15 by Sanghvi, in *Antisense Research and Application*, Ed. S. T. Crooke and B. Lebleu, CRC Press, 1993, in Englisch et al., *Angewandte Chemie*, International Edition, 1991, 30, 613-722 (see especially pages 622 and 623, and in the *Concise Encyclopedia of Polymer Science and Engineering*, J. I. Kroschwitz Ed., John Wiley & Sons, 1990, pages 858-859, and Cook, *Anti-Cancer Drug Design*, 1991, 6, 585-607, each of which publications are hereby incorporated by reference in their entirety). The term "nucleosidic base" is further intended to include heterocyclic compounds that can serve as like nucleosidic bases including certain "universal bases" that are not nucleosidic bases in the most classical sense but serve as nucleosidic bases. Especially mentioned as a universal base is 3-nitropyrrole.

Preferred 2'-groups of the sugar include H, OH, F, and O—, S—, or N-alkyl groups. One particularly preferred group includes 2'-methoxyethoxy[2'—O—$CH_2CH_2OCH_3$, also known as 2'—O—(2-methoxyethyl) or 2'-MOE] (Martin et al. , *Helv. Chim. Acta,* 1995, 78, 486), i.e., an alkoxyalkoxy group. A further preferred modification includes 2'-dimethylaminooxyethoxy, i.e., a O($CH_2$)$_2$ON ($CH_3$)$_2$ group, also known as 2'-DMAOE, as described in U.S. Pat. No. 6,127,533, the entire contents of which are herein incorporated by reference. Other preferred modifications include 2'-methoxy (2'—O—$CH_3$) and 2'-aminopropoxy (2'—O$CH_2CH_2CH_2NH_2$).

Sugars of nucleosides having O-substitutions on the ribosyl ring are also amenable to the present invention. Representative substitutions for ring O include S, $CH_2$, CHF, and $CF_2$, see, e.g., Secrist, et al., Abstract 21, Program & Abstracts, Tenth International Roundtable, Nucleosides, Nucleotides and their Biological Applications, Park City, Utah, Sep. 16-20, 1992, which is hereby incorporated by reference in its entirety.

Internucleoside linkages may be any of the known internucleoside linkages, or may be any internucleoside linkage not yet known that can be incorporated into an oligonucleotide according to synthetic chemistry with which the process according to the invention is compatible. In certain preferred embodiments, the other internucleoside linkages are phosphodiester or phosphorothioate linkages. In the case of phosphorothioate internucleoside linkages, the linkages may be phosphorothioate mixed enantiomers or stereoregular phosphorothioates (see Iyer et al., *Tetrahedron Asymmetry* 6: 1051-1054 (1995).

Additional modifications may also be made at other positions on the oligonucleotide, particularly the 3' position of the sugar, on the 3' terminal nucleotide and the 5' position of 5' terminal nucleotide. For example, one additional modification of the oligonucleotides of the present invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA*, 1989, 86, 6553), cholic acid (Manoharan et al., *Bioorg. Med. Chem. Lett.*, 1994, 4, 1053), a thioether, e.g., hexyl-S-tritylthiol (Manoharan et al., *Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di- hexadecyl-rac-glycerol or triethylammonium 1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), or adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylamino-carbonyl- oxycholesterol moiety (Crooke et al., *J. Pharmacol. Exp. Ther.*, 1996, 277, 923).

Non-limiting examples of nucleosides other than of the formula (2) are as follows: adenosine, guanosine, cytidine, 5-methylcytidine, uridine, 5-methyluridine, inosine, 5-(1-propynyl)cytidine, 5-(1-propynyl)uridine, 2'-deoxyadenosine, 2'-deoxyguanosine, 2'-deoxycytidine, 5-methyl-2'-deoxycytidine, 2'-deoxyuridine,thymidine, 2'-deoxyinosine, 2'-deoxy-5-(1-propynyl)cytidine, 2'-deoxy-5-(1-propynyl)uridine, 2'-O-methyladenosine, 2'-O-methylguanosine, 2'-O-methylcytidine, 5-methyl-2'-O-methylcytidine, 2'-O-methyluridine,5-methyl-2'-O-methyluridine, 2'-O-methylinosine, 5-(1 -propynyl)-2'-O-methylcytidine, 5-(1-propynyl)-2'-O-methyluridine, 2'-O-allyladenosine, 2'-O-allylguanosine, 2'-O-allylcytidine, 5-methyl-2'-O-allylcytidine, 2'-O-allyluridine,5-methyl-2'-O-allyluridine, 2'-O-allylinosine, 5-(1-propynyl)-2'-O-allylcytidine, 5-(1-propynyl)-2'-O-allyluridine, 2'-O-propargyladenosine, 2'-O-propargylguanosine, 2'-O-propargylcytidine, 5-methyl-2'-O-propargylcytidine, 2'-O-propargyluridine,5-methyl-2'-O-propargyluridine, 2'-O-propargylinosine, 5-(1-propynyl)-2'-O-propargylcytidine, 5-(1-propynyl)-2'-O-allyluridine, 2'-O-(2-methoxyethyl)adenosine, 2'-O-(2-methoxyethyl)guanosine, 2'-O-(2-methoxyethyl)cytidine, 5-methyl-2'-O-(2-methoxyethyl) cytidine, 2'-O-(2-methoxyethyl)uridine, 5-methyl-2'-O-(2-methoxyethyl)uridine, 2'-O-(2-methoxyethyl)inosine, 5-(1-propynyl)-2'-O-(2-methoxyethyl)cytidine, 5-(1-propynyl)-2'-O-(2-methoxyethyl)uridine, 2'-O-(2-dimethylaminooxyethyl)adenosine, 2'-O-(2-dimethylaminooxyethyl)guanosine, 2'-O-(2-dimethylaminooxyethyl)cytidine, 5-methyl-2'-O-(2-dimethylaminooxyethyl)cytidine, 2'-O-(2-dimethylaminooxyethyl)uridine,5-methyl-2'-O-(2-dimethylaminooxyethyl) uridine, 2'-O-(2-dimethylaminooxyethyl)inosine, 5-(1-propynyl)-2'-O-(2-dimethylaminooxyethyl)cytidine, 5-(1-propynyl)-2'-O-(2-dimethylaminooxyethyl)uridine, 2'-fluoro-2'-deoxyadenosine, 2'-fluoro-2'-deoxyguanosine, 2'-fluoro-2'-deoxycytidine, 5-methyl-2'-fluoro-2'-deoxycytidine, 2'-fluoro-2'-deoxyuridine, 5-methyl-2'-fluoro-2'-deoxyuridine, 2'-fluoro-2'-deoxyinosine, 5-(1-propynyl)-2'-fluoro-2'-deoxyuridine, 5-(1-propynyl)-2'-fluoro-2'-deoxyuridine, 2'-amino-2'-deoxyadenosine, 2'-amino-2'-deoxyguanosine, 2'-amino-2'-deoxycytidine, 5-methyl-2'-amino-2'-deoxycytidine, 2'-amino-2'-deoxyuridine, 5-methyl-2'-amino-2'-deoxyuridine, 2'-amino-2'-deoxyinosine, 5-(1-propynyl)-2'-amino-2'-deoxyuridine, and 5-(1-propynyl)-2'-amino-2'-deoxyuridine.

In some preferred embodiments of the oligonucleotide analogues according to the present invention, several adjacent oligonucleotide analogues comprise two regions, which are the first and the second regions. Hereinafter "the first region" comprises one or more nucleoside analogues of the formula (2) and each nucleoside is connected by a phosphodiester bond; hereinafter the "second region" comprises one or more of a 2'-deoxynucleoside (e.g., 2'-deoxyadenosine, 2'-deoxyguanosine, 2'-deoxycytidine, thymidine, 2'-deoxyuridine, 5-substituted-2'-deoxycytidine or 5-substituted-2'-deoxyuridine) and each nucleoside is connected by a phosphodiester bond or a phosphorothioate bond.

In certain particularly preferred oligonucleotide analogues, the total number of nucleosides is from 5 to 100, more preferably 10 to 50, and the oligonucleotide analogues comprise the second region whose number of nucleoside residues is about half of the total number of nucleoside residues flanked on both sides by the first region, whose number of nucleoside is about a quarter of the total number of nucleoside residues. In this case, each nucleoside of the second region is preferably connected by a phosphorothioate bond and the bonds between the first region and the second region are phosphodiester bonds or phosphorothioate bonds.

In other certain particularly preferred oligonucleotide analogues, the total number of nucleosides is from 5 to 100, and the entire oligonucleotide analogue comprises (a) one or more of the nucleoside analogues of the formula (2) and one or more nucleosides selected from the group consisting of (b) a 2'-deoxynucleoside (e.g. 2'-deoxyadenosine, 2'-deoxyguanosine, 2'-deoxycytidine, thymidine, 2'-deoxyuridine, 5-substituted-2'-deoxycytidine or 5-substituted-2'-deoxyuridine) and (c) a 2'-O-methyl ribonucleoside (e.g., 2'-O-methyladenosine, 2'-O-methylguanosine, 2'-O-methylcytidine, 5-methyl-2'-O-methyluridine, 2'-O-methyluridine, 5-substituted-2'-O-methylcytidine or 5-substituted-2'-O-methyluridine). In this case, each every other nucleoside is a nucleoside analogue of the formula (2) and the bonds between each nucleoside are preferably phosphodiester bonds.

"The salt thereof" refers to salts of the compound (1) of the present invention since they can be converted to salts and such salts may preferably include inorganic salts for example metal salts such as alkali metal salts, e.g., sodium salts, potassium salts and lithium salts, alkaline earth metal salts, e.g., calcium salts and magnesium salts, aluminum salts, iron salts, zinc salts, copper salts, nickel salts and cobalt salts; amine salts such as inorganic salts, e.g., ammonium salts, organic salts, e.g., t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'- dibenzylethylenediamine salts, chloroprocaine salts, procaine salts, diethanol amine salts, N-benzyl-phenethylamine salts, piperazine salts, tetramethylammonium salts and a tris(hydroxymethyl)aminomethane salts; inorganic acid salts such as hydrohalogenic acid salts, e.g., hydrofluoric acid salts, hydrochloric acid salts, hydrobromic acid salts and hydroiodic acid salts, nitric acid salts, perchloric acid salts, sulfuric acid salts and phosphoric acid salts; organic acid salts such as lower alkanesulfonic acid salts, e.g., methanesulfonic acid salts, trifluoromethanesulfonic acid salts and ethanesulfonic acid salts, arylsulfonic acid salts, e.g., benzenesulfonic acid salts and p-toluenesulfonic acid salts, acetic acid salts, malic acid salts, fumaric acid salts, succinic acid salts, citric acid salts, tartaric acid salts, oxalic acid salts and maleic acid salts; and amino acid salts such as glycine salts, lysine salts, arginine salts, ornithine salts, glutamic acid salts and aspartic acid salts.

The modified oligonucleotides or the polynucleotide analogues of the present invention can be converted to a salt. Where the modified oligonucleotides or polynucleotide analogues are to be used as a probe, a primer for starting amplification or as intermediates, the salts are any of the salts noted above for the salts of the compound (1) of the present invention. Where, however, they are to be used as a pharmaceutical, the salts should be "pharmacologically acceptable salts thereof". The "pharmacologically acceptable salts thereof" refers to a salt thereof, and such salts may preferably include inorganic salts for example metal salts such as alkali metal salts, e.g., sodium salts, potassium salts lithium salts, alkaline earth metal salts, e.g., calcium salts and magnesium salts, aluminum salts, iron salts, zinc salts, copper salts, nickel salts and cobalt salts; amine salts such as inorganic salts, e.g., ammonium salts, organic salts, e.g., t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetra-methylammonium salts and tris(hydroxymethyl)aminomethane salts; inorganic acid salts such as hydrohalogenic acid salts, e.g., hydrofluoric acid salts, hydrochloric acid salts, hydrobromic acid salts and hydroiodic acid salts, nitric acid salts, perchloric acid salts, sulfuric acid salts and phosphoric acid salts; organic acid salts such as lower alkanesulfonic acid salts, e.g., methanesulfonic acid salts, trifluoromethanesulfonic acid salts and ethanesulfonic acid salts, arylsulfonic acid salts, e.g., benzenesulfonic acid salts and p-toluenesulfonic acid salts, acetic acid salts, malic acid salts, fumaric acid salts, succinic acid salts, citric acid salts, tartaric acid salts, oxalic acid salts and maleic acid salts; and amino acid salts such as glycine salts, lysine salts, arginine salts, ornithine salts, glutamic acid salts and aspartic acid salts.

The term "strand displacement" relates to a process whereby an oligonucleotide binds to its complementary target sequence in a double stranded DNA or RNA so as to displace the other strand from said target strand.

Several diagnostic and molecular biology procedures have been developed that utilize panels of different oligonucleotides to simultaneously analyze a target nucleic acid for the presence of a plethora of possible mutations. Typically, the oligonucleotide panels are immobilized in a predetermined pattern on a solid support such that the presence of a particular mutation in the target nucleic acid can be revealed by the position on the solid support where it hybridizes. One important prerequisite for the successful use of panels of different oligonucleotides in the analysis of nucleic acids is that they are all specific for their particular target sequence under the single applied hybridization condition. Since the affinity and specificity of standard oligonucleotides for their complementary target sequences depend heavily on their sequence and size this criteria has been difficult to fulfill so far.

In a preferred embodiment of the present invention, therefore, oligonucleotide analogues are used as a means to increase affinity and/or specificity of the probes and as a means to equalize the affinity of different oligonucleotides for their complementary sequences. As disclosed herein such affinity modulation can be accomplished by, e.g., replacing selected nucleosides in the oligonucleotide with an nucleoside of formula (2) carrying a similar nucleobase.

In another preferred embodiment of the present invention, the high affinity and specificity of oligonucleotide analogues is exploited in the sequence specific capture and purification of natural or synthetic nucleic acids. In one aspect, the natural or synthetic nucleic acids are contacted with oligonucleotide analogues immobilized on a solid surface. In this case hybridization and capture occurs simultaneously. The captured nucleic acids may be, for instance, detected, characterized, quantified or amplified directly on the surface by a variety of methods well known in the art or it may be released from the surface, before such characterization or amplification occurs, by subjecting the immobilized, modified oligonucleotide and captured nucleic acid to dehybridizing conditions, such as, for example, heat or by using buffers of low ionic strength.

The solid support may be chosen from a wide range of polymer materials such as, for instance, CPG (controlled pore glass), polypropylene, polystyrene, polycarbonate or polyethylene and it may take a variety of forms such as, for instance, a tube, a microtiter plate, a stick, a bead, a filter, etc. The oligonucleotide analogues may be immobilized to the solid support via its 5' or 3' end (or via the terminus of linkers attached to the 5' or 3' end) by a variety of chemical or photochemical methods usually employed in the immobilization of oligonucleotides or by non-covalent coupling such as for instance via binding of a biotinylated oligonucleotide analogues to immobilized streptavidin. One preferred method for immobilizing oligonucleotide analogues on different solid supports is a photochemical method using a photochemically active anthraquinone covalently attached to the 5' or 3' end of the oligonucleotide analogues (optionally via linkers) as described in WO 96/31557. Thus, the present invention also provides a surface carrying an oligonucleotide analogue.

In another aspect, the oligonucleotide analogue carries a ligand covalently attached to either the 5' or 3' end. In this case the oligonucleotide analogue is contacted with natural or synthetic nucleic acids in solution whereafter the hybrids formed are captured onto a solid support carrying molecules that can specifically bind the ligand.

In still another aspect, oligonucleotide analogues capable of performing "strand displacement" are used in the capture of natural and synthetic nucleic acids without prior denaturation. Such modified oligonucleotides are particularly useful in cases where the target sequence is difficult or impossible to access by normal oligonucleotides due to the rapid formation of stable intramolecular structures.

Examples of nucleic acids containing such structures are rRNA, tRNA, snRNA and scRNA.

In another preferred embodiment of the present invention, oligonucleotide analogues designed with the purpose of high specificity are used as primers in the sequencing of nucleic acids and as primers in any of the several well known amplification reactions, such as the PCR reaction. As shown herein, the design of the oligonucleotide analogues determines whether it will sustain a exponential or linear target amplification. The products of the amplification reaction can be analyzed by a variety of methods applicable to the analysis of amplification products generated with normal DNA primers. In the particular case where the oligonucleotide analogue primers are designed to sustain a linear amplification the resulting amplicons will carry single stranded ends that can be targeted by complementary probes without denaturation.

Such ends could for instance be used to capture amplicons by other complementary oligonucleotide analogues attached to a solid surface.

In another aspect, oligonucleotide analogues capable of "strand displacement" are used as primers in either linear or exponential amplification reactions. The use of such oligos is expected to enhance overall amplicon yields by effectively competing with amplicon re-hybridization in the later stages of the amplification reaction. Demers, et al. (*Nucl. Acid Res.*, 1995, Vol 23, 3050-3055) discloses the use of high-affinity, non-extendible oligos as a means of increasing the overall yield of a PCR reaction. It is believed that the oligomers elicit these effect by interfering with amplicon re-hybridization in the later stages of the PCR reaction. It is expected that oligonucleotide analogue blocked at their 3' end will provide the same advantage. Blocking of the 3' end can be achieved in numerous ways like for instance by exchanging the 3' hydroxyl group with hydrogen or phosphate. Such 3' blocked oligonucleotide analogues can also be used to selectively amplify closely related nucleic acid sequences in a way similar to that described by Yu et al. (*Biotechniques*, 1997, 23, 714-716).

In recent years, novel classes of probes that can be used in, for example, real-time detection of amplicons generated by target amplification reactions have been invented.

One such class of probes have been termed "Molecular Beacons". These probes are synthesized as partly self-complementary oligonucleotides containing a fluorophor at one end and a quencher molecule at the other end. When free in solution, the probe folds up into a hairpin structure (guided by the self-complimentary regions) which positions the quencher in sufficient closeness to the fluorophor to quench its fluorescent signal. Upon hybridization to its target nucleic acid, the hairpin opens thereby separating the fluorophor and quencher and giving off a fluorescent signal.

Another class of probes have been termed "Taqman probes". These probes also contain a fluorophor and a quencher molecule. Contrary to the "Molecular Beacons", however, the ability of the quenchers to quench the fluorescent signal from the fluorophor is maintained after hybridization of the probe to its target sequence. Instead, the fluorescent signal is generated after hybridization by physical detachment of either the quencher or the fluorophor from the probe by the action of the 5'0 exonuclease activity of a polymerase which has initiated synthesis from a primer located 5' to the binding site of the Taqman probe.

High affinity for the target site is an important feature in both types of probes and consequently such probes tends to be fairly large (typically 30 to 40 mers). As a result, significant problems are encountered in the production of high quality probes.

In a preferred embodiment, therefore, the oligonucleotide analogue is used to improve production and subsequent performance of "Taqman probes" and "Molecular Beacons" by reducing their size, whilst retaining the required affinity.

In a further aspect, the oligonucleotide analogues are used to construct new affinity pairs (either fully or partially modified oligonucleotides). The affinity constants can easily be adjusted over a wide range and a vast number of affinity pairs can be designed and synthesized.

One part of the affinity pair can be attached to the molecule of interest (e.g., proteins, amplicons, enzymes, polysaccharides, antibodies, haptens, peptides, PNA, etc.) by standard methods, while the other part of the affinity pair can be attached to e.g., a solid support such as beads, membranes, microtiter plates, sticks, tubes, etc. The solid support may be chosen from a wide range of polymer materials such as for instance polypropylene, polystyrene, polycarbonate or polyethylene. The affinity pairs may be used in selective isolation, purification, capture and detection of a diversity of the target molecules mentioned above.

The principle of capturing oligonucleotide analogue by ways of interaction with another complementary oligonucleotide analogue (either fully or partially modified) can be used to create an infinite number of novel affinity pairs.

In another preferred embodiment, the high affinity and specificity of the oligonucleotide analogues are exploited in the construction of probes useful in in-situ hybridization. For instance, an oligonucleotide analogue could be used to reduce the size of traditional DNA probes, whilst maintaining the required affinity thereby increasing the kinetics of the probe and its ability to penetrate the sample specimen. The ability of the oligonucleotide analogues to "strand displace" double stranded nucleic acid structures are also of considerable advantage in in-situ hybridization, because it facilitates hybridization without prior denaturation of the target DNA/RNA.

The present invention also provides a kit for the isolation, purification, amplification, detection, identification, quantification, or capture of natural or synthetic nucleic acids, wherein the kit comprises a reaction body and one or more oligonucleotide analogues as defined herein. The oligonucleotide analogues are preferably immobilized onto said reaction body (e.g., by using the immobilizing techniques described above).

For the kits according to the invention, the reaction body is preferably a solid support material, e.g., selected from borosilicate glass, soda-lime glass, polystyrene, polycarbonate, polypropylene, polyethylene, polyethyleneglycol terephthalate, polyvinyl acetate, polyvinylpyrrolidinone, polymethylmethacrylate and polyvinylchloride, preferably polystyrene and polycarbonate. The reaction body may be in the form of a specimen tube, a vial, a slide, a sheet, a film, a bead, a pellet, a disc, a plate, a ring, a rod, a net, a filter, a tray, a microtiter plate, a stick, or a multi-bladed stick.

The kits are typically accompanied by a written instruction sheet stating the optimal conditions for the use of the kit.

"Antigene activity" is the ability to inhibit gene expression by forming a triplex with a DNA duplex. "Antisense activity" is the ability to inhibit gene expression by forming a duplex with a sense sequence. A triplex with a DNA duplex means the state that an oligonucleotide fits into the groove of a DNA duplex strand, known as a "major groove".

The oligonucleotides of the present invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the present invention. Seemingly diverse organisms such as bacteria, yeast, protozoa, algae, all plants and all higher animal forms, including warm-blooded animals, including humans, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides.

Some representative therapeutic indications and other uses for the compounds of the invention are as follows:

One of the most significant health problems is the inadequate treatment of pain. The impact of pain places great burden in economic terms as well as in human suffering. Neuropathic pain is one of the most difficult pains to treat and cure. The primary site of this abnormal and ectopic site is the dorsal root ganglion (DRG) of the injured site. In the DRG, two main types of sodium currents, termed TTX-sensitive and TTX-resistant, have been identified. The blockage of the sodium channel PN3/SNS, which is TTX-resistant, is a candidate for pain relief. Antisense compounds targeted to PN3/SNS are described in Porreca et al. *Proc. Natl. Acad. Sci.* 1999, 96, 7640-7644.

Another therapeutic indication of particular interest with respect to the present invention is psoriasis. Psoriasis is a common chronic and recurrent disease characterized by dry, well-circumscribed, silvery, scaling papules and plaques of various sizes. The disease varies in severity from a few lesions to widespread dermatosis with disabling arthritis or exfoliation. The ultimate cause of psoriasis is presently not known, but the thick scaling that occurs is probably due to increased epidermal cell proliferation (*The Merck Manual of Diagnosis and Therapy*, 15th Ed., pp. 2283-2285, Berkow et al., eds., Rahway, N.J., 1987). Inhibitors of Protein Kinase C (PKC) have been shown to have both antiproliferative and anti-inflammatory effects in vitro. Some antipsoriasis drugs, such as cyclosporin A and anthralin, have been shown to inhibit PKC, and inhibition of PKC has been suggested as a therapeutic approach to the treatment of psoriasis (Hegemann, L. and G. Mahrle, *Pharmacology of the Skin*, H. Mukhtar, ed., pp. 357-368, CRC Press, Boca Raton, Fla., 1992). Antisense compounds targeted to Protein Kinase C (PKC) proteins are described in U.S. Pat. No. 5,620,963 to Cook et al. and U.S. Pat. No. 5,681,747 to Boggs et al.

A further therapeutic indication of interest to the present invention are inflammatory disorders of the skin. These occur in a variety of forms including, for example, lichen planus, toxic epidermal necrolyis (TEN), ertyhema multiforme and the like (*The Merck Manual of Diagnosis and Therapy*, 15th Ed., pp. 2286-2292, Berkow et al., eds., Rahway, N.J., 1987). Expression of ICAM-1 has been associated with a variety of inflammatory skin disorders such as allergic contact dermatitis, fixed drug eruption, lichen planus and psoriasis (Ho et al., *J. Am. Acad. Dermatol.*, 1990, 22, 64; Griffiths et al., *Am. J. Pathology*, 1989, 135, 1045; Lisby et al., *Br. J. Dermatol.*, 1989, 120, 479; Shiohara et al., *Arch. Dermatol.*, 1989, 125, 1371; Regezi et al., Oral Surg. Oral Med. Oral Pathol., 1996, 81, 682). Moreover, intraperitoneal administration of a monoclonal antibody to ICAM-1 decreases ovalbumin-induced eosinophil infiltration into skin in mice (Hakugawa et al., J. Dermatol., 1997, 24, 73). Antisense compounds targeted to ICAM-1 are described in U.S. Pat. Nos. 5,514,788, 5,591,623 and 6,111,094.

Other antisense targets for skin inflammatory disorders are VCAM-1 and PECAM-1. Intraperitoneal administration of a monoclonal antibody to VCAM-1 decreases ovalbumin-induced eosinophil infiltration into the skin of mice (Hakugawa et al., *J. Dermatol.*, 1997, 24, 73). Antisense compounds targeted to VCAM-1 are described in U.S. Pat. Nos. 5,514,788 and 5,591,623. PECAM-1 proteins are glycoproteins which are expressed on the surfaces of a variety of cell types (for reviews, see Newman, *J. Clin. Invest.*, 1997, 99, 3 and DeLisser et al., *Immunol. Today*, 1994, 15, 490). In addition to directly participating in cell-cell interactions, PECAM-1 apparently also regulates the activity and/or expression of other molecules involved in cellular interactions (Litwin et al., *J. Cell Biol.*, 1997, 139, 219) and is thus a key mediator of several cell: cell interactions. Antisense compounds targeted to PECAM-1 are described in U.S. Pat. No. 5,955,443.

Another type of therapeutic indication of interest for using oligonucleotides of the present invention encompasses a variety of cancers of the skin. Representative skin cancers include benign tumors (warts, moles and the like) and malignant tumors such as, for example, basal cell carcinoma, squamous cell carcinoma, malignant melanoma, Paget's disease, Kaposi's sarcoma and the like (*The Merck Manual of Diagnosis and Therapy*, 15th Ed., pp. 2301-2310, Berkow et al., eds., Rahway, N.J., 1987). A number of molecular targets involved in tumorigenesis, maintenance of the hyperproliferative state and metastasis are targeted to prevent or inhibit skin cancers, or to prevent their spread to other tissues.

The ras oncogenes are guanine-binding proteins that have been implicated in cancer by, e.g., the fact that activated ras oncogenes have been found in about 30% of human tumors generally; this figure approached 100% in carcinomas of the exocrine pancreas (for a review, see Downward, *Trends in Biol. Sci.*, 1990, 15, 469). Antisense compounds targeted to H-ras and K-ras are described in U.S. Pat. No. 5,582,972 to Lima et al., U.S. Pat. No. 5,582,986 to Monia et al. and U.S. Pat. No. 5, 661,134 to Cook et al., and in published PCT application WO 94/08003.

Protein Kinase C (PKC) proteins have also been implicated in tumorigenesis. Antisense compounds targeted to Protein Kinase C (PKC) proteins are described in U.S. Pat. No. 5,620,963 to Cook et al. and U.S. Pat. No. 5,681,747 to Boggs et al. Also of interest are AP-1 subunits and JNK proteins, particularly in regard to their roles in tumorigenesis and metastasis. The process of metastasis involves a sequence of events wherein (1) a cancer cell detaches from its extracellular matrices, (2) the detached cancer cell migrates to another portion of an animal's body, often via the circulatory system, and (3) attaches to a distal and inappropriate extracellular matrix, thereby created a focus from which a secondary tumor can arise. Normal cells do not possess the ability to invade or metastasize and/or undergo apoptosis (programmed cell death) if such events occur (Ruoslahti, *Sci. Amer.*, 1996, 275, 72). However, many human tumors have elevated levels of activity of one or more matrix metalloproteinases (MMPs) (Stetler-Stevenson et al., *Annu. Rev. Cell Biol.*, 1993, 9, 541; Bernhard et al.,

*Proc. Natl. Acad. Sci.* (U.S.A.), 1994, 91, 4293. The MMPs are a family of enzymes which have the ability to degrade components of the extracellular matrix (Birkedal-Hansen, *Current Op. Biol.,* 1995, 7, 728). In particular, one member of this family, matrix metalloproteinase-9 (MMP-9), is often found to be expressed only in tumors and other diseased tissues (Himelstein et al., *Invasion & Metastasis,* 1994, 14, 246).

Several studies have shown that regulation of the MMP-9 gene may be controlled by the AP-1 transcription factor (Kerr et al., *Science,* 1988, 242, 1242; Kerr et al., *Cell,* 1990, 61, 267; Gum et al., *J. Biol. Chem.,* 1996, 271, 10672; Hua et al., *Cancer Res.,* 1996, 56, 5279). Inhibition of AP-1 function has been shown to attenuate MMP-9 expression (U.S. Pat. No. 5,985,558). AP-1 is a heterodimeric protein having two subunits, the gene products of fos and jun. Antisense compounds targeted to c-fos and c-jun are described in U.S. Pat. No. 5,985,558.

Furthermore, AP-1 is itself activated in certain circumstances by phosphorylation of the Jun subunit at an amino-terminal position by Jun N-terminal kinases (JNKs). Thus, inhibition of one or more JNKs is expected to result in decreased AP-1 activity and, consequentially, reduced MMP expression. Antisense compounds targeted to JNKs are described in U.S. Pat. No. 5,877,309.

Infectious diseases of the skin are caused by viral, bacterial or fungal agents. In the case of Lyme disease, the tick borne causative agent thereof, the spirochete Borrelia burgdorferi, up-regulates the expression of ICAM-1, VCAM-1 and ELAM-1 on endothelial cells in vitro (Boggemeyer et al., *Cell Adhes. Comm.,* 1994, 2, 145). Furthermore, it has been proposed that the mediation of the disease by the anti-inflammatory agent prednisolone is due in part to mediation of this up-regulation of adhesion molecules (Hurtenbach et al., *Int. J. Immunopharmac.,* 1996, 18, 281). Thus, potential targets for therapeutic mediation (or prevention) of Lyme disease include ICAM-1, VCAM-1 and ELAM-1 (supra).

Other infectious disease of the skin which are tractable to treatment using the compositions and methods of the invention include disorders resulting from infection by bacterial, viral or fungal agents (*The Merck Manual of Diagnosis and Therapy,* 15th Ed., pp. 2263-2277, Berkow et al., eds., Rahway, N.J., 1987).

With regard to infections of the skin caused by fungal agents, U.S. Pat. No. 5,691,461 describes antisense compounds for inhibiting the growth of *Candida albicans*.

With regard to infections of the skin caused by viral agents, U.S. Pat. Nos. 5,166,195, 5,523,389 and 5,591,600 concern oligonucleotide inhibitors of Human Immunodeficiency Virus (HIV). U.S. Pat. No. 5,004,810 is directed to oligomers capable of hybridizing to herpes simplex virus Vmw65 mRNA and inhibiting its replication. U.S. Pat. Nos. 5,194,428 and 5,580,767 disclose antisense compounds having antiviral activity against influenzavirus. U.S. Pat. No. 4,806,463 relates to antisense compounds and methods using them to inhibit HTLV-III replication. U.S. Pat. Nos. 4,689, 320, 5,442,049, 5,591,720 and 5,607,923 are directed to antisense compounds as antiviral agents specific to cytomegalovirus (CMV). U.S. Pat. No. 5,242,906 describes antisense compounds useful in the treatment of latent Epstein-Barr virus (EBV) infections. U.S. Pat. Nos. 5,248, 670, 5, 514,577 and 5,658,891 provide antisense compounds useful in the treatment of herpesvirus infections. U.S. Pat. Nos. 5,457,189 and 5,681,944 disclose antisense compounds useful in the treatment of papillomavirus infections. The antisense compounds disclosed in the aforesaid U.S. patents, all of which U.S. patents are herein incorporated by reference, may be used with (or replaced by) the compositions of the present invention to effect prophylactic, palliative or therapeutic relief from diseases caused or exacerbated by the indicated pathogenic agents.

Antisense oligonucleotides of the present invention may also be used to determine the nature, function and potential relationship of various genetic components of the body to disease or body states in animals. Heretofore, the function of a gene has been chiefly examined by the construction of loss-of-function mutations in the gene (i.e., "knock-out" mutations) in an animal (e.g., a transgenic mouse). Such tasks are difficult, time-consuming and cannot be accomplished for genes essential to animal development, since the "knock-out" mutation would produce a lethal phenotype. Moreover, the loss-of-function phenotype cannot be transiently introduced during a particular part of the animal's life cycle or disease state; the "knock-out" mutation is always present. "Antisense knockouts," that is, the selective modulation of expression of a gene by antisense oligonucleotides, rather than by direct genetic manipulation, overcomes these limitations (see, for example, Albert et al., *Trends in Pharmacological Sciences,* 1994, 15, 250). In addition, some genes produce a variety of mRNA transcripts as a result of processes such as alternative splicing; a "knock-out" mutation typically removes all forms of mRNA transcripts produced from such genes and thus cannot be used to examine the biological role of a particular mRNA transcript. Antisense oligonucleotides have been systemically administered to rats in order to study the role of the N-methyl-D-aspartate receptor in neuronal death, to mice in order to investigate the biological role of protein kinase C-a, and to rats in order to examine the role of the neuropeptide Y1 receptor in anxiety (Wahlestedt et al., *Nature,* 1993, 363:260; Dean et al. , *Proc. Natl. Acad. Sci. U.S.A.,* 1994, 91:11762; and Wahlestedt et al., *Science,* 1993, 259:528, respectively). In instances where complex families of related proteins are being investigated, "antisense knockouts" (i.e., inhibition of a gene by systemic administration of antisense oligonucleotides) may represent the most accurate means for examining a specific member of the family (see, generally, Albert et al., *Trends Pharmacol. Sci.,* 1994, 15:250). By providing compositions and methods for the simple non-parenteral delivery of oligonucleotides and other nucleic acids, the present invention overcomes these and other shortcomings.

With the growing insight of the potential biological role of triple helical nucleic acids and the therapeutic potential of oligonucleotide-directed triplex formation in the control of gene expression according to the antigene strategy, research in triple helical structure has been considerably stimulated. Thus, in the antigene approach, oligonucleotides are targeted to the unique gene that specifies a disease-related protein and stall transcription by binding to the major groove of the doublestranded DNA target. Articles which contain a good review of this are Thuong & Mine in *Angew. Chem. Int. Ed. Engl. (*1993) 32, pages 666-690 and "Prospects for the Therapeutic Use of Antigene Oligonucleotides", Maher, L. J. (1996) *Cancer Investigation* 14(1), 66-82 each of which are hereby incorporated by reference in their entirety.

A review of the development of the antigene strategies for designing drugs that will bind to selected sites on the nucleic acids (DNA and RNA) is found in an article by J. S. Cohen and M. E. Hogan in *Scientific American,* December 1994, pages 50-55 and in the monograph by Soyfer, V. N. & Potaman, V N. (1996). "Triple- helical nucleic acids", Springer-Verlag, New York.

One of the diseases of interest as an antigene therapeutical target is cancer. The type I insulin-like growth factor receptor (IGF-IR) plays an important role in the maintenance of the malignant phenotype of cancer (Rubin, R. & Baeserga, R. *Lab. Invest.* 73, 311(1995) ). A large number of cancers and cancer-derived cell lines overexpress the IGF-IR (LeRoith, D et al, *Endocr. Rev.* 16, 143(1995)). Antisense expression vectors directed against the IGF-IR have proven effective in suppressing tumor growth of C6 rat glioblastoma (Baeserga, R. et al, *Cancer Res.* 54, 2218(1994)), hamster mesothelioma (Resnicoff, M. et al, *Cancer Immunol. Immunother.* 42, 64(1996)), and rat prostate cancer (Pass, H. et al, *Cancer Res.* 56, 4044(1996)). An antigene molecule expressed in rat C6 glioblastoma cells inhibited IGF-I transcription and tumorigenic potential of the cell (Rininsland, F. et al, *Proc. Natl. Acad. Sci. USA* 94, 5854(1997)). A compound inhibiting the expression of IGF-IR by means of antigene activity would be a medicament for the above described types of cancer.

Antigene drugs can be used to treat the following diseases:

Anti-virus
  HIV (Giovannangeli, C. et al., *Proc. Natl. Acad. Sci. USA*, (1992) 89, 8631-8635)

Anti-cancer
  human multidrug-resistance mdrl gene
  (Morassutti, C. et al., *Antisense Nucleic Acid Drug Dev*, (1999) 9, 261-270)
  human HER-2/neu gene
  (Ebbinghaus, S. W. et al., *Biochemistry*, (1999) 38, 619-628)
  human c-myc gene
  (Catapano, C. V. et al., *Biochemistry*, (2000) 39, 5126-5138)

Of the compounds (1) and the salts thereof of the present invention, preferred compounds include the following:

(1) compounds in which $R^1$ is a hydrogen atom, an aliphatic acyl group, an aromatic acyl group, a methyl group substituted by from 1 to 3 aryl groups, a methyl group substituted by from 1 to 3 aryl groups the aryl ring of which is substituted by a lower alkyl, lower alkoxy, halogen or cyano group, or a silyl group, and salts thereof;

(2) compounds in which $R^1$ is a hydrogen atom, an acetyl group, a benzoyl group, a benzyl group, a p-methoxybenzyl group, a dimethoxytrityl group, a mono-methoxytrityl group or a tert-butyldiphenylsilyl group, and salts thereof;

(3) compounds in which $R^2$ is a hydrogen atom, an aliphatic acyl group, an aromatic acyl group, a methyl group substituted by from 1 to 3 aryl groups, a methyl group substituted by from 1 to 3 aryl groups the aryl ring of which is substituted by a lower alkyl, lower alkoxy, halogen or cyano group, a silyl group, a phosphoramidite group, a phosphonyl group, a phosphate group or a protected phosphate group, and salts thereof;

(4) compounds in which $R^2$ is a hydrogen atom, an acetyl group, a benzoyl group, a benzyl group, a p-methoxybenzyl group, a tert-butyldiphenylsilyl group, —P(OC$_2$H$_4$CN)(NCH(CH$_3$)$_2$), —P(OCH$_3$)(NCH(CH$_3$)$_2$), a phosphonyl group or a 2-chlorophenyl or 4-chlorophenyl phosphate group, and salts thereof;

(5) compounds in which A is a methylene group, and salts thereof;

(6) compounds in which B is a 6-aminopurin-9-yl (i.e., adeninyl), 6-aminopurin-9-yl the amino group of which is protected, 2,6-diaminopurin-9-yl, 2-amino-6-chloropurin-9-yl, 2-amino-6-chloropurin-9-yl the amino group of which is protected, 2-amino-6-fluoropurin-9-yl, 2-amino-6-fluoropurin-9-yl the amino group of which is protected, 2-amino-6-bromopurin-9-yl, 2-amino-6-bromopurin-9-yl the amino group of which is protected, 2-amino-6-hydroxypurin-9-yl (i.e., guaninyl), 2-amino-6-hydroxypurin-9-yl the amino group of which is protected, 2-amino-6-hydroxypurin-9-yl the amino group and hydroxyl group of which are protected, 6-amino-2-methoxypurin-9-yl, 6-amino-2-chloropurin-9-yl, 6-amino-2-fluoropurin-9-yl, 2,6-dimethoxypurin-9-yl, 2,6-dichloropurin-9-yl, 6-mercaptopurin-9-yl, 2-oxo-4-amino-pyrimidin-1-yl (i.e., cytosinyl), 2-oxo-4-amino-pyrimidin-1-yl the amino group of which is protected, 2-oxo-4-amino-5-fluoro-pyrimidin-1-yl, 2-oxo-4-amino-5-fluoro-pyrimidin-1-yl the amino group of which is protected, 4-amino-2-oxo-5-chloro-pyrimidin-1-yl, 2-oxo-4-methoxy-pyrimidin-1-yl, 2-oxo-4-mercapto-pyrimidin-1-yl, 2-oxo-4-hydroxy-pyrimidin-1-yl (i.e., uracinyl), 2-oxo-4-hydroxy-5-methylpyrimidin-1-yl (i.e., thyminyl), 4-amino-5-methyl-2-oxo-pyrimidin-1-yl (i.e., 5-methylcytosinyl) group or 4-amino-5-methyl-2-oxo-pyrimidin-1-yl group the amino of which group is protected, and salts thereof; and (7) compounds in which B is a 6-benzoylaminopurin-9-yl, adeninyl, 2-isobutyrylamino-6-hydroxypurin-9-yl, guaninyl, 2-oxo-4-benzoylamino-pyrimidin-1-yl, cytosinyl, 2-oxo-5-methyl-4-benzoylamino-pyrimidin-1-yl, 5-methylcytosinyl, uracinyl or thyminyl group, and salts thereof.

The above (1) and (2), (3) and (4) or (6) and (7) indicate the more preferred compounds as the number becomes larger and in the formula (1), the compound obtained by optionally selecting $R^1$ from (1) and (2), optionally selecting $R^2$ from (3) and (4), optionally selecting A from (5) and optionally selecting B from (6) and (7) or by optionally combining them and the salts thereof are preferred and the compounds and the salts thereof selected from the following groups are particularly preferred.

Group of compounds:
2'-O,4'-C-ethyleneguanosine,
2'-O,4'-C-ethyleneadenosine,
3',5'-di-O-benzyl-2'-O,4'-C-ethylene-6-N-benzoyladenosine,
3',5'-di-O-benzyl-2'-O,4'-C-ethylene-2-N-isobutyrylguanosine,
5'-O-dimethoxytrityl-2'-O,4'-C-ethylene-6-N-benzoyladenosine,
5'-O-dimethoxytrityl-2'-O,4'-C-ethylene-2-N-isobutyrylguanosine,
2'-O,4'-C-ethylene-2-N-isobutylguanosine,
2'-O,4'-C-ethylene-6-N-benzoyladenosine,
5'-O-dimethoxytrityl-2'-O4'-C-ethylene-6-N-benzoyladenosine-3'-O-(2-cyanoethyl N,N-diisopropyl)phosphoramidite,
5'-O-dimethoxytrityl-2'-O,4'-C-ethylene-2-N-isobutyrlguanosine-3'-O-(2-cyanoethyl N,N-diisopropyl)phosphoramidite,
2'-O,4'-C-ethyleneuridine,
2'-O,4'-C-ethylene-5-methyluridine,
2'-O,4'-C-ethylenecytidine,
2'-O,4'-C-ethylene-5-methylcytidine,
5'-O-dimethoxytrityl-2'-O,4'-C-ethyleneuridine,
3',5'-di-O-benzyl-2'-O,4'-C-ethylene-5-methyluridine,
5'-O-dimethoxytrityl-2'-O,4'-C-ethylene-5-methyluridine,
3',5'-di-O-benzyl-2'-O,4'-C-ethylene-4-N-benzoylcytidine,
5'-O-dimethoxytrityl-2'-O,4'-C-ethylene-4-N-benzoylcytidine,
3',5'-di-O-benzyl-2'-O,4'-C-ethylene-4-N-benzoyl-5-methylcytidine, 5'-O-dimethoxytrityl-2'-O,4'-C-ethylene-4-N-benzoyl-5-methylcytidine,
2'-O,4'-C-ethylene-4-N-benzoylcytidine,
2'-O,4'-C-ethylene-4-N-benzoyl-5-methylcytidine,
5'-O-dimethoxytrityl-2'-O,4'-C-ethylene-5-methylcytidine, 3'-O-(2-cyanoethyl N,N-diisopropyl)phosphoramidite,
5'-O-dimethoxytrityl-2'-O,4'-C-ethylene-4-N-benzoylcytidine-3'-O-(2-cyanoethyl N,N-diisopropyl)phosphoramidite,
5'-O-dimethoxytrityl-2'-O,4'-C-ethylene-5-methylcytidine-3'-O-(2-cyano N,N-diisopropyl)phosphoramidite,
5'-O-dimethyoxytrityl-2'-O,4'-C-ethylene-4-N-benzoyl-5-methylcytidine-3'-O-(2-cyano ethyl N,N-diisopropyl)phosphoramidite.

Of the oligonucleotide analogues containing one or two or more structures of the formula (2) and the salts thereof of the present invention, the preferred compounds may include (8) oligonucleotide analogues in which A is a methylene group, and pharmacologically acceptable salts thereof,
(9) oligonucleotide analogues in which B is a 6-aminopurin-9-yl (i.e., adeninyl), 6-aminopurin-9-yl the amino group of which is protected, 2,6-diaminopurin-9-yl, 2-amino-6-chloropurin-9-yl, 2-amino-6-chloropurin-9-yl the amino group of which is protected, 2-amino-6-fluoropurin-9-yl, 2-amino-6-fluoropurin-9-yl the amino group of which is protected, 2-amino-6-bromopurin-9-yl, 2-amino-6-bromopurin-9-yl the amino group of which is protected, 2-amino-6-hydroxypurin-9-yl (i.e., guaninyl), 2-amino-6-hydroxypurin-9-yl the amino group of which is protected, 2-amino-6-hydroxypurin-9-yl the amino group and hydroxyl group of which are protected, 6-amino-2-methoxypurin-9-yl, 6-amino-2-chloropurin-9-yl, 6-amino-2-fluoropurin-9-yl, 2,6-dimethoxypurin-9-yl, 2,6-dichloropurin-9-yl, 6-mercaptopurin-9-yl, 2-oxo-4-aminopyrimidin-1-yl (i.e., cytosinyl), 2-oxo-4-aminopyrimidin-1-yl the amino group of which is protected, 2-oxo-4-amino-5-fluoro-pyrimidin-1-yl, 2-oxo-4-amino-5-fluoro-pyrimidin-1-yl the amino group of which is protected, 4-amino-2-oxo-5-chloro-pyrimidin-1-yl, 2-oxo-4-methoxy-pyrimidin-1-yl, 2-oxo-4-mercapto-pyrimidin-1-yl, 2-oxo-4-hydroxy-pyrimidin-1-yl (i.e., uracinyl), 2-oxo-4-hydroxy-5-methylpyrimidin-1-yl (i.e., thyminyl), 4-amino-5-methyl-2-oxo-pyrimidin-1-yl (i.e., 5-methylcytosinyl) group or a 4-amino-5-methyl-2-oxo-pyrimidin-1-yl group the amino group of which is protected, and pharmacologically acceptable salts thereof, and

(10) oligonucleotide analogues in which B is a 6-benzoylaminopurin-9-yl, adeninyl, 2-isobutyrylamino-6-hydroxypurin-9-yl, guaninyl, 2-oxo-4-benzoylamino-pyrimidin-1-yl, cytosinyl, 2-oxo-5-methyl-4-benzoylamino-pyrimidin-1-yl, 5-methylcytosinyl, uracinyl or thyminyl group, and pharmacologically acceptable salts thereof.

The above (9) and (10) indicate the more preferred oligonucleotide analogues as the number becomes larger, and in the formula (2), the oligonucleotide analogues obtained by optionally selecting A from (8) and optionally selecting B from (9) and (10) or optionally combining these and the salts thereof are preferred.

The specific compounds included in the compound of the above formula (1) of the present invention are illustrated in Tables 1 and 2. However, the compounds of the present invention are not limited to those.

In Table 1 and Table 2, Exe. com. num. represents Exemplification compound number, Me represents a methyl group, Bn represents a benzyl group, Bz represents a benzoyl group, PMB represents a p-methoxybenzyl group, Tr represents a triphenylmethyl group, MMTr represents a 4-methoxytriphenylmethyl (monomethoxytrityl) group, DMTr represents a 4,4'-dimethoxytriphenylmethyl (dimethoxytrityl) group, TMTr represents a 4,4',4"-trimethoxytriphenylmethyl (trimethoxytrityl) group, TMS represents a trimethylsilyl group, TBDMS represents a tert-butyldimethylsilyl group, TBDPS represents a tert-butyldiphenylsilyl group and TIPS represents a triisopropylsilyl group.

TABLE 1

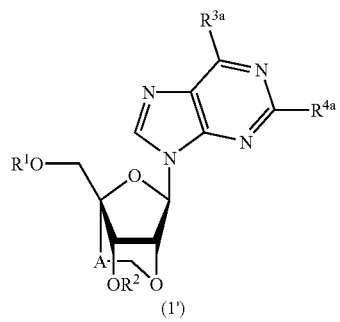

(1')

| Exe. com. num. | A | $R^1$ | $R^2$ | $R^{3a}$ | $R^{4a}$ |
|---|---|---|---|---|---|
| 1-1 | $CH_2$ | H | H | H | H |
| 1-2 | $CH_2$ | H | H | H | $NH_2$ |
| 1-3 | $CH_2$ | H | H | H | OH |
| 1-4 | $CH_2$ | H | H | OH | H |
| 1-5 | $CH_2$ | H | H | OH | $NH_2$ |
| 1-6 | $CH_2$ | H | H | OH | OH |
| 1-7 | $CH_2$ | H | H | $NH_2$ | H |
| 1-8 | $CH_2$ | H | H | $NH_2$ | $NH_2$ |
| 1-9 | $CH_2$ | H | H | $NH_2$ | Cl |
| 1-10 | $CH_2$ | H | H | $NH_2$ | F |
| 1-11 | $CH_2$ | H | H | $NH_2$ | Br |
| 1-12 | $CH_2$ | H | H | $NH_2$ | OH |

TABLE 1-continued

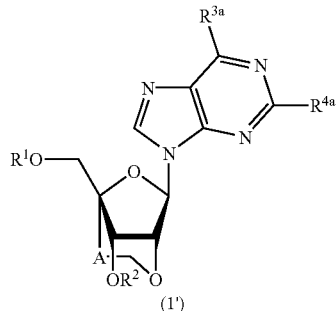

(1')

| Exe. com. num. | A | $R^1$ | $R^2$ | $R^{3a}$ | $R^{4a}$ |
|---|---|---|---|---|---|
| 1-13 | $CH_2$ | H | H | OMe | H |
| 1-14 | $CH_2$ | H | H | OMe | OMe |
| 1-15 | $CH_2$ | H | H | OMe | $NH_2$ |
| 1-16 | $CH_2$ | H | H | Cl | H |
| 1-17 | $CH_2$ | H | H | Br | H |
| 1-18 | $CH_2$ | H | H | F | H |
| 1-19 | $CH_2$ | H | H | Cl | Cl |
| 1-20 | $CH_2$ | H | H | SH | H |
| 1-21 | $CH_2$ | Bn | H | NHBz | H |
| 1-22 | $CH_2$ | Bn | H | OH | $NHCOCH(CH_3)_2$ |
| 1-23 | $CH_2$ | Bn | Bn | NHBz | H |
| 1-24 | $CH_2$ | Bn | Bn | OH | $NHCOCH(CH_3)_2$ |
| 1-25 | $CH_2$ | PMB | H | NHBz | H |
| 1-26 | $CH_2$ | PMB | H | OH | $NHCOCH(CH_3)_2$ |
| 1-27 | $CH_2$ | PMB | PMB | NHBz | H |
| 1-28 | $CH_2$ | PMB | PMB | OH | $NHCOCH(CH_3)_2$ |
| 1-29 | $CH_2$ | Tr | H | NHBz | H |
| 1-30 | $CH_2$ | MMTr | H | NHBz | H |
| 1-31 | $CH_2$ | DMTr | H | NHBz | H |
| 1-32 | $CH_2$ | TMTr | H | NHBz | H |
| 1-33 | $CH_2$ | Tr | H | OH | $NHCOCH(CH_3)_2$ |
| 1-34 | $CH_2$ | MMTr | H | OH | $NHCOCH(CH_3)_2$ |
| 1-35 | $CH_2$ | DMTr | H | OH | $NHCOCH(CH_3)_2$ |
| 1-36 | $CH_2$ | TMTr | H | OH | $NHCOCH(CH_3)_2$ |
| 1-37 | $CH_2$ | TMS | H | NHBz | H |
| 1-38 | $CH_2$ | TBDMS | H | NHBz | H |
| 1-39 | $CH_2$ | TBDPS | H | NHBz | H |
| 1-40 | $CH_2$ | TIPS | H | NHBz | H |
| 1-41 | $CH_2$ | TMS | H | OH | $NHCOCH(CH_3)_2$ |
| 1-42 | $CH_2$ | TBDMS | H | OH | $NHCOCH(CH_3)_2$ |
| 1-43 | $CH_2$ | TBDPS | H | OH | $NHCOCH(CH_3)_2$ |
| 1-44 | $CH_2$ | TIPS | H | OH | $NHCOCH(CH_3)_2$ |
| 1-45 | $(CH_2)_2$ | H | H | H | H |
| 1-46 | $(CH_2)_2$ | H | H | H | $NH_2$ |
| 1-47 | $(CH_2)_2$ | H | H | H | OH |
| 1-48 | $(CH_2)_2$ | H | H | OH | H |
| 1-49 | $(CH_2)_2$ | H | H | OH | $NH_2$ |
| 1-50 | $(CH_2)_2$ | H | H | OH | OH |
| 1-51 | $(CH_2)_2$ | H | H | $NH_2$ | H |
| 1-52 | $(CH_2)_2$ | H | H | $NH_2$ | $NH_2$ |
| 1-53 | $(CH_2)_2$ | H | H | $NH_2$ | Cl |
| 1-54 | $(CH_2)_2$ | H | H | $NH_2$ | F |
| 1-55 | $(CH_2)_2$ | H | H | $NH_2$ | Br |
| 1-56 | $(CH_2)_2$ | H | H | $NH_2$ | OH |
| 1-57 | $(CH_2)_2$ | H | H | OMe | H |
| 1-58 | $(CH_2)_2$ | H | H | OMe | OMe |
| 1-59 | $(CH_2)_2$ | H | H | OMe | $NH_2$ |
| 1-60 | $(CH_2)_2$ | H | H | Cl | H |
| 1-61 | $(CH_2)_2$ | H | H | Br | H |
| 1-62 | $(CH_2)_2$ | H | H | F | H |
| 1-63 | $(CH_2)_2$ | H | H | Cl | Cl |
| 1-64 | $(CH_2)_2$ | H | H | SH | H |
| 1-65 | $(CH_2)_2$ | Bn | H | NHBz | H |
| 1-66 | $(CH_2)_2$ | Bn | H | OH | $NHCOCH(CH_3)_2$ |
| 1-67 | $(CH_2)_2$ | Bn | Bn | NHBz | H |
| 1-68 | $(CH_2)_2$ | Bn | Bn | OH | $NHCOCH(CH_3)_2$ |
| 1-69 | $(CH_2)_2$ | PMB | H | NHBz | H |
| 1-70 | $(CH_2)_2$ | PMB | H | OH | $NHCOCH(CH_3)_2$ |
| 1-71 | $(CH_2)_2$ | PMB | PMB | NHBz | H |
| 1-72 | $(CH_2)_2$ | PMB | PMB | OH | $NHCOCH(CH_3)_2$ |

TABLE 1-continued

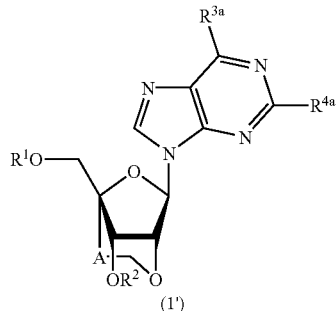

(1')

| Exe. com. num. | A | $R^1$ | $R^2$ | $R^{3a}$ | $R^{4a}$ |
|---|---|---|---|---|---|
| 1-73 | $(CH_2)_2$ | Tr | H | NHBz | H |
| 1-74 | $(CH_2)_2$ | MMTr | H | NHBz | H |
| 1-75 | $(CH_2)_2$ | DMTr | H | NHBz | H |
| 1-76 | $(CH_2)_2$ | TMTr | H | NHBz | H |
| 1-77 | $(CH_2)_2$ | Tr | H | OH | $NHCOCH(CH_3)_2$ |
| 1-78 | $(CH_2)_2$ | MMTr | H | OH | $NHCOCH(CH_3)_2$ |
| 1-79 | $(CH_2)_2$ | DMTr | H | OH | $NHCOCH(CH_3)_2$ |
| 1-80 | $(CH_2)_2$ | TMTr | H | OH | $NHCOCH(CH_3)_2$ |
| 1-81 | $(CH_2)_2$ | TMS | H | NHBz | H |
| 1-82 | $(CH_2)_2$ | TBDMS | H | NHBz | H |
| 1-83 | $(CH_2)_2$ | TBDPS | H | NHBz | H |
| 1-84 | $(CH_2)_2$ | TIPS | H | NHBz | H |
| 1-85 | $(CH_2)_2$ | TMS | H | OH | $NHCOCH(CH_3)_2$ |
| 1-86 | $(CH_2)_2$ | TBDMS | H | OH | $NHCOCH(CH_3)_2$ |
| 1-87 | $(CH_2)_2$ | TBDPS | H | OH | $NHCOCH(CH_3)_2$ |
| 1-88 | $(CH_2)_2$ | TIPS | H | OH | $NHCOCH(CH_3)_2$ |
| 1-89 | $(CH_2)_3$ | H | H | H | H |
| 1-90 | $(CH_2)_3$ | H | H | H | $NH_2$ |
| 1-91 | $(CH_2)_3$ | H | H | H | OH |
| 1-92 | $(CH_2)_3$ | H | H | OH | H |
| 1-93 | $(CH_2)_3$ | H | H | OH | $NH_2$ |
| 1-94 | $(CH_2)_3$ | H | H | OH | OH |
| 1-95 | $(CH_2)_3$ | H | H | $NH_2$ | H |
| 1-96 | $(CH_2)_3$ | H | H | $NH_2$ | $NH_2$ |
| 1-97 | $(CH_2)_3$ | H | H | $NH_2$ | Cl |
| 1-98 | $(CH_2)_3$ | H | H | $NH_2$ | F |
| 1-99 | $(CH_2)_3$ | H | H | $NH_2$ | Br |
| 1-100 | $(CH_2)_3$ | H | H | $NH_2$ | OH |
| 1-101 | $(CH_2)_3$ | H | H | OMe | H |
| 1-102 | $(CH_2)_3$ | H | H | OMe | OMe |
| 1-103 | $(CH_2)_3$ | H | H | OMe | $NH_2$ |
| 1-104 | $(CH_2)_3$ | H | H | Cl | H |
| 1-105 | $(CH_2)_3$ | H | H | Br | H |
| 1-106 | $(CH_2)_3$ | H | H | F | H |
| 1-107 | $(CH_2)_3$ | H | H | Cl | Cl |
| 1-108 | $(CH_2)_3$ | H | H | SH | H |
| 1-109 | $(CH_2)_3$ | Bn | H | NHBz | H |
| 1-110 | $(CH_2)_3$ | Bn | H | OH | $NHCOCH(CH_3)_2$ |
| 1-111 | $(CH_2)_3$ | Bn | Bn | NHBz | H |
| 1-112 | $(CH_2)_3$ | Bn | Bn | OH | $NHCOCH(CH_3)_2$ |
| 1-113 | $(CH_2)_3$ | PMB | H | NHBz | H |
| 1-114 | $(CH_2)_3$ | PMB | H | OH | $NHCOCH(CH_3)_2$ |
| 1-115 | $(CH_2)_3$ | PMB | PMB | NHBz | H |
| 1-116 | $(CH_2)_3$ | PMB | PMB | OH | $NHCOCH(CH_3)_2$ |
| 1-117 | $(CH_2)_3$ | Tr | H | NHBz | H |
| 1-118 | $(CH_2)_3$ | MMTr | H | NHBz | H |
| 1-119 | $(CH_2)_3$ | DMTr | H | NHBz | H |
| 1-120 | $(CH_2)_3$ | TMTr | H | NHBz | H |
| 1-121 | $(CH_2)_3$ | Tr | H | OH | $NHCOCH(CH_3)_2$ |
| 1-122 | $(CH_2)_3$ | MMTr | H | OH | $NHCOCH(CH_3)_2$ |
| 1-123 | $(CH_2)_3$ | DMTr | H | OH | $NHCOCH(CH_3)_2$ |
| 1-124 | $(CH_2)_3$ | TMTr | H | OH | $NHCOCH(CH_3)_2$ |
| 1-125 | $(CH_2)_3$ | TMS | H | NHBz | H |
| 1-126 | $(CH_2)_3$ | TBDMS | H | NHBz | H |
| 1-127 | $(CH_2)_3$ | TBDPS | H | NHBz | H |
| 1-128 | $(CH_2)_3$ | TIPS | H | NHBz | H |
| 1-129 | $(CH_2)_3$ | TMS | H | OH | $NHCOCH(CH_3)_2$ |
| 1-130 | $(CH_2)_3$ | TBDMS | H | OH | $NHCOCH(CH_3)_2$ |
| 1-131 | $(CH_2)_3$ | TBDPS | H | OH | $NHCOCH(CH_3)_2$ |
| 1-132 | $(CH_2)_3$ | TIPS | H | OH | $NHCOCH(CH_3)_2$ |

TABLE 1-continued

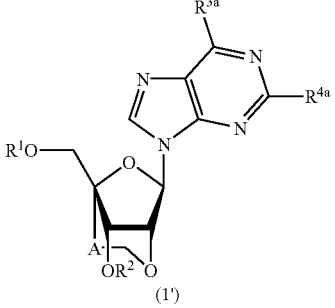
(1')

| Exe. com. num. | A | $R^1$ | $R^2$ | $R^{3a}$ | $R^{4a}$ |
|---|---|---|---|---|---|
| 1-133 | $(CH_2)_4$ | H | H | H | H |
| 1-134 | $(CH_2)_4$ | H | H | H | $NH_2$ |
| 1-135 | $(CH_2)_4$ | H | H | H | OH |
| 1-136 | $(CH_2)_4$ | H | H | OH | H |
| 1-137 | $(CH_2)_4$ | H | H | OH | $NH_2$ |
| 1-138 | $(CH_2)_4$ | H | H | OH | OH |
| 1-139 | $(CH_2)_4$ | H | H | $NH_2$ | H |
| 1-140 | $(CH_2)_4$ | H | H | $NH_2$ | $NH_2$ |
| 1-141 | $(CH_2)_4$ | H | H | $NH_2$ | Cl |
| 1-142 | $(CH_2)_4$ | H | H | $NH_2$ | F |
| 1-143 | $(CH_2)_4$ | H | H | $NH_2$ | Br |
| 1-144 | $(CH_2)_4$ | H | H | $NH_2$ | OH |
| 1-145 | $(CH_2)_4$ | H | H | OMe | H |
| 1-146 | $(CH_2)_4$ | H | H | OMe | OMe |
| 1-147 | $(CH_2)_4$ | H | H | OMe | $NH_2$ |
| 1-148 | $(CH_2)_4$ | H | H | Cl | H |
| 1-149 | $(CH_2)_4$ | H | H | Br | H |
| 1-150 | $(CH_2)_4$ | H | H | F | H |
| 1-151 | $(CH_2)_4$ | H | H | Cl | Cl |
| 1-152 | $(CH_2)_4$ | H | H | SH | H |
| 1-153 | $(CH_2)_4$ | Bn | H | NHBz | H |
| 1-154 | $(CH_2)_4$ | Bn | H | OH | $NHCOCH(CH_3)_2$ |
| 1-155 | $(CH_2)_4$ | Bn | Bn | NHBz | H |
| 1-156 | $(CH_2)_4$ | Bn | Bn | OH | $NHCOCH(CH_3)_2$ |
| 1-157 | $(CH_2)_4$ | PMB | H | NHBz | H |
| 1-158 | $(CH_2)_4$ | PMB | H | OH | $NHCOCH(CH_3)_2$ |
| 1-159 | $(CH_2)_4$ | PMB | PMB | NHBz | H |
| 1-160 | $(CH_2)_4$ | PMB | PMB | OH | $NHCOCH(CH_3)_2$ |
| 1-161 | $(CH_2)_4$ | Tr | H | NHBz | H |
| 1-162 | $(CH_2)_4$ | MMTr | H | NHBz | H |
| 1-163 | $(CH_2)_4$ | DMTr | H | NHBz | H |
| 1-164 | $(CH_2)_4$ | TMTr | H | NHBz | H |
| 1-165 | $(CH_2)_4$ | Tr | H | OH | $NHCOCH(CH_3)_2$ |
| 1-166 | $(CH_2)_4$ | MMTr | H | OH | $NHCOCH(CH_3)_2$ |
| 1-167 | $(CH_2)_4$ | DMTr | H | OH | $NHCOCH(CH_3)_2$ |
| 1-168 | $(CH_2)_4$ | TMTr | H | OH | $NHCOCH(CH_3)_2$ |
| 1-169 | $(CH_2)_4$ | TMS | H | NHBz | H |
| 1-170 | $(CH_2)_4$ | TBDMS | H | NHBz | H |
| 1-171 | $(CH_2)_4$ | TBDPS | H | NHBz | H |
| 1-172 | $(CH_2)_4$ | TIPS | H | NHBz | H |
| 1-173 | $(CH_2)_4$ | TMS | H | OH | $NHCOCH(CH_3)_2$ |
| 1-174 | $(CH_2)_4$ | TBDMS | H | OH | $NHCOCH(CH_3)_2$ |
| 1-175 | $(CH_2)_4$ | TBDPS | H | OH | $NHCOCH(CH_3)_2$ |
| 1-176 | $(CH_2)_4$ | TIPS | H | OH | $NHCOCH(CH_3)_2$ |
| 1-177 | $CH_2$ | H | H | OH | $NHCOCH(CH_3)_2$ |
| 1-178 | $CH_2$ | H | H | NHBz | H |
| 1-179 | $(CH_2)_2$ | H | H | OH | $NHCOCH(CH_3)_2$ |
| 1-180 | $(CH_2)_2$ | H | H | NHBz | H |
| 1-181 | $(CH_2)_3$ | H | H | OH | $NHCOCH(CH_3)_2$ |
| 1-182 | $(CH_2)_3$ | H | H | NHBz | H |
| 1-183 | $(CH_2)_4$ | H | H | OH | $NHCOCH(CH_3)_2$ |
| 1-184 | $(CH_2)_4$ | H | H | NHBz | H |
| 1-185 | $CH_2$ | DMTr | $P(N(iPr)_2)(OC_2H_4CN)$ | OH | $NHCOCH(CH_3)_2$ |
| 1-186 | $CH_2$ | DMTr | $P(N(iPr)_2)(OC_2H_4CN)$ | NHBz | H |
| 1-187 | $(CH_2)_2$ | DMTr | $P(N(iPr)_2)(OC_2H_4CN)$ | OH | $NHCOCH(CH_3)_2$ |
| 1-188 | $(CH_2)_2$ | DMTr | $P(N(iPr)_2)(OC_2H_4CN)$ | NHBz | H |
| 1-189 | $(CH_2)_3$ | DMTr | $P(N(iPr)_2)(OC_2H_4CN)$ | OH | $NHCOCH(CH_3)_2$ |
| 1-190 | $(CH_2)_3$ | DMTr | $P(N(iPr)_2)(OC_2H_4CN)$ | NHBz | H |
| 1-191 | $(CH_2)_4$ | DMTr | $P(N(iPr)_2)(OC_2H_4CN)$ | OH | $NHCOCH(CH_3)_2$ |
| 1-192 | $(CH_2)_4$ | DMTr | $P(N(iPr)_2)(OC_2H_4CN)$ | NHBz | H |

TABLE 1-continued

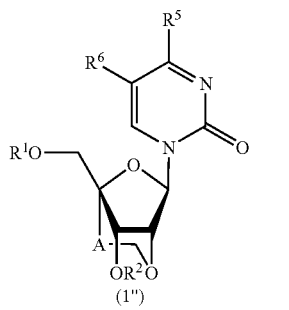

(1')

| Exe. com. num. | A | R¹ | R² | R³ᵃ | R⁴ᵃ |
|---|---|---|---|---|---|
| 1-193 | CH₂ | DMTr | P(N(iPr)₂)(OCH₃) | OH | NHCOCH(CH₃)₂ |
| 1-194 | CH₂ | DMTr | P(N(iPr)₂)(OCH₃) | NHBz | H |
| 1-195 | (CH₂)₂ | DMTr | P(N(iPr)₂)(OCH₃) | OH | NHCOCH(CH₃)₂ |
| 1-196 | (CH₂)₂ | DMTr | P(N(iPr)₂)(OCH₃) | NHBz | H |
| 1-197 | (CH₂)₃ | DMTr | P(N(iPr)₂)(OCH₃) | OH | NHCOCH(CH₃)₂ |
| 1-198 | (CH₂)₃ | DMTr | P(N(iPr)₂)(OCH₃) | NHBz | H |
| 1-199 | (CH₂)₄ | DMTr | P(N(iPr)₂)(OCH₃) | OH | NHCOCH(CH₃)₂ |
| 1-200 | (CH₂)₄ | DMTr | P(N(iPr)₂)(OCH₃) | NHBz | H |
| 1-201 | CH₂ | DMTr | P(O)(OH)H | OH | NHCOCH(CH₃)₂ |
| 1-202 | CH₂ | DMTr | P(O)(OH)H | NHBz | H |
| 1-203 | (CH₂)₂ | DMTr | P(O)(OH)H | OH | NHCOCH(CH₃)₂ |
| 1-204 | (CH₂)₂ | DMTr | P(O)(OH)H | NHBz | H |
| 1-205 | (CH₂)₃ | DMTr | P(O)(OH)H | OH | NHCOCH(CH₃)₂ |
| 1-206 | (CH₂)₃ | DMTr | P(O)(OH)H | NHBz | H |
| 1-207 | (CH₂)₄ | DMTr | P(O)(OH)H | OH | NHCOCH(CH₃)₂ |
| 1-208 | (CH₂)₄ | DMTr | P(O)(OH)H | NHBz | H |

TABLE 2

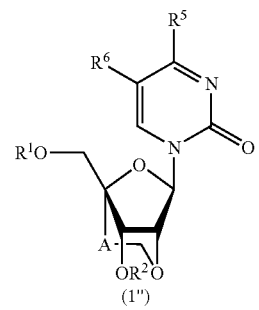

(1")

| Exe. com. num. | A | R¹ | R² | R⁵ | R⁶ |
|---|---|---|---|---|---|
| 2-1 | CH₂ | H | H | OH | H |
| 2-2 | CH₂ | H | H | OH | CH₃ |
| 2-3 | CH₂ | H | H | NH₂ | H |
| 2-4 | CH₂ | H | H | NH₂ | CH₃ |
| 2-5 | CH₂ | H | H | NH₂ | F |
| 2-6 | CH₂ | H | H | Cl | H |
| 2-7 | CH₂ | H | H | OMe | H |
| 2-8 | CH₂ | H | H | SH | H |
| 2-9 | CH₂ | Bn | H | OH | H |
| 2-10 | CH₂ | Bn | Bn | OH | H |
| 2-11 | CH₂ | PMB | H | OH | H |
| 2-12 | CH₂ | PMB | PMB | OH | H |
| 2-13 | CH₂ | Tr | H | OH | H |
| 2-14 | CH₂ | MMTr | H | OH | H |
| 2-15 | CH₂ | DMTr | H | OH | H |
| 2-16 | CH₂ | TMTr | H | OH | H |
| 2-17 | CH₂ | TMS | H | OH | H |
| 2-18 | CH₂ | TBDMS | H | OH | H |
| 2-19 | CH₂ | TBDPS | H | OH | H |
| 2-20 | CH₂ | TIPS | H | OH | H |
| 2-21 | CH₂ | Bn | H | OH | CH₃ |
| 2-22 | CH₂ | Bn | Bn | OH | CH₃ |
| 2-23 | CH₂ | PMB | H | OH | CH₃ |
| 2-24 | CH₂ | PMB | PMB | OH | CH₃ |
| 2-25 | CH₂ | Tr | H | OH | CH₃ |
| 2-26 | CH₂ | MMTr | H | OH | CH₃ |
| 2-27 | CH₂ | DMTr | H | OH | CH₃ |
| 2-28 | CH₂ | TMTr | H | OH | CH₃ |
| 2-29 | CH₂ | TMS | H | OH | CH₃ |
| 2-30 | CH₂ | TBDMS | H | OH | CH₃ |
| 2-31 | CH₂ | TBDPS | H | OH | CH₃ |
| 2-32 | CH₂ | TIPS | H | OH | CH₃ |
| 2-33 | CH₂ | Bn | H | NHBz | H |
| 2-34 | CH₂ | Bn | Bn | NHBz | H |
| 2-35 | CH₂ | PMB | H | NHBz | H |
| 2-36 | CH₂ | PMB | PMB | NHBz | H |
| 2-37 | CH₂ | Tr | H | NHBz | H |
| 2-38 | CH₂ | MMTr | H | NHBz | H |

TABLE 2-continued (1")

| Exe. com. num. | A | R¹ | R² | R⁵ | R⁶ |
|---|---|---|---|---|---|
| 2-39 | CH₂ | DMTr | H | NHBz | H |
| 2-40 | CH₂ | TMTr | H | NHBz | H |
| 2-41 | CH₂ | TMS | H | NHBz | H |
| 2-42 | CH₂ | TBDMS | H | NHBz | H |
| 2-43 | CH₂ | TBDPS | H | NHBz | H |
| 2-44 | CH₂ | TIPS | H | NHBz | H |
| 2-45 | CH₂ | Bn | H | NHBz | CH₃ |
| 2-46 | CH₂ | Bn | Bn | NHBz | CH₃ |
| 2-47 | CH₂ | PMB | H | NHBz | CH₃ |
| 2-48 | CH₂ | PMB | PMB | NHBz | CH₃ |
| 2-49 | CH₂ | Tr | H | NHBz | CH₃ |
| 2-50 | CH₂ | MMTr | H | NHBz | CH₃ |
| 2-51 | CH₂ | DMTr | H | NHBz | CH₃ |
| 2-52 | CH₂ | TMTr | H | NHBz | CH₃ |
| 2-53 | CH₂ | TMS | H | NHBz | CH₃ |
| 2-54 | CH₂ | TBDMS | H | NHBz | CH₃ |
| 2-55 | CH₂ | TBDPS | H | NHBz | CH₃ |
| 2-56 | CH₂ | TIPS | H | NHBz | CH₃ |
| 2-57 | (CH₂)₂ | H | H | OH | H |
| 2-58 | (CH₂)₂ | H | H | OH | CH₃ |
| 2-59 | (CH₂)₂ | H | H | NH₂ | H |
| 2-60 | (CH₂)₂ | H | H | NH₂ | CH₃ |
| 2-61 | (CH₂)₂ | H | H | NH₂ | F |
| 2-62 | (CH₂)₂ | H | H | Cl | H |
| 2-63 | (CH₂)₂ | H | H | OMe | H |
| 2-64 | (CH₂)₂ | H | H | SH | H |
| 2-65 | (CH₂)₂ | Bn | H | OH | H |
| 2-66 | (CH₂)₂ | Bn | Bn | OH | H |
| 2-67 | (CH₂)₂ | PMB | H | OH | H |
| 2-68 | (CH₂)₂ | PMB | PMB | OH | H |
| 2-69 | (CH₂)₂ | Tr | H | OH | H |
| 2-70 | (CH₂)₂ | MMTr | H | OH | H |
| 2-71 | (CH₂)₂ | DMTr | H | OH | H |
| 2-72 | (CH₂)₂ | TMTr | H | OH | H |
| 2-73 | (CH₂)₂ | TMS | H | OH | H |
| 2-74 | (CH₂)₂ | TBDMS | H | OH | H |
| 2-75 | (CH₂)₂ | TBDPS | H | OH | H |
| 2-76 | (CH₂)₂ | TIPS | H | OH | H |
| 2-77 | (CH₂)₂ | Bn | H | OH | CH₃ |
| 2-78 | (CH₂)₂ | Bn | Bn | OH | CH₃ |
| 2-79 | (CH₂)₂ | PMB | H | OH | CH₃ |
| 2-80 | (CH₂)₂ | PMB | PMB | OH | CH₃ |
| 2-81 | (CH₂)₂ | Tr | H | OH | CH₃ |
| 2-82 | (CH₂)₂ | MMTr | H | OH | CH₃ |
| 2-83 | (CH₂)₂ | DMTr | H | OH | CH₃ |
| 2-84 | (CH₂)₂ | TMTr | H | OH | CH₃ |
| 2-85 | (CH₂)₂ | TMS | H | OH | CH₃ |
| 2-86 | (CH₂)₂ | TBDMS | H | OH | CH₃ |
| 2-87 | (CH₂)₂ | TBDPS | H | OH | CH₃ |
| 2-88 | (CH₂)₂ | TIPS | H | OH | CH₃ |
| 2-89 | (CH₂)₂ | Bn | H | NHBz | H |
| 2-90 | (CH₂)₂ | Bn | Bn | NHBz | H |
| 2-91 | (CH₂)₂ | PMB | H | NHBz | H |
| 2-92 | (CH₂)₂ | PMB | PMB | NHBz | H |
| 2-93 | (CH₂)₂ | Tr | H | NHBz | H |
| 2-94 | (CH₂)₂ | MMTr | H | NHBz | H |
| 2-95 | (CH₂)₂ | DMTr | H | NHBz | H |
| 2-96 | (CH₂)₂ | TMTr | H | NHBz | H |
| 2-97 | (CH₂)₂ | TMS | H | NHBz | H |
| 2-98 | (CH₂)₂ | TBDMS | H | NHBz | H |
| 2-99 | (CH₂)₂ | TBDPS | H | NHBz | H |
| 2-100 | (CH₂)₂ | TIPS | H | NHBz | H |
| 2-101 | (CH₂)₂ | Bn | H | NHBz | CH₃ |
| 2-102 | (CH₂)₂ | Bn | Bn | NHBz | CH₃ |
| 2-103 | (CH₂)₂ | PMB | H | NHBz | CH₃ |
| 2-104 | (CH₂)₂ | PMB | PMB | NHBz | CH₃ |
| 2-105 | (CH₂)₂ | Tr | H | NHBz | CH₃ |
| 2-106 | (CH₂)₂ | MMTr | H | NHBz | CH₃ |
| 2-107 | (CH₂)₂ | DMTr | H | NHBz | CH₃ |
| 2-108 | (CH₂)₂ | TMTr | H | NHBz | CH₃ |
| 2-109 | (CH₂)₂ | TMS | H | NHBz | CH₃ |
| 2-110 | (CH₂)₂ | TBDMS | H | NHBz | CH₃ |
| 2-111 | (CH₂)₂ | TBDPS | H | NHBz | CH₃ |
| 2-112 | (CH₂)₂ | TIPS | H | NHBz | CH₃ |
| 2-113 | (CH₂)₃ | H | H | OH | H |
| 2-114 | (CH₂)₃ | H | H | OH | CH₃ |
| 2-115 | (CH₂)₃ | H | H | NH₂ | H |
| 2-116 | (CH₂)₃ | H | H | NH₂ | CH₃ |
| 2-117 | (CH₂)₃ | H | H | NH₂ | F |
| 2-118 | (CH₂)₃ | H | H | Cl | H |
| 2-119 | (CH₂)₃ | H | H | OMe | H |
| 2-120 | (CH₂)₃ | H | H | SH | H |
| 2-121 | (CH₂)₃ | Bn | H | OH | H |
| 2-122 | (CH₂)₃ | Bn | Bn | OH | H |
| 2-123 | (CH₂)₃ | PMB | H | OH | H |
| 2-124 | (CH₂)₃ | PMB | PMB | OH | H |
| 2-125 | (CH₂)₃ | Tr | H | OH | H |
| 2-126 | (CH₂)₃ | MMTr | H | OH | H |
| 2-127 | (CH₂)₃ | DMTr | H | OH | H |
| 2-128 | (CH₂)₃ | TMTr | H | OH | H |
| 2-129 | (CH₂)₃ | TMS | H | OH | H |
| 2-130 | (CH₂)₃ | TBDMS | H | OH | H |
| 2-131 | (CH₂)₃ | TBDPS | H | OH | H |
| 2-132 | (CH₂)₃ | TIPS | H | OH | H |
| 2-133 | (CH₂)₃ | Bn | H | OH | CH₃ |
| 2-134 | (CH₂)₃ | Bn | Bn | OH | CH₃ |
| 2-135 | (CH₂)₃ | PMB | H | OH | CH₃ |
| 2-136 | (CH₂)₃ | PMB | PMB | OH | CH₃ |
| 2-137 | (CH₂)₃ | Tr | H | OH | CH₃ |
| 2-138 | (CH₂)₃ | MMTr | H | OH | CH₃ |
| 2-139 | (CH₂)₃ | DMTr | H | OH | CH₃ |
| 2-140 | (CH₂)₃ | TMTr | H | OH | CH₃ |
| 2-141 | (CH₂)₃ | TMS | H | OH | CH₃ |
| 2-142 | (CH₂)₃ | TBDMS | H | OH | CH₃ |
| 2-143 | (CH₂)₃ | TBDPS | H | OH | CH₃ |
| 2-144 | (CH₂)₃ | TIPS | H | OH | CH₃ |
| 2-145 | (CH₂)₃ | Bn | H | NHBz | H |
| 2-146 | (CH₂)₃ | Bn | Bn | NHBz | H |
| 2-147 | (CH₂)₃ | PMB | H | NHBz | H |
| 2-148 | (CH₂)₃ | PMB | PMB | NHBz | H |
| 2-149 | (CH₂)₃ | Tr | H | NHBz | H |
| 2-150 | (CH₂)₃ | MMTr | H | NHBz | H |
| 2-151 | (CH₂)₃ | DMTr | H | NHBz | H |
| 2-152 | (CH₂)₃ | TMTr | H | NHBz | H |
| 2-153 | (CH₂)₃ | TMS | H | NHBz | H |
| 2-154 | (CH₂)₃ | TBDMS | H | NHBz | H |
| 2-155 | (CH₂)₃ | TBDPS | H | NHBz | H |
| 2-156 | (CH₂)₃ | TIPS | H | NHBz | H |
| 2-157 | (CH₂)₃ | Bn | H | NHBz | CH₃ |
| 2-158 | (CH₂)₃ | Bn | Bn | NHBz | CH₃ |

TABLE 2-continued

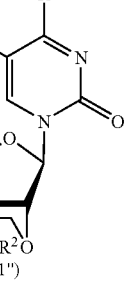

(1")

| Exe. com. num. | A | $R^1$ | $R^2$ | $R^5$ | $R^6$ |
|---|---|---|---|---|---|
| 2-159 | $(CH_2)_3$ | PMB | H | NHBz | $CH_3$ |
| 2-160 | $(CH_2)_3$ | PMB | PMB | NHBz | $CH_3$ |
| 2-161 | $(CH_2)_3$ | Tr | H | NHBz | $CH_3$ |
| 2-162 | $(CH_2)_3$ | MMTr | H | NHBz | $CH_3$ |
| 2-163 | $(CH_2)_3$ | DMTr | H | NHBz | $CH_3$ |
| 2-164 | $(CH_2)_3$ | TMTr | H | NHBz | $CH_3$ |
| 2-165 | $(CH_2)_3$ | TMS | H | NHBz | $CH_3$ |
| 2-166 | $(CH_2)_3$ | TBDMS | H | NHBz | $CH_3$ |
| 2-167 | $(CH_2)_3$ | TBDPS | H | NHBz | $CH_3$ |
| 2-168 | $(CH_2)_3$ | TIPS | H | NHBz | $CH_3$ |
| 2-169 | $(CH_2)_4$ | H | H | OH | H |
| 2-170 | $(CH_2)_4$ | H | H | OH | $CH_3$ |
| 2-171 | $(CH_2)_4$ | H | H | $NH_2$ | H |
| 2-172 | $(CH_2)_4$ | H | H | $NH_2$ | $CH_3$ |
| 2-173 | $(CH_2)_4$ | H | H | $NH_2$ | F |
| 2-174 | $(CH_2)_4$ | H | H | Cl | H |
| 2-175 | $(CH_2)_4$ | H | H | OMe | H |
| 2-176 | $(CH_2)_4$ | H | H | SH | H |
| 2-177 | $(CH_2)_4$ | Bn | H | OH | H |
| 2-178 | $(CH_2)_4$ | Bn | Bn | OH | H |
| 2-179 | $(CH_2)_4$ | PMB | H | OH | H |
| 2-180 | $(CH_2)_4$ | PMB | PMB | OH | H |
| 2-181 | $(CH_2)_4$ | Tr | H | OH | H |
| 2-182 | $(CH_2)_4$ | MMTr | H | OH | H |
| 2-183 | $(CH_2)_4$ | DMTr | H | OH | H |
| 2-184 | $(CH_2)_4$ | TMTr | H | OH | H |
| 2-185 | $(CH_2)_4$ | TMS | H | OH | H |
| 2-186 | $(CH_2)_4$ | TBDMS | H | OH | H |
| 2-187 | $(CH_2)_4$ | TBDPS | H | OH | H |
| 2-188 | $(CH_2)_4$ | TIPS | H | OH | H |
| 2-189 | $(CH_2)_4$ | Bn | H | OH | $CH_3$ |
| 2-190 | $(CH_2)_4$ | Bn | Bn | OH | $CH_3$ |
| 2-191 | $(CH_2)_4$ | PMB | H | OH | $CH_3$ |
| 2-192 | $(CH_2)_4$ | PMB | PMB | OH | $CH_3$ |
| 2-193 | $(CH_2)_4$ | Tr | H | OH | $CH_3$ |
| 2-194 | $(CH_2)_4$ | MMTr | H | OH | $CH_3$ |
| 2-195 | $(CH_2)_4$ | DMTr | H | OH | $CH_3$ |
| 2-196 | $(CH_2)_4$ | TMTr | H | OH | $CH_3$ |
| 2-197 | $(CH_2)_4$ | TMS | H | OH | $CH_3$ |
| 2-198 | $(CH_2)_4$ | TBDMS | H | OH | $CH_3$ |
| 2-199 | $(CH_2)_4$ | TBDPS | H | OH | $CH_3$ |
| 2-200 | $(CH_2)_4$ | TIPS | H | OH | $CH_3$ |
| 2-201 | $(CH_2)_4$ | Bn | H | NHBz | H |
| 2-202 | $(CH_2)_4$ | Bn | Bn | NHBz | H |
| 2-203 | $(CH_2)_4$ | PMB | H | NHBz | H |
| 2-204 | $(CH_2)_4$ | PMB | PMB | NHBz | H |
| 2-205 | $(CH_2)_4$ | Tr | H | NHBz | H |
| 2-206 | $(CH_2)_4$ | MMTr | H | NHBz | H |
| 2-207 | $(CH_2)_4$ | DMTr | H | NHBz | H |
| 2-208 | $(CH_2)_4$ | TMTr | H | NHBz | H |
| 2-209 | $(CH_2)_4$ | TMS | H | NHBz | H |
| 2-210 | $(CH_2)_4$ | TBDMS | H | NHBz | H |
| 2-211 | $(CH_2)_4$ | TBDPS | H | NHBz | H |
| 2-212 | $(CH_2)_4$ | TIPS | H | NHBz | H |
| 2-213 | $(CH_2)_4$ | Bn | H | NHBz | $CH_3$ |
| 2-214 | $(CH_2)_4$ | Bn | Bn | NHBz | $CH_3$ |
| 2-215 | $(CH_2)_4$ | PMB | H | NHBz | $CH_3$ |
| 2-216 | $(CH_2)_4$ | PMB | PMB | NHBz | $CH_3$ |
| 2-217 | $(CH_2)_4$ | Tr | H | NHBz | $CH_3$ |
| 2-218 | $(CH_2)_4$ | MMTr | H | NHBz | $CH_3$ |

TABLE 2-continued

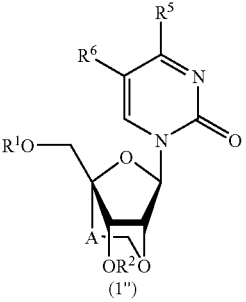

(1")

| Exe. com. num. | A | $R^1$ | $R^2$ | $R^5$ | $R^6$ |
|---|---|---|---|---|---|
| 2-219 | $(CH_2)_4$ | DMTr | H | NHBz | $CH_3$ |
| 2-220 | $(CH_2)_4$ | TMTr | H | NHBz | $CH_3$ |
| 2-221 | $(CH_2)_4$ | TMS | H | NHBz | $CH_3$ |
| 2-222 | $(CH_2)_4$ | TBDMS | H | NHBz | $CH_3$ |
| 2-223 | $(CH_2)_4$ | TBDPS | H | NHBz | $CH_3$ |
| 2-224 | $(CH_2)_4$ | TIPS | H | NHBz | $CH_3$ |
| 2-225 | $CH_2$ | H | H | NHBz | H |
| 2-226 | $CH_2$ | H | H | NHBz | $CH_3$ |
| 2-227 | $(CH_2)_2$ | H | H | NHBz | H |
| 2-228 | $(CH_2)_2$ | H | H | NHBz | $CH_3$ |
| 2-229 | $(CH_2)_3$ | H | H | NHBz | H |
| 2-230 | $(CH_2)_3$ | H | H | NHBz | $CH_3$ |
| 2-231 | $(CH_2)_4$ | H | H | NHBz | H |
| 2-232 | $(CH_2)_4$ | H | H | NHBz | $CH_3$ |
| 2-233 | $CH_2$ | DMTr | $P(N(iPr)_2)(OC_2H_4CN)$ | OH | H |
| 2-234 | $CH_2$ | DMTr | $P(N(iPr)_2)(OC_2H_4CN)$ | OH | $CH_3$ |
| 2-235 | $CH_2$ | DMTr | $P(N(iPr)_2)(OC_2H_4CN)$ | NHBz | H |
| 2-236 | $CH_2$ | DMTr | $P(N(iPr)_2)(OC_2H_4CN)$ | NHBz | $CH_3$ |
| 2-237 | $(CH_2)_2$ | DMTr | $P(N(iPr)_2)(OC_2H_4CN)$ | OH | H |
| 2-238 | $(CH_2)_2$ | DMTr | $P(N(iPr)_2)(OC_2H_4CN)$ | OH | $CH_3$ |
| 2-239 | $(CH_2)_2$ | DMTr | $P(N(iPr)_2)(OC_2H_4CN)$ | NHBz | H |
| 2-240 | $(CH_2)_2$ | DMTr | $P(N(iPr)_2)(OC_2H_4CN)$ | NHBz | $CH_3$ |
| 2-241 | $(CH_2)_3$ | DMTr | $P(N(iPr)_2)(OC_2H_4CN)$ | OH | H |
| 2-242 | $(CH_2)_3$ | DMTr | $P(N(iPr)_2)(OC_2H_4CN)$ | OH | $CH_3$ |
| 2-243 | $(CH_2)_3$ | DMTr | $P(N(iPr)_2)(OC_2H_4CN)$ | NHBz | H |
| 2-244 | $(CH_2)_3$ | DMTr | $P(N(iPr)_2)(OC_2H_4CN)$ | NHBz | $CH_3$ |
| 2-245 | $(CH_2)_4$ | DMTr | $P(N(iPr)_2)(OC_2H_4CN)$ | OH | H |
| 2-246 | $(CH_2)_4$ | DMTr | $P(N(iPr)_2)(OC_2H_4CN)$ | OH | $CH_3$ |
| 2-247 | $(CH_2)_4$ | DMTr | $P(N(iPr)_2)(OC_2H_4CN)$ | NHBz | H |
| 2-248 | $(CH_2)_4$ | DMTr | $P(N(iPr)_2)(OC_2H_4CN)$ | NHBz | $CH_3$ |
| 2-249 | $CH_2$ | DMTr | $P(N(iPr)_2)(OCH_3)$ | OH | H |
| 2-250 | $CH_2$ | DMTr | $P(N(iPr)_2)(OCH_3)$ | OH | $CH_3$ |
| 2-251 | $CH_2$ | DMTr | $P(N(iPr)_2)(OCH_3)$ | NHBz | H |
| 2-252 | $CH_2$ | DMTr | $P(N(iPr)_2)(OCH_3)$ | NHBz | $CH_3$ |
| 2-253 | $(CH_2)_2$ | DMTr | $P(N(iPr)_2)(OCH_3)$ | OH | H |
| 2-254 | $(CH_2)_2$ | DMTr | $P(N(iPr)_2)(OCH_3)$ | OH | $CH_3$ |
| 2-255 | $(CH_2)_2$ | DMTr | $P(N(iPr)_2)(OCH_3)$ | NHBz | H |
| 2-256 | $(CH_2)_2$ | DMTr | $P(N(iPr)_2)(OCH_3)$ | NHBz | $CH_3$ |
| 2-257 | $(CH_2)_3$ | DMTr | $P(N(iPr)_2)(OCH_3)$ | OH | H |
| 2-258 | $(CH_2)_3$ | DMTr | $P(N(iPr)_2)(OCH_3)$ | OH | $CH_3$ |
| 2-259 | $(CH_2)_3$ | DMTr | $P(N(iPr)_2)(OCH_3)$ | NHBz | H |
| 2-260 | $(CH_2)_3$ | DMTr | $P(N(iPr)_2)(OCH_3)$ | NHBz | $CH_3$ |
| 2-261 | $(CH_2)_4$ | DMTr | $P(N(iPr)_2)(OCH_3)$ | OH | H |
| 2-262 | $(CH_2)_4$ | DMTr | $P(N(iPr)_2)(OCH_3)$ | OH | $CH_3$ |
| 2-263 | $(CH_2)_4$ | DMTr | $P(N(iPr)_2)(OCH_3)$ | NHBz | H |
| 2-264 | $(CH_2)_4$ | DMTr | $P(N(iPr)_2)(OCH_3)$ | NHBz | $CH_3$ |

In the above Table 1 and Table 2, preferred compounds include the compounds (1-5), (1-7), (1-23), (1-24), (1-31), (1-35), (1-39), (1-43), (1-49), (1-51), (1-67), (1-68), (1-75), (1-79), (1-83), (1-87), (1-93), (1-95), (1-111), (1-112), (1-119), (1-123), (1-127), (1-131), (1-137), (1-139), (1-155), (1-156), (1-163), (1-167), (1-171), (1-175), (1-177), (1-178), (1-185), (1-186), (1-193), (1-194), (1-201), (1-202), (2-1), (2-2), (2-3), (2-4), (2-10), (2-15), (2-19), (2-22), (2 -27), 2-31), (2-34), (2-39), (2-43), (2-46), (2-51), (2-55), (2-57), (2-58), (2-59), (2-60), (2-60), (2-66), (2-71), (2-75), (2-78), (2-83), (2-87), (2-90), (2-95), (2-99), (2-102), (2-107), ( 2-111), (2-113), (2-114), (2-115), (2-116), (2-122), (2-127), (2-131), (2-134), (2-139), (2-143), (2-146), (2-151), (2-155), (2-158), (2-163), (2-167), (2-169), (2-170), (2-171), (2-172), (2-178), (2-183), (2-187), (2-190), (2-195), (2-199), (2-202), (2-207), (2-211), (2-214), (2-219), (2-223), (2-225), (2-226), (2-233), (2-234), (2-235) or (2-236), more preferred compounds may include 2'-O,4'-C-ethyleneguanosine (1-5), 2'-O,4'-C-ethyleneadenosine (1-7), 3',5'-di-O-benzyl-2'-O,4'-C-ethylene-6-N-benzoyladenosine (1-23), 3',5'-di-O-benzyl-2'-O,4'-C-ethylene-2-N-isobutyrylguanosine (1-24), 5'-O-dimethoxytrityl-2'-O,4'-C-ethylene-6-N-benzoyladenosine (1-31), 5'-O-dimethoxytrityl-2'-O,4'-C-ethylene-2-N-isobutyrylguanosine (1-35), 2'-O,4'-C-ethylene-2-N-isobutyrylguanosine (1-177), 2'-O,4'-C-ethylene-6-N-benzoyladenosine (1-178), 5'-O-dimethoxytrityl-2'-O,4'-C-ethylene-2-N-isobutyrlguanosine-3'-O-(2-cyanoethyl N,N-diisopropyl)phosphoramidite (1-185), 5'-O-dimethoxytrityl-2'-O,4'-C-ethylene-6-N-benzoyladenosine-3'-O-(2-cyanoethyl N,N-diisopropyl)phosphoramidite (1-186), 2'-O,4'-C-ethyleneuridine (2-1), 2'-O,4'-C-ethylene-5-methyluridine (2-2), 2'-O,4'-C-ethylenecytidine (2-3), 2'-O,4'-C-ethylene-5-methylcytidine (2-4), 3',5'-di-O-benzyl-2'-O,4'-C-ethyleneuridine (2-10), 5'-O-dimethoxytrityl-2'-O,4'-C-ethyleneuridine (2-15), 3',5'-di-O-benzyl-2'-O,4'-C-ethylene-5-methyluridine (2-22), 5'-O-dimethoxytrityl-2'-O,4'-C-ethylene-5-methyluridine (2-27), 3',5'-di-O-benzyl-2'-O,4'-C-ethylene-4-N-benzoylcytidine (2-34), 5'-O-dimethoxytrityl-2'-O,4'-C-ethylene-4-N-benzoylcytidine (2-39), 3',5'-di-O-benzyl-2'-O,4'-C-ethylene-4-N-benzoyl-5-methylcytidine (2-46), 5'-O-dimethoxytrityl-2'-O,4'-C-ethylene-4-N-benzoyl-5-methylcytidine (2-51), 2'-O,4'-C-ethylene-4-N-benzoylcytidine (2-225), 2'-O,4'-C-ethylene-4-N-benzoyl-5-methylcytidine (2-226), 5'-O-dimethoxytrityl-2'-O,4'-C-ethylene-uridine-3'-O-(2-cyanoethyl N,N-diisopropyl)phosphoramidite (2-233), 5'-O-dimethoxytrityl-2'-O,4'-C-ethylene-5-methyluridine-3'-O-(2-cyanoethyl N,N-diisopropyl)phosphoramidite (2-234), 5'-O-dimethoxytrityl-2'-O,4'-C-ethylene-4-N-benzoylcytidine-3'-O-(2-cyanoethyl N,N-diisopropyl)phosphoramidite (2-235), and 5'-O-dimethoxytrityl-2'-O,4'-C-ethylene-4-N-benzoyl-5-methylcytidine-3'-O-(2-cyanoethyl N,N-diisopropyl)phosphoramidite (2-236).

The compound (1) of the present invention can be produced according to Process A described below.

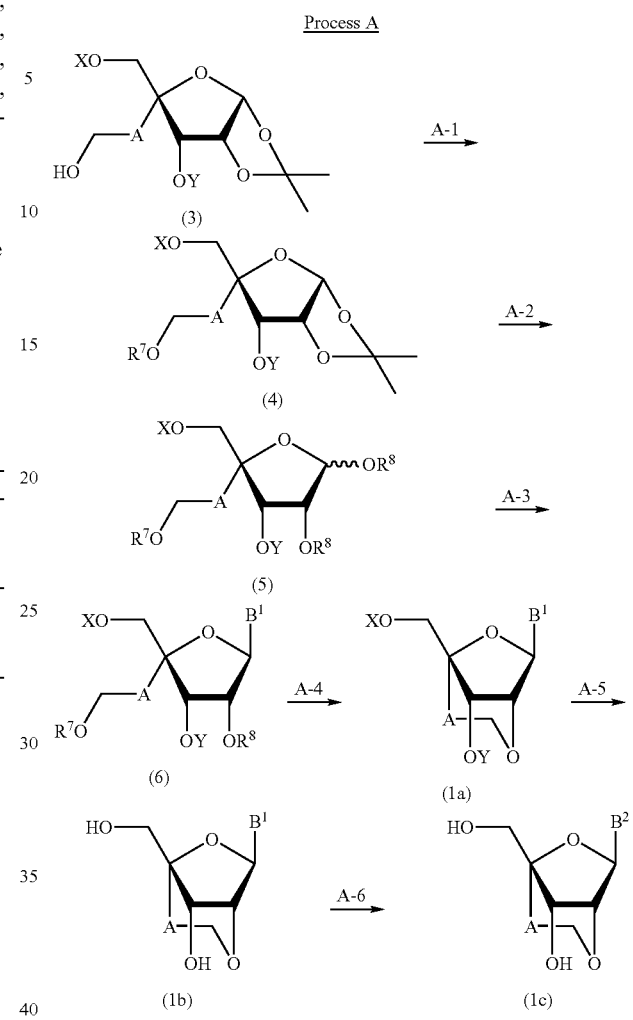

Process A

In Process A, X represents a protecting group; Y represents a protecting group; A has the same meaning as defined above; while $B^1$ represents a purin-9-yl group, a substituted purin-9-yl group or a substituted 2-oxo-pyrimidin-1-yl group, said substituents being selected from the above substituents but with the exclusion of an unprotected amino group of "an amino group which may be protected"; while $B^2$ represents a purin-9-yl group, a substituted purin-9-yl group or a substituted 2-oxo-pyrimidin-1-yl group, said substituents being selected from the above substituents but with the exclusion of protected amino groups of "an amino group which may be protected"; $R^7$ represents a group which forms a leaving group; and $R^8$ represents an aliphatic acyl group having from 1 to 4 carbon atoms.

The protecting group of X is the same group as "the hydroxyl protecting group" in the above $R^1$.

The protecting group of Y is the same group as "the hydroxyl protecting group" in the above $R^2$.

"The group which forms a leaving group" of $R^7$ may include a lower alkylsulfonyl group such as methanesulfonyl and ethanesulfonyl; a halogen-substituted lower alkylsulfonyl group such as trifluoromethanesulfonyl; and an arylsulfonyl group such as p-toluenesulfonyl; preferably a methanesulfonyl group or a p-toluenesulfonyl group.

"The aliphatic acyl group having from 2 to 4 carbon atoms" of $R^8$ may include acetyl, propionyl, butyryl groups and the like, preferably an acetyl group.

In the following, each step of Process A will be described in detail.

(Step A-1)

The present step is to prepare a compound (4) by reacting a compound (3) which can be prepared by Methods B to D described later with a reagent for introducing a leaving group in the presence of a base catalyst in an inert solvent.

The solvent employable here may include aliphatic hydrocarbons such as hexane, heptane, ligroin and petroleum ether; aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; ketones such as acetone, methyl ethyl ketone, methyl isobutyl ketone, isophorone and cyclohexanone; nitro compounds such as nitroethane and nitrobenzene; nitriles such as acetonitrile and isobutyronitrile; amides such as formamide, N,N-dimethylformamide, N,N-dimethylacetamide, N-methyl-2-pyrrolidone, N-methylpyrrolidinone and hexamethylphosphoric triamide; sulfoxides such as sulfolane; and pyridine derivatives; preferably pyridine.

The base catalyst employable here may preferably include a base such as triethylamine, pyridine and dimethylaminopyridine.

The reagent for introducing a leaving group may include alkylsulfonyl halides such as methanesulfonyl chloride and ethanesulfonyl bromide; and arylsulfonyl halides such as p-toluenesulfonyl chloride, preferably methanesulfonyl chloride and p-toluenesulfonyl chloride.

The reaction temperature varies depending on the starting material, the solvent, the reagent for introducing a leaving group and the base catalyst, but is usually from 0° C. to 50° C., preferably from 10° C. to 40° C.

The reaction time varies depending on the starting material, the solvent, the reagent for introducing a leaving group, the base catalyst and the reaction temperature, but is usually from 10 minutes to 24 hours, preferably from 1 to 10 hours.

After the reaction, the desired compound (4) of the present reaction is obtained, for example, by neutralizing the reaction solution, concentrating the reaction mixture, adding an organic solvent immiscible with water such as ethyl acetate, washing with water, separating an organic layer containing the desired compound, drying over anhydrous magnesium sulfate and distilling off the solvent.

The desired product thus obtained can be further purified, if necessary, by a conventional method, for example, recrystallization and silica gel column chromatography.

(Step A-2)

The present step is to prepare the compound (5) by reacting the compound (4) prepared in Step A-1 with an acid anhydride in the presence of an acid catalyst in a solvent.

The solvent employable here may include ethers such as diethyl ether, dioxane and tetrahydrofuran; nitrites such as acetonitrile and isobutyronitrile; amides such as formamide, N,N-dimethylformamide, N,N-dimethylacetamide, N-methyl-2-pyrrolidone, N-methylpyrrolidinone and hexamethylphosphororic triamide; and organic acids such as acetic acid; preferably acetic acid.

The acid catalyst employable here may include inorganic acids such as hydrochloric acid, sulfuric acid and nitric acid, preferably sulfuric acid (particularly concentrated sulfuric acid).

The acid anhydride employable here may include an anhydride of a lower aliphatic carboxylic acid such as acetic anhydride and propionic acid anhydride, preferably acetic anhydride.

The reaction temperature varies depending on the starting material, the solvent, the acid catalyst and the acid anhydride and is usually from 0° C. to 50° C., preferably from 10° C. to 40° C.

The reaction time varies depending on the starting material, the solvent, the acid catalyst, the acid anhydride and the reaction temperature, but is usually from 10 minutes to 12 hours, preferably from 30 minutes to 3 hours.

After the reaction, the desired compound (5) of the present reaction is obtained, for example, by concentrating the reaction mixture, adding an organic solvent immiscible with water such as ethyl acetate, washing with water, separating an organic layer containing the desired compound, drying over anhydrous magnesium sulfate and distilling off the solvent.

The desired product thus obtained can be further purified, if necessary, by a conventional method, for example, recrystallization, silica gel column chromatography and the like.

(Step A-3)

The present step is to prepare the compound (6) by reacting the compound (5) prepared in Step A-2 with a trimethylsilylated compound corresponding to the purine or pyrimidine which may have a desired substituent prepared according to a reference (H. Vorbrggen, K. Krolikiewicz and B. Bennua, Chem. Ber., 114, 1234-1255 (1981)) in the presence of an acid catalyst in an inert solvent.

The solvent employable here may include aromatic hydrocarbons such as benzene, toluene, xylene; halogenated hydrocarbons such as methylene chloride, chloroform, carbon tetrachloride, 1,2-dichloroethane, chlorobenzene and dichlorobenzene; nitriles such as acetonitrile and isobutyronitrile; amides such as formamide, N,N-dimethylformamide, N,N-dimethylacetamide, N-methyl-2-pyrrolidone, N-methylpyrrolidinone and hexamethylphosphoric triamide; carbon sulfide; preferably 1,2-dichloroethane.

The acid catalyst employable here may include Lewis acid catalysts such as $AlCl_3$, $SnCl_4$, $TiCl_4$, $ZnCl_2$, $BF_3$, trimethylsilyl trifluoromethanesulfonate; preferably trimethylsilyl trifluoromethanesulfonate.

The reaction temperature varies depending on the starting material, the solvent and the acid catalyst but is usually from 0° C. to 100° C., preferably from 50° C. to 80° C.

The reaction time varies depending on the starting material, the solvent, the acid catalyst and the reaction temperature but is usually from 1 hour to 24 hours, preferably from 1 hour to 8 hours.

After the reaction, the desired compound (6) of the present reaction is obtained, for example, by concentrating the reaction mixture, adding an organic solvent immiscible with water such as ethyl acetate, washing with water, separating an organic layer containing the desired compound, drying over anhydrous magnesium sulfate and distilling off the solvent.

The desired product thus obtained can be further purified, if necessary, by a conventional method, for example, recrystallization, silica gel column chromatography and the like.

(Step A-4)

The present step is to prepare the compound (1a) of the present invention by cyclization of the compound (6) prepared by Step A-3 in the presence of a base catalyst in an inert solvent.

The solvent employable here may include water; pyridine derivatives; acetonitriles such as acetonitrile and isobutyronitrile; amides such as formamide, N,N-dimethylformamide, N,N-dimethylacetamide, N-methyl-2-pyrrolidone, N-methylpyrrolidinone and hexamethylphosphoric triamide; and a mixture thereof, preferably a mixture of water and pyridine.

The base catalyst employable here may include alkali metal hydroxides such as sodium hydroxide and potassium hydroxide; alkali metal carbonates such as sodium carbonate and potassium carbonate; alkali metal alkoxides such as sodium methoxide and sodium ethoxide; and aqueous ammonia; preferably alkali metal hydroxides (particularly sodium hydroxide).

The reaction temperature varies depending on the starting material, the solvent and the base catalyst but is usually from 0° C. to 50° C., preferably from 10° C. to 30° C.

The reaction time varies depending on the starting material, the solvent, the acid catalyst and the reaction temperature but is usually from 1 minute to 5 hours, preferably from 1 minute to 30 minutes.

After the reaction, the desired compound (1a) of the present reaction is obtained, for example, by concentrating the reaction mixture, adding an organic solvent immiscible with water such as ethyl acetate, washing with water, separating an organic layer containing the desired compound, drying over anhydrous magnesium sulfate and distilling off the solvent.

The desired product thus obtained can be further purified, if necessary, by a conventional method, for example, recrystallization, silica gel column chromatography and the like.

(Step A-5)

The present step is to prepare the compound (1b) by reacting the compound (1a) obtained by Step A-4 with a deprotecting reagent in an inert solvent.

The deprotection method varies depending on the kind of protecting group and is not particularly limited unless it causes other side reactions and can be carried out, for example, by a method described in "Protective Groups in Organic Synthesis" (Theodora W. Greene and Peter G. M. Wuts, 1999, Published by A Wiley-Interscience Publication).

Particularly, the deprotection method can be carried out by the following methods in the case where the protecting group is (1) "an aliphatic acyl group or an aromatic acyl group", (2) "a methyl group substituted by from 1 to 3 aryl groups" or "a methyl group substituted by from 1 to 3 aryl groups the aryl ring of which is substituted by lower alkyl, lower alkoxy, halogen or cyano group" or (3) "a silyl group".

(1) In the case where the protecting group is an aliphatic acyl group or an aromatic acyl group, the deprotection reaction is usually carried out by treating it with a base in an inert solvent.

The solvent employable here is not particularly limited so long as it is easily mixed with water, does not inhibit the reaction and dissolves the starting material to some extent and may include aqueous or anhydrous amides such as dimethylformamide and dimethylacetamide; halogenated hydrocarbons such as methylene chloride, chloroform, 1,2-dichloroethane or carbon tetrachloride; and ethers such as tetrahydrofuran, diethyl ether and dioxane; preferably ethers, more preferably tetrahydrofuran.

The base employable here may include alkali metal hydroxides such as lithium hydroxide, potassium hydroxide and sodium hydroxide; alkali metal carbonates such as sodium carbonate and potassium carbonate; alkali metal alkoxides such as sodium methoxide and sodium ethoxide; and an ammonia solution such as aqueous ammonia and ammonia/methanol solution.

The reaction temperature is from 0° C. to 60° C., preferably from 20° C. to 40° C.

The reaction time is from 10 minutes to 24 hours, preferably from 1 hour to 3 hours.

After the reaction, the desired compound (1b) of the present reaction is obtained, for example, by concentrating the reaction mixture, adding an organic solvent immiscible with water such as ethyl acetate, washing with water, separating an organic layer containing the desired compound, drying over anhydrous magnesium sulfate and distilling off the solvent.

The desired product thus obtained can be further purified, if necessary, by a conventional method, for example, recrystallization, silica gel column chromatography and the like.

(2) In the case where the protecting group is "a methyl group substituted by from one to three aryl groups" or "a methyl group substituted by from one to three aryl groups the aryl ring of which is substituted by a lower alkyl, lower alkoxy, halogen or cyano group", the reaction is carried out in an inert solvent using a reducing agent.

The solvent employable here may preferably include alcohols such as methanol, ethanol and isopropanol; ethers such as diethyl ether, tetrahydrofuran and dioxane; aromatic hydrocarbons such as toluene, benzene and xylene; aliphatic hydrocarbons such as hexane and cyclohexane; esters such as ethyl acetate and propyl acetate; organic acids such as acetic acid; or a mixture of these organic solvents and water.

The reducing agent employable here is not particularly limited so long as it is usually used for a catalytic reduction and may preferably include palladium on carbon, Raney nickel, platinum oxide, platinum black, rhodium-aluminum oxide, triphenylphosphine-rhodium chloride and palladium-barium sulfate.

The pressure is not particularly limited but is usually from 1 to 10 atm.

The reaction temperature is from 0° C. to 60° C., preferably from 20° C. to 40° C.

The reaction time is from 10 minutes to 24 hours, preferably from one hour to three hours.

After the reaction, the desired compound (1b) of the present reaction is obtained, for example, by removing the reducing agent from the reaction mixture, adding an organic solvent immiscible with water such as ethyl acetate, washing with water, separating an organic layer containing the desired compound, drying over anhydrous magnesium sulfate and distilling off the solvent. The desired product thus obtained can be further purified, if necessary, by a conventional method, for example, recrystallization, silica gel column chromatography and the like.

In the case where the protecting group is "a methyl group substituted by three aryl groups", i.e., a trityl group, the deprotection reaction can be also carried out using an acid.

In this case, the solvent employable here may include aromatic hydrocarbons such as benzene, toluene and xylene; halogenated hydrocarbons such as methylene chloride, chloroform, carbon tetrachloride, 1,2-dichloroethane, chlorobenzene and dichlorobenzene; alcohols such as methanol, ethanol, isopropanol and tert-butanol; nitrites such as acetonitrile and isobutyronitrile; amides such as formamide, N,N-dimethylformamide, N,N-dimethylacetamide, N-methyl-2-pyrrolidone, N-methylpyrrolidinone and hexamethylphosphoric triamide; and organic acids such as acetic acid; preferably organic acids (particularly acetic acid) or alcohols (particularly tert-butanol).

The acid employable here may preferably include acetic acid or trifluoroacetic acid.

The reaction temperature is from 0° C. to 60° C., preferably from 20° C. to 40° C.

The reaction time is from 10 minutes to 24 hours, preferably from one 1 to 3 hours.

After the reaction, the desired compound (1b) of the present reaction is obtained, for example, by neutralizing the reaction mixture, adding an organic solvent immiscible with water such as ethyl acetate, washing with water, separating an organic layer containing the desired compound, drying over anhydrous magnesium sulfate and distilling off the solvent.

The desired product thus obtained can be further purified, if necessary, by a conventional method, for example, recrystallization, silica gel column chromatography and the like.

(3) In the case where the protecting group is "a silyl group", it can usually be removed by treating with a compound producing a fluorine anion such as tetrabutylammonium fluoride, hydrofluoric acid, hydrofluoric acid-pyridine and potassium fluoride, or organic acids such as acetic acid, methanesulfonic acid, para-toluenesulfonic acid, trifluoroacetic acid and trifluoromethanesulfonic acid, or inorganic acids such as hydrochloric acid.

In the case where the protecting group is removed by a fluorine anion, the reaction is sometimes promoted by adding organic acids such as formic acid, acetic acid and propionic acid thereto.

The solvent employable here is not particularly limited so long as it does not inhibit the reaction and dissolves the starting material to some extent and may preferably include ethers such as diethyl ether, diisopropyl ether, tetrahydrofuran, dioxane, dimethoxyethane and diethylene glycol dimethyl ether; nitrites such as acetonitrile and isobutyronitrile; water; organic acids such as acetic acid; and a mixture thereof.

The reaction temperature is from 0° C. to 100° C., preferably from 20° C. to 70° C.

The reaction time is from 5 minutes to 48 hours, preferably from one hour to 24 hours.

After the reaction, the desired compound (1b) of the present reaction is obtained, for example, by concentrating the reaction mixture, adding an organic solvent immiscible with water such as ethyl acetate, washing with water, separating an organic layer containing the desired compound, drying over anhydrous magnesium sulfate and distilling off the solvent. The desired product thus obtained can be further purified, if necessary, by a conventional method, for example, recrystallization, silica gel column chromatography and the like.

(Step A-6)

The present step is to prepare the compound (1c) of the present invention by reacting the compound (1b) obtained in Step A-5 with a deprotection reagent in an inert solvent.

The deprotection method varies depending on the kind of protecting group and is not particularly limited so long as it does not cause other side reactions and can be carried out, for example, by a method described in "Protective Groups in Organic Synthesis" (by Theodora W. Greene, 1981, published by A Wiley-Interscience Publication).

Particularly, the deprotection method can be carried out by the following method in the case where the protecting group is an aliphatic acyl group or an aromatic acyl group.

Namely, the deprotection method is usually carried out by reacting with a base in an inert solvent in the case where the protecting group is an aliphatic acyl group or an aromatic acyl group.

The solvent employable here is not particularly limited so long as it is easily mixed with water, does not inhibit the reaction and dissolves the starting material to some extent and may include aqueous or anhydrous alcohols such as methanol and ethanol; amides such as dimethylformamide and dimethylacetamide; halogenated hydrocarbons such as methylene chloride, chloroform, 1,2-dichloroethane or carbon tetrachloride; and ethers such as tetrahydrofuran, diethyl ether and dioxane; preferably alcohols; more preferably methanol.

The base employable here may include alkali metal hydroxides such as lithium hydroxide, potassium hydroxide and sodium hydroxide; alkali metal carbonates such as sodium carbonate and potassium carbonate; alkali metal alkoxides such as sodium methoxide and sodium ethoxide; and ammonia; preferably ammonia.

The reaction temperature is from 0° C. to 50° C., preferably from 10° C. to 40° C.

The reaction time is from 10 minutes to 24 hours, preferably from 10 minutes to 15 hours. After the reaction, the desired compound (1c) of the present reaction is obtained, for example, by concentrating the reaction mixture, adding an organic solvent immiscible with water such as ethyl acetate, washing with water, separating an organic layer containing the desired compound, drying over anhydrous magnesium sulfate and distilling off the solvent.

The desired product thus obtained can be further purified, if necessary, by a conventional method, for example, recrystallization, silica gel column chromatography and the like.

The intermediate (3) described above can be prepared by Processes B to D described below.

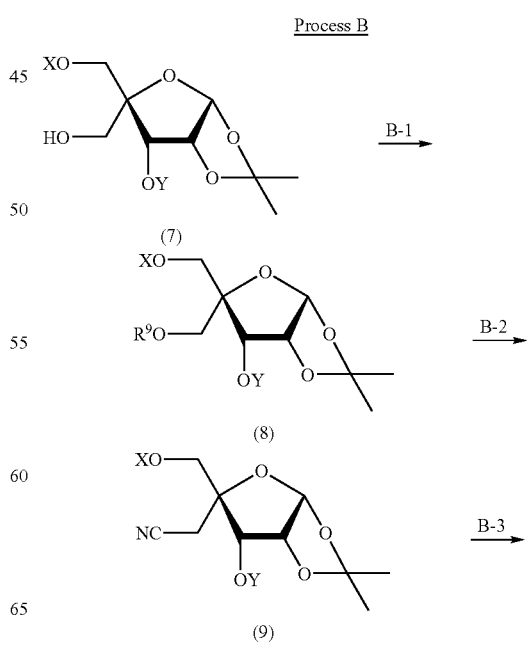

Process B

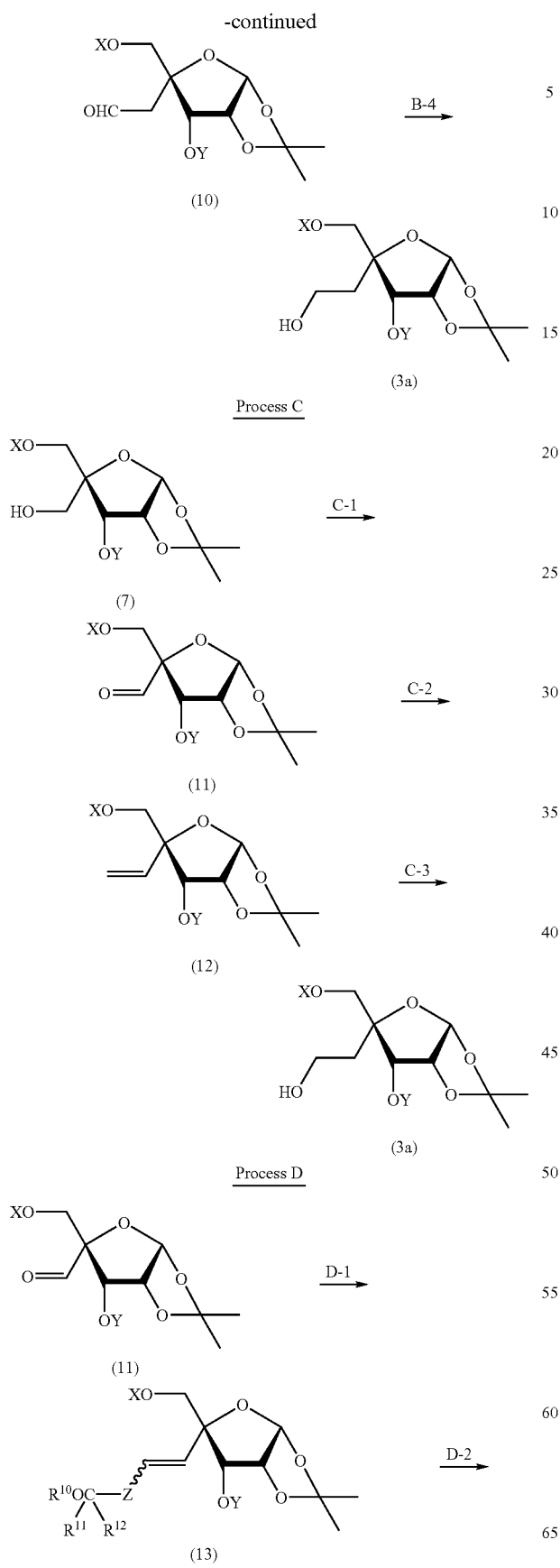

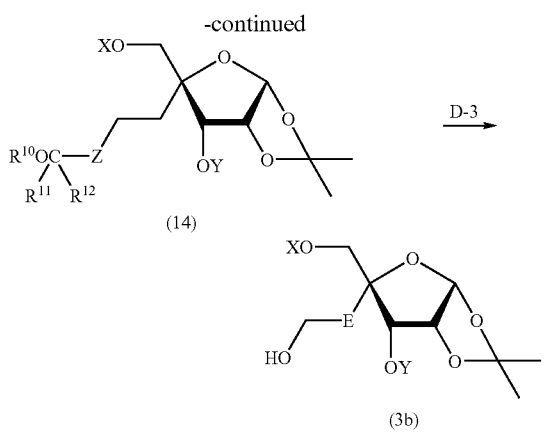

In Processes B to D, X and Y have the same meanings as defined above; $R^9$ represents a group which forms a leaving group; E represents an ethylene, trimethylene or tetramethylene group; and Z represents a single bond, a methylene or ethylene group.

The group which forms a leaving group of $R^9$ may include the group described in the above $R^7$, preferably a trifluoromethanesulfonyl group.

$R^{11}$ and $R^{12}$ are the same and represent a hydrogen atom or taken together form an oxygen atom.

In the case where $R^{11}$ and $R^{12}$ taken together form the oxygen atom, $R^{10}$ represents an alkyl group having from 1 to 4 carbon atoms such as methyl, ethyl, propyl, isopropyl, butyl, isobutyl, s-butyl and tert-butyl, preferably a methyl group. In the case where $R^{11}$ and $R^{12}$ are the same and represent a hydrogen atom, $R^{10}$ may include an aralkyl group such as a benzyl group; an alkoxyalkyl group such as a methoxymethyl group; an arylcarbonyloxymethyl group such as a benzoyloxymethyl group, an aralkyloxymethyl group such as a benzyloxymethyl group; an alkoxyalkoxyalkyl group such as a methoxyethoxymethyl group; a silyl group such as trimethylsilyl, t-butyldimethylsilyl, diphenylmethylsilyl, diphenylbutylsilyl, diphenylisopropylsilyl and phenyldiisopropylsilyl.

The compound (7), i.e., the starting material used in Process B or Process C can be prepared by the following method.

Namely, a compound corresponding to the compound (6) of which the "X" moiety is a hydrogen atom is prepared from 1,1,5,6-diisopropylidene D-glucose on public sale according to the method of the literature (R. D. Youssefyeh, J. P. H. Verheyden, J. G. Moffatt. *J. Org. Chem.*, 44, 1301-1309 (1979)) and subsequently the compound (6) can be prepared according to the method of the literature (T. Waga, T. Nishizaki, I. Miyakawa, H. Ohrui, H. Meguro, *Biosci. Biotechnol. Biochem.*, 57, 1433-1438 (1993)) (in the case of X=Bn).

(Process B)

(Step B-1)

The present step is to prepare the compound (8) by reacting the compound (7) prepared by the above method with a reagent for introducing a leaving group in the presence of a base catalyst in an inert solvent.

The solvent employable here may include amides such as dimethylformamide and dimethylacetamide; halogenated hydrocarbons such as methylene chloride, chloroform, 1,2- dichloroethane or carbon tetrachloride; and ethers such as tetrahydrofuran, diethyl ether and dioxane; preferably methylene chloride.

The base catalyst employable here may preferably include a base such as triethylamine, pyridine and dimethylaminopyridine.

The reagent employable for introducing a leaving group may preferably include trifluoromethanesulfonic acid chloride or trifluoromethanesulfonic anhydride.

The reaction temperature varies depending on the starting material, the solvent and the acid catalyst, but is usually from −100° C. to −50° C., preferably from −100° C. to −70° C.

The reaction time varies depending on the starting material, the solvent, the acid catalyst and the reaction temperature but is usually from 30 minutes to 12 hours, preferably from 30 minutes to 3 hours.

After the reaction, the desired compound (8) of the present reaction is obtained, for example, by concentrating the reaction mixture, adding an organic solvent immiscible with water such as ethyl acetate, washing with water, separating an organic layer containing the desired compound, drying over anhydrous magnesium sulfate and distilling off the solvent.

The desired product thus obtained can be further purified, if necessary, by a conventional method, for example, recrystallization, silica gel column chromatography and the like.

(Step B-2)

The present step is to prepare the compound (9) by reacting the compound (8) prepared by Step B-1 with a cyanating reagent in an inert solvent.

The solvent employable here may include amides such as dimethylformamide and dimethylacetamide; halogenated hydrocarbons such as methylene chloride, chloroform, 1,2-dichloroethane or carbon tetrachloride; ethers such as tetrahydrofuran, diethyl ether and dioxane; acetonitrile; dimethylsulfoxide and the like; preferably amides (dimethylformamide).

The cyanating reagent employable here may include KCN, NaCN and trimethylsilane cyanide, preferably NaCN.

The reaction temperature varies depending on the starting material, the solvent and the cyanating reagent but is usually from 0° C. to 100° C., preferably from 30° C. to 70° C.

The reaction time varies depending on the starting material, the solvent, the cyanating reagent and the reaction temperature but is usually from 30 minutes to 12 hours, preferably from one 1 to 3 hours.

After the reaction, the desired compound (9) of the present reaction is obtained, for example, by concentrating the reaction mixture, adding an organic solvent immiscible with water such as ethyl acetate, washing with water, separating an organic layer containing the desired compound, drying over anhydrous magnesium sulfate and distilling off the solvent.

The desired product thus obtained can be further purified, if necessary, by a conventional method, for example, recrystallization, silica gel column chromatography and the like.

(Step B-3)

The present step is to prepare the compound (10) by reacting the compound (9) prepared in Step B-2 with a reducing agent in an inert solvent.

The solvent employable here may include halogenated hydrocarbons such as methylene chloride, chloroform, 1,2-dichloroethane or carbon tetrachloride; aliphatic hydrocarbons such as hexane, heptane, ligroin and petroleum ether; aromatic hydrocarbons such as benzene, toluene and xylene; ethers such as diethyl ether, diisopropyl ether, tetrahydrofuran, dioxane, dimethoxyethane and diethylene glycol dimethyl ether; and ketones such as acetone, methyl ethyl ketone, methyl isobutyl ketone isophorone and cyclohexanone; preferably halogenated hydrocarbons (particularly methylene chloride).

The reducing agent employable here may include diisobutyl aluminum hydride and triethoxy aluminum hydride, preferably diisobutyl aluminum hydride.

The reaction temperature varies depending on the starting material, the solvent and the reducing agent but is usually from −100° C. to −50° C., preferably from −90° C. to −70° C.

The reaction time varies depending on the starting material, the solvent, the reducing agent and the reaction temperature but is usually from 30 minutes to 12 hours, preferably from 1 hour to 5 hours.

After the reaction, the desired compound (10) of the present reaction is obtained, for example, by concentrating the reaction mixture, adding an organic solvent immiscible with water such as ethyl acetate, washing with water, separating an organic layer containing the desired compound, drying over anhydrous magnesium sulfate and distilling off the solvent.

The desired product thus obtained can be further purified, if necessary, by a conventional method, for example, recrystallization, silica gel column chromatography and the like.

(Step B-4)

The present step is to prepare the compound (3a), one of the starting materials of Process A by reacting the compound (10) prepared in Step B-3 with a reducing agent in an inert solvent.

The solvent employable here may include alcohols such as methanol, ethanol, n-propanol, isopropanol, n-butanol, isobutanol, t-butanol, isoamyl alcohol, diethylene glycol, glycerine, octanol, cyclohexanol and methyl cellosolve; and acetic acid; preferably alcohols (particularly ethanol).

The reducing agent employable here may include alkali metal boron hydrides such as sodium boron hydride and lithium boron hydride; aluminum hydride compounds such as lithium aluminum hydride and lithium triethoxide aluminum hydride; and borane; preferably sodium boron hydride.

The reaction temperature varies depending on the starting material, the solvent and the reducing agent but is usually from 0° C. to 50° C., preferably from 10° C. to 40° C.

The reaction time varies depending on the starting material, the solvent, the reducing agent and the reaction temperature but is usually from 10 minutes to 12 hours, preferably from 30 minutes to 5 hours.

After the reaction, the desired compound (3a) of the present reaction is obtained, for example, by decomposing the reducing agent, concentrating the reaction mixture, adding an organic solvent immiscible with water such as ethyl acetate, washing with water, separating an organic layer containing the desired compound, drying over anhydrous magnesium sulfate and distilling off the solvent.

The desired product thus obtained can be further purified, if necessary, by a conventional method, for example, recrystallization, silica gel column chromatography and the like.

(Process C)

(Step C-1)

The present step is to prepare the compound (11) by reacting the compound (7) prepared in the above process with an oxidizing agent in an inert solvent.

The solvent employable here may include aliphatic hydrocarbons such as hexane, heptane, ligroin and petroleum ether; aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran, dioxane, dimethoxyethane, diethylene glycol dimethyl ether; and ketones such as acetone, methyl ethyl ketone, methyl isobutyl ketone, isophorone and cyclohexanone; preferably halogenated hydrocarbons (particularly methylene chloride).

The oxidizing agent employable here may include the Swern reagent for oxidation, the Dess-Martin reagent for oxidation, a chromium trioxide complex such as pyridine hydrochloride/chromium trioxide complex (pyridinium chlorochromate and pyridinium dichromate), preferably the Swern reagent for oxidation (namely, dimethyl sulfoxide-oxalyl chloride).

The reaction temperature varies depending on the starting material, the solvent and the oxidizing agent but is usually from –100° C. to –50° C., preferably from –100° C. to –70° C.

The reaction time varies depending on the starting material, the solvent, the oxidizing agent and the reaction temperature but is usually from 30 minutes to 12 hours, preferably from 1 hour to 5 hours.

After the reaction, the desired compound (11) of the present reaction is obtained, for example, by decomposing the oxidizing agent, concentrating the reaction mixture, adding an organic solvent immiscible with water such as ethyl acetate, washing with water, separating an organic layer containing the desired compound, drying over anhydrous magnesium sulfate and distilling off the solvent.

The desired product thus obtained can be further purified, if necessary, by a conventional method, for example, recrystallization, silica gel column chromatography and the like.

(Step C-2)

The present step is to prepare the compound (12) by reacting the compound (11) prepared in Step C-1 with a carbon-increasing reagent in an inert solvent.

The solvent employable here may include aliphatic hydrocarbons such as hexane, heptane, ligroin and petroleum ether; aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran, dioxane, dimethoxyethane, diethylene glycol dimethyl ether; and ketones such as acetone, methyl ethyl ketone, methyl isobutyl ketone, isophorone and cyclohexanone; preferably halogenated hydrocarbons (particularly methylene chloride).

The reagent employable here may include the Wittig reagent, Horner-Emmons reagent, Peterson reaction reagent, $TiCl_4$—$CH_2Cl_2$—Zn system reaction agent and Tebbe reagent, preferably the Wittig reagent, Horner-Emmons reagent and Tebbe reagent.

The reaction temperature varies depending on the starting material, the solvent and the carbon-increasing reagent but is usually from –20° C. to 20° C., preferably 0° C.

The reaction time varies depending on the starting material, the solvent, the carbon-increasing reagent and the reaction temperature but is usually from 30 minutes to 12 hours, preferably from 1 hour to 5 hours.

After the reaction, the desired compound (12) of the present reaction is obtained, for example, by concentrating the reaction mixture, adding an organic solvent immiscible with water such as ethyl acetate, washing with water, separating an organic layer containing the desired compound, drying over anhydrous magnesium sulfate and distilling off the solvent.

The desired product thus obtained can be further purified, if necessary, by a conventional method, for example, recrystallization, silica gel column chromatography and the like.

(Step C-3)

The present step is to prepare the compound (3a) by selectively introducing a hydroxyl group to a terminal carbon of olefin of the compound (12) prepared in Step C-2 in an inert solvent.

The solvent employable here may include aliphatic hydrocarbons such as hexane, heptane, ligroin and petroleum ether; aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; and ketones such as acetone, methyl ethyl ketone, methyl isobutyl ketone, isophorone and cyclohexanone; preferably ethers (particularly tetrahydrofuran).

The reaction reagent employable here may include borane, disiamyl borane, thexyl borane, 9-BBN (9-borabicyclo[3.3.1]nonane), preferably the 9-BBN.

The reaction temperature varies depending on the starting material, the solvent and the reagent but is usually from 0° C. to 50° C., preferably from 10° C. to 40° C.

The reaction time varies depending on the starting material, the solvent, the reagent and the reaction temperature but is usually from 6 hours to 48 hours, preferably from 12 hours to 24 hours.

After the reaction, the desired compound (3a) of the present reaction is obtained, for example, by concentrating the reaction mixture, adding an organic solvent immiscible with water such as ethyl acetate, washing with water, separating an organic layer containing the desired compound, drying over anhydrous magnesium sulfate and distilling off the solvent.

The desired product thus obtained can be further purified, if necessary, by a conventional method, for example, recrystallization, silica gel column chromatography and the like.

(Process D)

(Step D-1)

The present step is to prepare the compound (13) by reacting the compound (11) prepared in Step C-1 with a carbon-increasing reagent in an inert solvent.

The solvent employable here may include aliphatic hydrocarbons such as hexane, heptane, ligroin and petroleum ether; aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; and ketones such as acetone, methyl ethyl ketone, methyl isobutyl ketone, isophorone and cyclohexanone; preferably ethers (particularly tetrahydrofuran), more preferably halogenated hydrocarbons (particularly methylene chloride).

The carbon-increasing reagent employable here may include the Wittig reagent and Horner-Emmons reagent.

The reaction temperature varies depending on the starting material, the solvent and the reagent but is usually from −20° C. to 40° C., preferably from 0° C. to 20° C.

The reaction time varies depending on the starting material, the solvent, the reagent and the reaction temperature but is usually from 30 minutes to 12 hours, preferably from 1 hour to 5 hours.

After the reaction, the desired compound (13) of the present reaction is obtained, for example, by concentrating the reaction mixture, adding an organic solvent immiscible with water such as ethyl acetate, washing with water, separating an organic layer containing the desired compound, drying over anhydrous magnesium sulfate and distilling off the solvent.

The desired product thus obtained can be further purified, if necessary, by a conventional method, for example, recrystallization, silica gel column chromatography and the like.

(Step D-2)

The present step is to prepare the compound (14) by reacting the compound (13) prepared in Step D-1 with a reducing agent in an inert solvent.

The present step can be carried out according to (2) of Step A-5. In the case where $R^{10}$ is an optionally substituted benzyl group and $R^{11}$ and $R^{12}$ are hydrogen atoms, the compound (3b) can be directly prepared in this step.

(Step D-3)

The present step is to prepare the compound (3b), one of the starting materials of Process A by reacting the compound (14) prepared in Step D-2 with a reducing agent.

(a) In the case where $R^{11}$ and $R^{12}$ taken together form an oxygen atom.

The solvent employable here may include alcohols such as methanol, ethanol, n-propanol, isopropanol, n-butanol, isobutanol, t-butanol, isoamyl alcohol, diethylene glycol, glycerine, octanol, cyclohexanol and methyl cellosolve; and acetic acid; preferably alcohols (particularly ethanol).

The reducing agent employable here may include alkali metal boron hydrides such as lithium boron hydride; aluminum hydride compounds such as lithium aluminum hydride and lithium triethoxide aluminum hydride; and borane; preferably borane and lithium aluminum hydride.

The reaction temperature varies depending on the starting material, the solvent and the reducing agent but is usually from 0° C. to 50° C., preferably from 10° C. to 40° C.

The reaction time varies depending on the starting material, the solvent, the reducing agent and the reaction temperature but is usually from 10 minutes to 12 hours, preferably from 30 minutes to 5 hours.

After the reaction, the desired compound (3b) of the present reaction is obtained, for example, by decomposing the reducing agent, concentrating the reaction mixture, adding an organic solvent immiscible with water such as ethyl acetate, washing with water, separating an organic layer containing the desired compound, drying over anhydrous magnesium sulfate and distilling off the solvent.

The desired product thus obtained can be further purified, if necessary, by a conventional method, for example, recrystallization, silica gel column chromatography and the like.

(b) In the case where $R^{11}$ and $R^{12}$ are hydrogen atoms and $R^{10}$ is a group other than a benzyl group.

In the case where $R^{10}$ is a silyl group, the present step can be carried out according to the method of (3) of Step A-5.

In the case where $R^{10}$ is an aralkyl group such as a benzyl group; an alkoxyalkyl group such as a methoxymethyl group; an arylcarbonyloxymethyl group such as a benzoyloxymethyl group or an aralkyloxymethyl group such as a benzyloxymethyl group; and an alkoxyalkoxyalkyl group such as a methoxyethoxymethyl group, an acid catalyst is used and the acid catalyst used in this case may include an organic acid such as p-toluenesulfonic acid, trifluoroacetic acid and dichloroacetic acid and a Lewis acid such as $BF_3$ and $AlCl_3$.

The solvent employable here may include aromatic hydrocarbons such as benzene, toluene and xylene; halogenated hydrocarbons such as methylene chloride, chloroform, carbon tetrachloride, 1,2-dichloroethane, chlorobenzene and dichlorobenzene; nitriles such as acetonitrile and isobutyronitrile; amides such as formamide, N,N-dimethylformamide, N,N-dimethylacetamide, N-methyl-2-pyrrolidone, N-methylpyrrolidinone and hexamethylphosphoric triamide; and carbon sulfide.

The reaction temperature varies depending on the starting material, the solvent and the acid catalyst but is usually from 0° C. to 50° C., preferably from 10° C. to 40° C.

The reaction time varies depending on the starting material, the solvent, the acid catalyst and the reaction temperature and is usually from 10 minutes to 12 hours, preferably from 30 minutes to 5 hours.

After the reaction, the desired compound (3b) of the present reaction is obtained, for example, by neutralizing the reaction mixture, adding an organic solvent immiscible with water such as ethyl acetate, washing with water, separating an organic layer containing the desired compound, drying over anhydrous magnesium sulfate and distilling off the solvent.

The desired product thus obtained can be further purified, if necessary, by a conventional method, for example, recrystallization, silica gel column chromatography and the like.

Oligonucleotides containing a modified nucleoside or a thioate derivative thereof can be prepared by Process E described below using the compound (1) of the present invention.

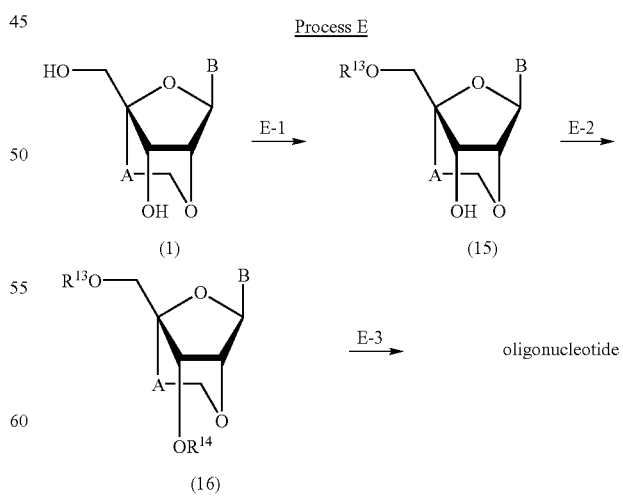

In Process E, A and B have the same meaning as defined above; $R^{13}$ represents a hydroxyl protecting group (particularly a trityl group which may be substituted by a methoxy group); $R^{14}$ represents a phosphonyl group or a group formed by reacting mono-substituted chloro(alkoxy)phosphines or di-substituted alkoxyphosphines described later.

(Process E)

(Step E-1)

The present step is to prepare the compound (15) by reacting the compound (1) prepared in Process A with a protecting reagent in an inert solvent.

The solvent employable here may preferably include aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; ketones such as acetone, methyl ethyl ketone, methyl isobutyl ketone, isophorone and cyclohexanone; nitrated compounds such as nitroethane and nitrobenzene; nitrites such as acetonitrile and isobutyronitrile; amides such as formamide, dimethylformamide (DMF), dimethylacetamide and hexamethylphosphoric triamide; sulfoxides such as dimethyl sulfoxide and sulfolane; aliphatic tertiary amines such as trimethylamine, triethylamine and N-methylmorpholine; and aromatic amines such as pyridine and picoline; more preferably halogenated hydrocarbons (particularly methylene chloride) and aromatic amines (particularly pyridine).

The protecting reagent employable here is not particularly limited so long as only the 5'-position can be selectively protected and it can be removed under acidic or neutral conditions but may preferably include triarylmethyl halides such as trityl chloride, monomethoxytrityl chloride and dimethoxytrityl chloride.

In the case where triarylmethyl halides are used as the protecting reagent, a base is usually used.

In such case, the base employable here may include heterocyclic amines such as pyridine, dimethylaminopyridine and pyrrolidinopyridine; and aliphatic tertiary amines such as trimethylamine and triethylamine; preferably pyridine, dimethylaminopyridine and pyrrolidinopyridine.

In the case where a liquid base is used as the solvent, since the base itself functions as an acid trapping agent, it is not necessary to add another base.

The reaction temperature varies depending on the starting material, the reagent and the solvent but is usually from 0° C. to 150° C., preferably from 20° C. to 100° C. The reaction time varies depending on the starting material, the solvent and the reaction temperature but is usually from 1 hour to 100 hours, preferably from 2 hours to 24 hours.

After the reaction, the desired compound (15) of the present reaction is obtained, for example, by concentrating the reaction mixture, adding an organic solvent immiscible with water such as ethyl acetate, washing with water, separating an organic layer containing the desired compound, drying over anhydrous magnesium sulfate and distilling off the solvent.

The desired product thus obtained can be further purified, if necessary, by a conventional method, for example, recrystallization, silica gel column chromatography and the like.

(Step E-2)

The present step is to prepare the compound (16) by reacting the compound (15) prepared in Step E-1 with mono-substituted chloro(alkoxy)phosphines or di-substituted alkoxyphosphines usually used for amidatation in an inert solvent.

The solvent employable here is not particularly limited so long as it does not affect the reaction and may preferably include ethers such as tetrahydrofuran, diethyl ether and dioxane; and halogenated hydrocarbons such as methylene chloride, chloroform, carbon tetrachloride, dichloroethane, chlorobenzene and dichlorobenzene.

The mono-substituted chloro(alkoxy)phosphines employable here may include phosphine derivatives such as chloro(morpholino)methoxyphosphine, chloro(morpholino)cyanoethoxyphosphine, chloro(dimethylamino)methoxyphosphine, chloro(dimethylamino)cyanoethoxyphosphine, chloro(diisopropylamino)methoxyphosphine and chloro(diisopropylamino)cyanoethoxyphosphine, preferably chloro(morpholino)methoxyphosphine, chloro(morpholino)cyanoethoxyphosphine, chloro(diisopropylamino)methoxyphosphine and chloro(diisopropylamino)cyanoethoxyphosphine.

In the case where the mono-substituted-chloro(alkoxy)phosphines are used, an acid trapping agent is used and in such case, the acid trapping agent employable here may include heterocyclic amines such as pyridine and dimethylaminopyridine; and aliphatic amines such as trimethylamine, triethylamine and diisopropylamine; preferably aliphatic amines (particularly diisopropylamine).

The di-substituted alkoxyphosphines employable here may include phosphine derivatives such as bis(diisopropylamino)cyanoethoxyphosphine, bis(diethylamino)methanesulfonylethoxyphosphine, bis(diisopropylamino)(2,2,2-trichloroethoxy)phosphine and bis(diisopropylamino)(4-chlorophenylmethoxy)phosphine, preferably bis(diisopropylamino)cyanoethoxyphosphine.

In the case where the di-substituted alkoxyphosphines are used, an acid is used, and in such case, the acid employable may preferably include tetrazole, acetic acid or p-toluenesulfonic acid.

The reaction temperature is not particularly limited but is usually from 0° C. to 80° C., preferably room temperature.

The reaction time varies depending on the starting material, the reagent and the reaction temperature, but is usually from 5 minutes to 30 hours, preferably from 30 minutes to 10 hours in the case where the reaction is carried out at room temperature.

After the reaction, the desired compound (16) of the present reaction is obtained, for example, by appropriately neutralizing the reaction mixture, removing insolubles by filtration in the case where they exist, adding an organic solvent immiscible with water such as ethyl acetate, washing with water, separating an organic layer containing the desired compound, drying over anhydrous magnesium sulfate and distilling off the solvent. The desired product thus obtained can be further purified, if necessary, by a conventional method, for example, recrystallization, reprecipitation or chromatography and the like.

Alternatively, the present step is to prepare the compound (16) by reacting the compound (15) prepared in Step E-1 with tris-(1,2,4-triazolyl)phosphite in an inert solvent (preferably halogenated hydrocarbons such as methylene chloride), followed by the addition of water to effect H-phosphonation.

The reaction temperature is not particularly limited, but is usually from −20° C. to 100° C., preferably from 10 to 40° C.

The reaction time varies depending on the starting material, the reagent and the reaction temperature and is usually from 5 minutes to 30 hours, preferably 30 minutes in the case where the reaction is carried out at room temperature.

After the reaction, the desired compound (16) of the present reaction is obtained, for example, by appropriately neutralizing the reaction mixture, removing insolubles by filtration in the case where they exist, adding an organic solvent immiscible with water such as ethyl acetate, washing with water, separating an organic layer containing the desired compound, drying over anhydrous magnesium sulfate and distilling off the solvent. The desired product thus obtained can be further purified, if necessary, by a conventional method, for example, recrystallization, reprecipitation or chromatography and the like.

(Step E-3)

In this step, the target oligonucleotide analogue is produced by an automated DNA synthesizer using at least one compound (16) prepared in step E-2 and commercially available phosphoramidite reagents required for producing an oligonucleotide analogue of a desired nucleotide sequence in accordance with conventional methods.

An oligonucleotide analogue having a desired nucleotide sequence can be synthesized by a DNA synthesizer such as the Perkin-Elmer Model 392 using the phosphoramidite method in accordance with the method described in the literature (Nucleic Acids Research, 12, 4539 (1984)).

In addition, in the case of converting to a thioate as desired, a thioate derivative can be obtained in accordance with the method described in the literature (*Tetrahedron Letters*, 32, 3005 (1991), *J. Am. Chem. Soc.*, 112, 1253 (1990)) using, besides sulfur, a reagent that forms a thioate by reacting with trivalent phosphoric acid such as tetraethylthiuram disulfide (TETD, Applied Biosystems Inc.) or Beaucage reagent (Millipore Corp.).

The resulting crude oligonucleotide analogue can be purified by OligoPak (reverse phase chromatocolumn) and the purity of the product can be confirmed by HPLC analysis.

The chain length of the resulting oligonucleotide analogue is normally 2 to 50 units, and preferably 10 to 30 units, in nucleoside units.

The complementary chain formation ability and nuclease enzyme resistance of the resulting oligonucleotide analogue can be determined according to the methods described below.

Test Method 1

The hybrid formation ability of the oligonucleotide analogue of the present invention with respect to complementary DNA and RNA can be determined by annealing the various resulting oligonucleotide analogues with an oligonucleotide analogue composed of naturally-occurring DNA or RNA having a complementary sequence and measuring the melting temperature (Tm value).

A sample solution containing equal amounts of oligonucleotide analogue and naturally-occurring complementary oligonucleotide in sodium phosphate buffer solution was put into a boiling water bath and then slowly cooled to room temperature over the course of time (annealing). The temperature of the solution was then raised little by little from 20° C. to 90° C. in the cell chamber of a spectrophotometer (e.g., Shimadzu UV-2100PC) followed by measurement of ultraviolet absorption at 260 nm.

Test Method 2 Measurement of Nuclease Enzyme Resistance

To the oligonucleotide in a buffer solution was added a nuclease and the mixture was warmed. Examples of nucleases that are used include snake venom phosphodiesterase, endonuclease P1 and endonuclease S1. Although there are no particular restrictions on the buffer solution provided it is a buffer solution suitable for enzymes, Tris-HCl buffer is used in the case of snake venom phosphodiesterase, while sodium acetate buffer is used in the case of endonuclease P1. In addition, metal ions are added to the buffer solution as necessary. Examples of metal ions used include $Mg^{2+}$ in the case of snake venom phosphodiesterase and $Zn^{2+}$ in the case of endonuclease. The reaction temperature is preferably 0 to 100° C., and more preferably 30 to 50° C.

Ethylenediamine tetraacetic acid (EDTA) is added after a predetermined amount of time followed by heating at 100° C. for 2 minutes in order to quench the reaction.

Examples of methods used to assay the amount of oligonucleotide remaining include a method in which the oligonucleotide is labelled with a radioisotope, etc. followed by assaying the cleavage reaction product with an image analyzer and so forth, a method in which the cleavage reaction product is assayed by reverse phase high-performance liquid chromatography (HPLC), and a method in which the cleavage reaction product is stained with a dye (such as ethidium bromide) and assayed by image processing using a computer.

Dosage forms of the oligonucleotide analogue having one, or two or more structures of the formula (2) of the present invention may be tablets, capsules, granules, powders or syrup for oral administration, or injections or suppositories for parenteral administration. These dosage forms are prepared by well-known methods using carriers such as excipients (for example, organic excipients such as sugar derivatives, e.g. lactose, sucrose, glucose, marmitol and sorbitol; starch derivatives, e.g. corn starch, potato starch, α-starch and dextrin; cellulose derivatives, e.g. crystalline cellulose; gum arabic; dextran; and Pullulan; and inorganic excipients such as silicate derivatives, e.g. light silicic anhydride, synthesized aluminium silicate, calcium silicate and magnesium aluminate metasilicate; phosphates, e.g. calcium hydrogenphosphate; carbonates, e.g. calcium carbonate; and sulfates, e.g. calcium sulfate), lubricants (for example, stearic acid, stearic acid metal salts such as calcium stearate and magnesium stearate; talc; colloidal silica; waxes such as bee gum and spermaceti; boric acid; adipic acid; sulfates, e.g. sodium sulfate; glycol; fumaric acid; sodium benzoate; DL-leucine; fatty acid sodium salt; laurylsulfates such as sodium laurylsulfate and magnesium laurylsulfate; silicic acids such as silicic anhydride and silicic acid hydrate; and the above starch derivatives), binders (for example, hydroxypropyl cellulose, hydroxypropyl methyl cellulose, polyvinyl pyrrolidone, Macrogol and compounds similar to the above excipients), disintegrants (for example, cellulose derivatives, such as low-substituted hydroxypropyl cellulose, carboxymethyl cellulose, calcium carboxymethyl cellulose and internally bridged sodium carboxymethyl cellulose; and chemically modified starch-celluloses such as carboxymethyl starch, sodium carboxymethyl starch and bridged polyvinyl pyrrolidone), stabilizers (paraoxybenzoates such as methylparaben and propylparaben; alcohols such as chlorobutanol, benzyl alcohol and phenylethyl alcohol; benzalkonium chloride; phenol derivatives such as phenol and cresol; thimerosal; dehydroacetic acid; and sorbic acid), corrigents (for example, sweeteners, souring agents, flavors, etc. usually used), diluents, etc.

More particularly, pharmaceutical compositions containing the active ingredient of the present invention may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the present invention may be in the form of a sterile injectable preparation, such as a sterile injectable aqueous or oleaginous suspension. This suspension may be formulated according to known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

While the dose for a particular patient will vary depending on a variety of factors including the activity of the specific compound or composition employed, the condition of the disease, the age, body weight, general health, sex and diet of the patient (e.g., warm blooded animals including humans), the time and route of administration, administration methods, the rate of excretion, other drugs which have been previously administered to the patient, the severity of the disease, etc. For example, in the case of oral administration, it is desirable to administer an active ingredient in an amount of from 0.01 mg/kg of body weight (preferably 0.1 mg/kg of body weight) to 1000 mg/kg of body weight (preferably 100 mg/kg of body weight) and in the case of intravenous administration, it is desirable to administer an active ingredient in an amount of from 0.001 mg/kg of body weight (preferably 0.01 mg/kg of body weight) to 100 mg/kg of body weight (preferably 10 mg/kg of body weight), as a single dose a day or in divided dose at several times for a day respectively.

EXAMPLES

Example 1

3',5'-di-O-Benzyl-2'-O,4'-C-ethylene-4-N-benzoylcytidine (Exemplification Compound Number 2-34)

An aqueous 2N sodium hydroxide solution (68 ml) was added to a solution of the compound obtained in Reference example 11 (6.80 g, 8.86 mmol) in pyridine (136 ml) at 0° C. and the mixture was stirred at room temperature for 1 hour. The reaction mixture was neutralized by dropwise addition of aqueous 20% acetic acid and extracted with chloroform. The chloroform layer was washed with saturated aqueous sodium chloride solution and concentrated in vacuo. The residue was purified by chromatography on a silica gel column (using dichloromethane:methanol=100:3 as the eluant) to afford the title compound (3.33 g, 6.02 mmol, 68%).

$^1$H-NMR (400 MHz, CDCl$_3$): 8.64 (2H, brs), 7.89 (2H, d, 7.6 Hz), 7.64-7.60 (1H, m) 7.54-7.51 (2H, m), 7.48-7.37 (3H, m), 7.36-7.26 (8H, m), 6.18 (1H, s), 4.70 (1H, d, 11 Hz), 4.60 (1H, d, 11 Hz), 4.55 (1H, d, 11 Hz), 4.46 (1H, d, 2.9 Hz), 4.42 (1H, d, 11 Hz), 4.10-4.02 (2H, m), 3.89 (1H, d, 2.9 Hz), 3.75 (1H, d, 11 Hz), 3.62 (1H, d, 11 Hz), 2.34-2.26 (1H, m), 1.39-1.36 (1H, m).

FAB-MAS(mNBA):554(M+H)$^+$

Example 2

2'-O,4'-C-ethylene-4-N-benzoylcytidine (Exemplification Compound Number 2-225)

A solution (31.7 ml) of 1.0 M trichloroborane in dichloromethane was added dropwise to a solution of the compound obtained in Example 1 (2.06 g, 3.72 mmol) in anhydrous methylenechloride (317 ml) at −78° C. and the mixture was stirred at −78° C. for 1 hour. The reaction mixture was slowly warmed to −20° C. and the reaction vessel was placed into an ice-sodium chloride bath and the mixture was stirred at between −20° C. and −10° C. for 2 hours. Methanol (12 ml) was slowly added to the mixture and the mixture was stirred for 10 minutes. The pH of the reaction mixture was adjust to 7-8 by dropwise addition of saturated aqueous sodium hydrogencarbonate solution. The mixture was warmed to room temperature and concentrated in vacuo. The residue was purified by chromatography on a silica gel column (using dichloromethane:methanol=100:5 as the eluant) to afford the title compound (1.21 g, 3.24 mmol, 87%) as a white solid.

$^1$H-NMR (500 MHz, DMSO-d$_6$): 11.23 (1H, brs), 8.70 (1H, d, 7.2 Hz), 8.00 (2H, d, 7.5 Hz), 7.3-6 (4H, m), 5.97 (1H, s), 5.35 (1H, dd, 5 and 10 Hz), 4.10 (1H, dd, 5 and 10 Hz), 4.03 (1H, d, 3.2 Hz), 3.95-3.85 (2H, m) 3.83 (1H, d, 3.2 Hz), 3.65-3.51 (2H, m), 2.06-1.98 (1H, m), 1.26 (1).

FAB-MAS(mNBA):374(M+H)$^+$

Example 3

2'-O,4'-C-ethylene-cytidine (Exemplification Compound Number 2-3)

A solution of the compound obtained in Example 2 (0.1 g, 0.268 mmol) in methanol saturated with ammonia (12 ml) was allowed to stand overnight. The mixture was concentrated to dryness to afford the title compound (0.054 g, 75%) as a white solid.

$^1$H-NMR (500 MHz, DMSO-d$_6$): 8.18 (1H, d, 7.4 Hz), 7.10 (2H, br), 5.84 (1H, s), 5.69 (1H, d, 7.6 Hz), 5.27-5.24 (2H, m), 3.86 (1H, d, 3.2Hz), 3.90-3.78 (2H, m), 3.76 (1H, d, 3.2 Hz), 3.56 (1H, dd, 5.5 and 12 Hz), 3.49 (1H, dd, 5.5 and 12 Hz), 2.01-1.93 (1H, dt, 7.5 and 12 Hz), 1.22 (1H, dd, 3.6 and 13 Hz).

FAB-MAS(mNBA):270(M+H)$^+$

Example 4

5'-O-Dimethoxytrityl-2'-O,4'-C-ethylene-4-N-benzoylcytidine (Exemplification Compound Number 2-39)

A solution of the compound obtained in Example 2 (1.29 g, 3.46 mmol) in anhydrous pyridine was azeotropically refluxed in order to remove water. The product was dissolved in anhydrous pyridine (26 ml) under nitrogen atmosphere and 4,4'-dimethoxytritylchloride (1.76 g, 5.18 mmol) was added to the solution and the mixture was stirred at room temperature overnight. A small amount of methanol was added to the reaction mixture and then the solvent was evaporated in vacuo. The residue was partitioned between water and chloroform and the organic layer was washed with saturated aqueous sodium hydrogencarbonate solution and saturated aqueous sodium chloride solution and concentrated in vacuo. The residue was purified by chromatography on a silica gel column (using dichloromethane:methanol=100:5 as the eluant) to afford the title compound (2.10 g, 3.11 mmol, 90%) as a colorless amorphous solid.

$^1$H-NMR (270 MHz, DMSO-d$_6$): 11.27 (1H, brs), 8.59 (1H, m), 6.92-8.01 (19H, m), 6.03 (1H, s), 5.56 (1H, m), 4.17 (1H, m), 4.08 (1H, m), 3.86 (2H, m), 3.77 (6H, s), 3.24 (2H, m), 1.98 (1H, m), 1.24 (1H, m). FAB-MAS(mNBA): 676(M+H)$^+$ Example 5

5'-O-Dimethoxytrityl-2'-O,4'-C-ethylene-4-N-benzoylcytidine-3'-O-(2-cyanoethyl N,N-diisopropyl)phosphoramidite (Exemplification Compound Number 2-235)

A solution of the compound obtained in Example 4 (6.53 g, 9.66 mmol) in anhydrous pyridine was azeotropically refluxed in order to remove water. The product was dissolved under nitrogen atmosphere in anhydrous dichloromethane (142 ml). N,N-diisopropylamine (2.80 ml, 16.1 mmol) was added to the solution and then 2-cyanoethyl N,N-diisopropylchlorophophoramidite (2.16 ml, 9.66 mmol) was added dropwise in an ice bath. The mixture was stirred at room temperature for 6 hours. The reaction mixture was washed with saturated aqueous sodium hydrogencarbonate solution and saturated aqueous sodium chloride solution and concentrated in vacuo. The residue was purified by chromatography on a silica gel column (using dichloromethane:triethylamine=50:1-dichloromethane:ethyl acetate:triethylamine=60:30:1 as the eluant) to afford the title compound (7.10 g, 8.11 mmol, 84%) as a pale white compound.

$^1$H-NMR (400 MHz, CDCl$_3$): 1.1-1.2 (12H, m), 1.35 (1H, m), 2.11 (1H, m), 2.3 (2H, m), 3.35-3.7 (6H, m), 3.8 (6H, m), 3.9-4.1 (2H, m), 4.33 (1H, m), 4.45 (1H, m), 6.23 (1H, s), 6.9 (4H, m), 7.3-7.9 (15H, m), 8.7-8.8 (1H, m).

Example 6

3',5'-Di-O-benzyl-2'-O,4'-C-ethylene-5-methyluridine (Exemplification Compound Number 2-22)

An aqueous 2N sodium hydroxide solution (5 ml) and mixture solution (5 ml), said mixture solution comprised of pyridine:methanol:water=65:30:5, were added to the compound obtained in Reference example 10 (418 mg, 0.62 mmol) in pyridine:methanol:water=65:30:5 (5 ml) at 0° C. and the mixture was stirred at room temperature for 15 minutes. The reaction mixture was neutralized with 1N hydrochloric acid and extracted with ethyl acetate (about 30 ml). The organic layer was washed with saturated aqueous sodium hydrogencarbonate solution (about 30 ml) and saturated aqueous sodium chloride solution (about 30 ml), dried over anhydrous magnesium sulfate and then concentrated in vacuo. The residue was purified by chromatography on a silica gel column (using hexane:ethyl acetate=1:1 as the eluant) to afford a colorless amorphous solid (228 mg, 0.49 mmol, 79%).

$^1$H-NMR (400 MHz, CDCl$_3$): 1.35 (1H, d, 13 Hz), 1.41 (3H, s), 2.28 (1H, dt, 9.4 and 13 Hz), 3.60 (1H, d, 11 Hz), 3.76 (1H, d, 11 Hz), 3.94 (1H, d, 3.0 Hz), 4.10 (1H, d, 7.0 Hz), 4.14 (1H, d, 7.0 Hz), 4.31 (1H, d, 3.0 Hz), 4.51 (1H, d, 12 Hz), 4.54 (1H, d, 12 Hz), 4.58 (1H, d, 12 Hz), 4.75 (1H, d, 12 Hz), 6.06 (1H, s), 7.3 (10H, m), 7.91 (1H, s,), 8.42 (1H, brs).

FAB-MAS(mNBA):465(M+H)$^+$

Example 7

2'-O,4'-C-ethylene-5-methyluridine (Exemplification Compound Number 2-2)

A solution of the compound obtained in Example 6 (195 mg, 0.42 mmol) in methanol (10 ml) was stirred under hydrogen atmosphere at atmospheric pressure in the presence of 160 mg of 20% Pd(OH)$_2$ on carbon as a hydrogenation catalyst for 5 hours. The reaction mixture was filtered in order to remove catalyst and the filtrate was concentrated in vacuo. The residue was purified by chromatography on a silica gel column (using dichloromethane:methanol=10:1 as the eluant) to afford a colorless powder (76 mg, 0.268 mmol, 64%).

$^1$H-NMR (400 MHz, CD$_3$OD): 1.33 (1H, dd, 3.8 and 13 Hz), 1.86 (3H, d, 0.9 Hz), 1.94 (1H, ddd, 7.5, 11.7 and 13 Hz), 3.68 (1H, d, 12 Hz), 3.75 (1H, d, 12 Hz), 3.9-4.0 (2H, m), 4.05 (1H, d, 3.2 Hz), 4.09 (1H, d, 3.2 Hz), 6.00 (1H, s), 8.28 (1H, d, 1.1 Hz)

FAB-MAS(mNBA):285(M+H)$^+$

Example 8

5'-O-Dimethoxytrityl-2'-O,4'-C-ethylene-5-methyluridine (Exemplification Compound Number 2-27)

A solution of the compound obtained in Example 7 (1.45 g, 5.10 mmol) in anhydrous pyridine was azeotropically refluxed in order to remove water. The product was dissolved in anhydrous pyridine (44 ml) under nitrogen atmosphere and 4,4'-dimethoxytritylchloride (2.59 g, 7.65 mmol) was added to the solution and the mixture was stirred at room temperature overnight. A small amount of methanol was added to the reaction mixture and then the solvent was evaporated in vacuo. The residue was partitioned between water and chloroform and the organic layer was washed with saturated aqueous sodium hydrogencarbonate solution and saturated aqueous sodium chloride solution and concentrated in vacuo. The residue was purified by chromatography on a silica gel column (using dichloromethane:methanol=100:10 as the eluant) to afford the title compound (2.42 g, 4.13 mmol, 81%) as colorless amorphous solid.

$^1$H-NMR (270 MHz, DMSO-d$_6$): 11.36 (1H, s), 7.68 (1H, s), 6.90-7.44 (13H, m), 5.89 (1H, s), 5.55 (1H, d), 4.09 (1H, m), 4.04 (1H, d), 3.82 (2H, m), 3.74 (6H, s), 3.19 (2H, m), 1.99 (1H, m), 1.36 (1H, m), 1.17 (3H, s).

FAB-MAS(mNBA):587(M+H)$^+$

Example 9

5'-O-Dimethoxytrityl-2'-O,4'-C-ethylene-5-methyluridine-3'-O-(2-cyanoethyl N,N-diisopropyl)phosphoramidite (Exemplification Compound Number 2-234)

A solution of the compound obtained in Example 8 (4.72 g, 8.05 mmol) in anhydrous pyridine was azeotropically refluxed in order to remove water. The product was dissolved under nitrogen atmosphere in anhydrous dichloromethane (142 ml). N,N-diisopropylamine (2.80 ml, 16.1 mmol) was added to the solution and then 2-cyanoethyl N,N-diisopropylchlorophophoramidite (2.16 ml, 9.66 mmol) was added dropwise in an ice bath. The mixture was stirred at room temperature for 6 hours. The reaction mixture was washed with saturated aqueous sodium hydrogencarbonate solution and saturated aqueous sodium chloride solution and concentrated in vacuo. The residue was purified by chromatography on a silica gel column (using hexane:ethyl acetate:triethylamine=50:50:1-hexane:ethyl acetate:triethylamine=30:60:1 as the eluant) to afford the title compound (5.64 g, 7.17 mmol, 89%) as a colorless amorphous solid.

$^1$H-NMR (400 MHz, CDCl$_3$): 1.1-1.2 (15H, m), 1.4 (1H, m), 2.08 (1H, m), 2.4 (2H, m), 3.2-4.0 (14H, m), 4.38 (2H, m), 4.47 (1H, m), 6.06 (1H, s), 6.8-6.9 (4H, m), 7.2-7.5 (9H, m), 7.91 (1H, m).

FAB-MAS(mNBA):787(M+H)$^+$

Example 10

3',5'-Di-O-benzyl-2'-O,4'-C-ethylene-6-N-benzoyladenosine (Exemplification Compound Number 1-23)

An aqueous 2N sodium hydroxide solution (5 ml) and mixture solution (5 ml), said mixture solution comprised of pyridine:methanol:water=65:30:5, were added to compound obtained in Reference example 12 (238 mg, 0.30 mmol) in pyridine:methanol:water=65:30:5 (5 ml) at 0° C. and the mixture was stirred at room temperature for 15 minutes. The reaction mixture was neutralized with 1N hydrochloric acid and extracted with ethyl acetate (about 30 ml). The organic layer was washed with saturated aqueous sodium hydrogencarbonate solution (about 30 ml) and saturated aqueous sodium chloride solution (about 30 ml), dried over anhydrous magnesium sulfate and then concentrated in vacuo. The residue was purified by chromatography on a silica gel column (using dichloromethane:methanol=50:1 as the eluant) to afford a colorless amorphous solid (133 mg, 0.23 mmol, 78%).

$^1$H-NMR (400 MHz, CDCl$_3$): 1.44 (1H, d, 13 Hz), 2.31 (1H, dd, 13 and 19 Hz), 3.56 (1H, d, 11 Hz), 3.70 (1H, d, 11 Hz), 4.10 (2H, m), 4.24 (1H, s), 4.45 (11 H, d, 12 Hz), 4.53-4.67 (4H, m), 6.52 (1H, s), 7.3 (10H, m), 7.53 (2H, m), 7.62 (1H, m), 8.03 (2H, d, 7.6 Hz), 8.66 (1H, s), 8.78 (1H, s), 9.00 (1H, brs).

FAB-MAS(mNBA):578(M+H)$^+$

Example 11

2'-O,4'-C-Ethylene-6-N-benzoyladenosine (Exemplification Compound Number 1-178)

A 1M boron trichloride solution (1.5 ml, 1.5 mmol) in dichloromethane was slowly added dropwise to a solution of the compound obtained in Example 10 (116 mg, 0.20 mmol) in anhydrous methylenechloride (5 ml) at −78° C. and the mixture was stirred at −78° C. for 3 hours. To the reaction mixture was added a 1M boron trichloride solution (1.5 ml, 1.5 mmol) in dichloromethane and the mixture was stirred for 2 hours. The mixture was slowly warmed to room temperature and then quickly cooled to −78° C. and then methanol (5 ml) was added to the mixture. The reaction mixture was slowly warmed to room temperature and concentrated in vacuo. The residue was purified by chromatography on a silica gel column (using dichloromethane:methanol=9:1 as the eluant) to afford a white powder (49 mg, 0.17 mmol, 84%).

$^1$H-NMR (400 MHz, CD$_3$OD): 1.45 (1H, dd, 4.3 and 13 Hz), 2.12 (1H, m), 3.72 (1H, d, 12 Hz), 3.79 (1H, d, 12 Hz), 4.04 (1H, dd, 7.3 and 12 Hz), 4.15 (1H, dt, 4.3 and 9.4 Hz), 4.36 (1H, d, 3.2 Hz), 4.43 (1H, d, 3.2 Hz), 6.57 (1H, s), 7.57 (2H, m), 7.66 (1H, m), 8.09 (2H, d, 8.0 Hz), 8.72 (1H, s), 8.85 (1H, s).

FAB-MAS(mNBA):398(M+H)$^+$

Example 12

2'-O,4'-C-Ethyleneadenosine (Exemplification Compound Number 1-7)

A solution of the compound obtained in Example 11 (14 mg, 0.035 mmol) in methanol saturated with ammonia (1 ml) was allowed to stand overnight. The mixture was concentrated and the residue was purified by chromatography on a silica gel column (using dichloromethane:methanol=10:1 as the eluant) to afford a white powder (10 mg, 0.034 mmol, 98%).

$^1$H-NMR (400 MHz, CD$_3$OD): 1.32 (1H, dd, 4 and 13 Hz), 2.04 (1H, dt, 7.4 and 12 Hz), 3.53 (1H, dd, 5 and 12 Hz), 3.61 (1H, dd, 5.2 and 12 Hz), 3.90 (1H, dd, 7.4 and 12 Hz), 3.97 (1H, dt, 4 and 12 Hz), 4.15 (1H, d, 3.1 Hz), 4.21 (1H, d, 3.1 Hz), 5.27 (1H, t, 5.2 Hz), 5.39 (1H, d, 3.1 Hz), 6.33 (1H, s), 7.29 (2H, s), 7.66 (1H, m), 8.14 (1H, s), 8.42 (1H, s), FAB-MAS(mNBA):294(M+H)$^+$ UV($\lambda$max): 260 (pH7), 260 (pH1), 258 (pH13)

Example 13

5'-O-Dimethoxytrityl-2'-O,4'-C-ethylene-6-N-benzoyladenosine (Exemplification Compound Number 1-31)

A solution of the compound obtained in Example 11 (14 mg, 0.035 mmol) in anhydrous pyridine was azeotropically refluxed in order to remove water. The product was dissolved in anhydrous pyridine (1 ml) under nitrogen atmosphere and 4,4'-dimethoxytritylchloride (18 mg, 0.053 mmol) was added to the solution and the mixture was stirred at 40° C. for 5 hours. A small amount of methanol was added to the reaction mixture and then the solvent was evaporated in vacuo. The residue was partitioned between water and chloroform and the organic layer was washed with saturated aqueous sodium hydrogencarbonate solution and saturated aqueous sodium chloride solution and concentrated in vacuo. The residue was purified by chromatography on a silica gel column (using dichloromethane:methanol=100:5 as the eluant) to afford the title compound (18 mg, 0.026 mmol, 73%) as a colorless amorphous solid.

$^1$H-NMR (400 MHz, CDCl$_3$): 1.63 (1H, m), 2.14 (1H, 7.5, 12, and 13 Hz), 3.37 (1H, d, 11 Hz), 3.41 (1H, d, 11 Hz), 3.79 (6H, s), 4.10 (2H, m), 4.48 (1H, d, 3.3 Hz), 4.59 (1H, d, 3.3 Hz), 6.54 (1H, s), 6.85 (4H, m), 7.2-7.6 (12H, m), 8.02 (2H, m), 8.45 (1H, s), 8.82 (1H, s), 9.02 (1H, brs). FAB-MAS(mNBA):700(M+H)$^+$

Example 14

5'-O-Dimethoxytrityl-2'-O,4'-C-ethylene-6-N-benzoyladenosine-3'-O-(2-cyanoethyl N,N-diisopropyl) phosphoramidite (Exemplification Compound Number 1-186)

A solution of the compound obtained in Example 13 (16 mg, 0.023 mmol) in anhydrous pyridine was azeotropically refluxed in order to remove water. The product was dissolved under nitrogen atmosphere in anhydrous dichloromethane (0.5 ml). Tetrazole N,N-diisopropylamine salt (10 mg) was added to the solution and then 2-cyanoethyl N,N,N',N'-tetraisopropylphophoramidite (about 20 μl) was added dropwise in an ice bath. The mixture was stirred at room temperature overnight. The reaction mixture was washed with saturated aqueous sodium hydrogencarbonate solution and saturated aqueous sodium chloride solution and concentrated in vacuo. The residue was purified by chromatography on a silica gel column (using dichloromethane:ethyl acetate=2:1 as the eluant) to afford the title compound (20 mg, 0.022 mmol, 97%) as a white solid.

$^1$H-NMR (400 MHz, $CDCl_3$): 1.0-1.2 (12H, m), 1.54 (1H, m), 2.15 (1H, m), 2.33 (2H, m), 3.3-3.6 (6H, m), 3.80 (6H, s), 4.08 (2H, m), 4.65 (1H, m), 4.75 (1H, m), 6.53 (1H, s), 6.84 (4H, m), 7.2-7.6 (12H, m), 8.01 (2H, m), 8.53 (1H, s), 8.83 (1H, s), 9.01 (1H, brs).

FAB-MAS(mNBA):900(M+H)$^+$

Example 15

3',5'-Di-O-benzyl-2'-O,4'-C-ethyleneuridine (Exemplification Compound Number 2-10)

An aqueous 1N sodium hydroxide solution (2 ml) was added to a solution of the compound obtained in Reference example 13 (194 mg, 0.292 mmol) in pyridine (3 ml) at 0° C. and the mixture was stirred at room temperature for 30 minutes. The reaction mixture was neutralized with 1N hydrochloric acid and extracted with ethyl acetate (10 ml). The organic layer was washed with saturated aqueous sodium hydrogencarbonate solution and saturated aqueous sodium chloride solution, dried over anhydrous magnesium sulfate and then concentrated in vacuo. The residue was purified by chromatography on a silica gel column (using dichloromethane:methanol=100:3 as the eluant) to afford an colorless oil (105 mg, 0.233 mmol, 80%).

hu 1H-NMR (400 MHz, $CDCl_3$): 1.36 (1H, m), 2.29 (1H, m), 3.63 (1H, d, 11 Hz), 3.74 (1H, d, 11 Hz), 3.87 (1H, d, 2.9 Hz), 4.03 (2H, m), 4.29 (1H, d, 2.9 Hz), 4.49 (1H, d, 12 Hz), 4.50 (1H, d, 11 Hz), 4.53 (1H, d, 11 Hz), 4.73 (1H, d,12 Hz), 5.20 (1H, dd, 2 and 8 Hz), 6.04 (1H, s), 7.2-7.4 (10H, m), 8.13 (1H, d, 8.2 Hz), 8.57 (1H, brs).

FAB-MAS(mNBA):451(M+H)$^+$

Example 16

2'-O,4'-C-Ethyleneuridine (Exemplification Compound Number 2-1)

A solution of the compound obtained in Example 15 (100 mg, 0.222 mmol) in methanol (4 ml) was stirred under hydrogen atmosphere at atmospheric pressure in the presence of 90 mg of 20% Pd(OH)$_2$ on carbon as a hydrogenation catalyst for 5 hours. The reaction mixture was filtered in order to remove catalyst and the filtrate was concentrated in vacuo. The residue was purified by chromatography on a silica gel column (using dichloromethane:methanol=10:1 as the eluant) to afford a colorless oil (45 mg, 0.167 mmol, 75%).

$^1$H-NMR (400 MHz, $CD_3OD$): 1.35 (1H, dd, 4 and 13 Hz), 2.13 (1H, ddd, 7, 11 and 13 Hz), 3.66 (1H, d, 12 Hz), 3.73 (1H, d, 12 Hz), 3.91-4.08 (2H, m),4.01 (1H, d, 3.2 Hz), 4.12 (1H, d, 3.2 Hz), 5.66 (1H, d, 8.2 Hz), 6.00 (1H, s), 8.37 (1H, d, 8.2 Hz).

FAB-MAS(mNBA):271(M+H)$^+$

Example 17

5'-O-Dimethoxytrityl-2'-O,4'-C-ethyleneuridine (Exemplification Compound Number 2-15)

A solution of the compound obtained in Example 16 (28 mg, 0.104 mmol) in anhydrous pyridine was azeotropically refluxed in order to remove water. The product was dissolved in anhydrous pyridine (3 ml) under nitrogen atmosphere and 4,4'-dimethoxytritylchloride (50 mg, 0.15 mmol) was added to the solution and the mixture was stirred at room temperature overnight. A small amount of methanol was added to the reaction mixture and then the solvent was evaporated in vacuo. The residue was partitioned between water and chloroform and the organic layer was washed with saturated aqueous sodium hydrogencarbonate solution and saturated aqueous sodium chloride solution and concentrated in vacuo. The residue was purified by chromatography on a silica gel column (using dichloromethane:methanol=100:3 as the eluant) to afford the title compound (25 mg, 0.044 mmol, 42%) as a colorless oil.

$^1$H-NMR (400 MHz, $CD_3OD$): 1.35 (1H, dd, 3 and 14 Hz), 2.03 (1H, ddd, 8, 11 and 14 Hz), 2.46 (1H, d, 8 Hz), 3.36 (1H, d, 11 Hz), 3.41 (1H, d, 11 Hz), 3.80(3H, s), 3.81 (3H, s), 3.97 (2H, m), 4.21 (1), 4.33 (1H, brm), 5.31 (1H, m), 6.10 (1H, s), 6.86 (4H, m), 7.2-7.5 (9H, m), 8.27 (1H, d, 8.2 Hz), 8.43 (1H, brs).

FAB-MAS (mNBA): 573 (M+H)$^+$

Example 18

5'-O-Dimethoxytrityl-2'-O,4'-C-ethyleneuridine-3'-O-(2-cyanoethyl N,N-diisopropyl)phosphoramidite (Exemplification Compound Number 2-233)

A solution of the compound obtained in Example 17 (6 mg, 0.0105 mmol) in anhydrous pyridine was azeotropically refluxed in order to remove water. The product was dissolved under nitrogen atmosphere in anhydrous dichloromethane (0.5 ml). Tetrazole N,N-diisopropylamine salt (3 mg) was added to the solution and then 2-cyanoethyl N,N, N',N'-tetraisopropylphophoramidite (about 5 μl) was added dropwise in an ice bath. The mixture was stirred at room temperature overnight. The reaction mixture was washed with saturated aqueous sodium hydrogencarbonate solution and saturated aqueous sodium chloride solution and concentrated in vacuo. The residue was purified by chromatography on a silica gel column (using dichloromethane:ethyl acetate=2:1 as the eluant) to afford the title compound (8 mg) as a white solid.

$^1$H-NMR (400 MHz, $CDCl_3$): 1.1-1.2 (13H, m), 2.09 (1H, m), 2.4 (2H, m), 3.3 (6H, m), 3.81 (6H, m), 3.94 (2H, m), 4.35 (1H, m), 4.47 (1H, m), 5.18 (1H, d, 8.2 Hz), 6.08 (1H, s), 6.86 (4H, m), 7.2-7.4 (9H, m), 8.31 (1H, d, 8.2 Hz).

FAB-MAS (mNBA): 773 (M+H)+

Example 19

3',5'-Di-O-benzyl-2'-O,4'-C-ethylene-4-N-benzoyl-5-methylcytidine (Exemplification Compound Number 2-46)

An aqueous 1N sodium hydroxide solution (5 ml) was added to a solution of the compound obtained in Reference example 14 (310 mg, 0.396 mmol) in pyridine (5 ml) at 0° C. and the mixture was stirred at room temperature for 20 minutes. The reaction mixture was neutralized by dropwise addition of aqueous 20% acetic acid and extracted with dichloromethane. The dichloromethane layer was washed with saturated aqueous sodium chloride solution and concentrated in vacuo. The residue was purified by chromatography on a silica gel column (using dichloromethane:methanol=100:2 as the eluant) to afford the title compound (190 mg, 0.334 mmol, 84%).

$^1$H-NMR (400 MHz, CDCl$_3$): 1.37 (1H, m), 1.58 (3H, s), 2.30 (1H, dt, 10 and 13 Hz), 3.64 (1H, d, 11 Hz), 3.79 (1H, d, 11 Hz), 3.95 (1H, d, 3.0 Hz), 4.04 (2H, dd, 2.3 and 10 Hz), 4.37 (1H, d, 3.0 Hz), 4.50 (1H, d, 12 Hz), 4.56 (1H, d, 11 Hz), 4.61 (1H, d, 11 Hz), 4.76 (1H, d, 12 Hz), 6.11 (1H, s), 7.2-7.5 (13H, m), 8.09 (1H, s), 8.29 (2H, m).

FAB-MAS (mNBA): 568 (M+H)+

Example 20

2'-O,4'-C-Ethylene-4-N-benzoyl-5-methylcytidine (Exemplification Compound Number 2-226)

A 1M boron trichloride solution (1.6 ml) in dichloromethane was added dropwise to a solution of the compound obtained in Example 19 (120 mg, 0.211 mmol) in anhydrous dichloromethane (5 ml) at −78° C. and the mixture was stirred at −78° C. for 4 hours. Methanol (1 ml) was slowly added dropwise to the mixture and the mixture was stirred for 10 minutes. The pH of the reaction mixture was adjusted to 7-8 by dropwise addition of saturated aqueous sodium hydrogencarbonate solution. The reaction mixture was warmed to room temperature and concentrated in vacuo. The residue was purified by chromatography on a silica gel column (using dichloromethane:methanol=100:6 as the eluant) to afford the title compound (29 mg, 0.075 mmol, 36%) as a white solid.

$^1$H-NMR (400 MHz, d-DMSO): 1.24 (1H, m), 2.01 (3H, s), 2.0 (1H, m), 3.54 (1H, dd, 5.4 and 12 Hz), 3.64 (1H, dd, 5.4 and 12 Hz), 3.88 (3H, m), 4.10 (1H, m), 5.36 (1H, d, 5.4 Hz), 5.49 (1H, t, 5.0 Hz), 5.95 (1H, s), 7.4-7.6 (3H, m), 8.21 (2H, m), 8.49 (1H, s), 13.17 (1H, brs).

FAB-MAS (mNBA): 388 (M+H)+

Example 21

5'-O-Dimethoxytrityl-2'-O,4'-C-ethylene-4-N-benzoyl-5-methylcytidine (Exemplification Compound Number 2-51)

A solution of the compound obtained in Example 20 (44 mg, 0.114 mmol) in anhydrous pyridine was azeotropically refluxed in order to remove water. The product was dissolved in anhydrous pyridine (1 ml) under nitrogen atmosphere and 4,4'-dimethoxytritylchloride (60 mg, 0.177 mmol) was added to the solution and the mixture was stirred at room temperature overnight. A small amount of methanol was added to the reaction mixture and then the solvent was evaporated in vacuo. The residue was partitioned between water and chloroform. The organic layer was washed with saturated aqueous sodium hydrogencarbonate solution and saturated aqueous sodium chloride solution and concentrated in vacuo. The residue was purified by chromatography on a silica gel column (using dichloromethane:methanol=100:4 as the eluant) to afford the title compound (73 mg, 0.106 mmol, 93%) as a colorless oil.

$^1$H-NMR (400 MHz, CDCl$_3$): 1.46 (1H, m), 1.49 (3H, s), 2.06 (1H, m), 2.59 (1H, d, 8.6 Hz), 3.36 (1H, d, 11 Hz), 3.39 (1H, d, 11 Hz), 3.80 (3H, s), 3.81 (3H, s), 3.99 (2H, m), 4.30 (1H, d, 3.3 Hz), 4.39 (1H, m), 6.12 (1H, s), 6.85 (4H, m), 7.2-7.5 (12H, m), 8.03 (1H, s), 8.28 (2H, m).

FAB-MAS (mNBA): 573 (M+H)+

Example 22

5'-O-Dimethoxytrityl-2'-O,4'-C-ethylene-4-N-benzoyl-5-methylcytidine-3'-O-(2-cya noethyl N,N-diisopropyl)phosphoramidite (Exemplification Compound Number 2-236)

A solution of the compound obtained in Example 21 (35 mg, 0.0507 mmol) in anhydrous pyridine was azeotropically refluxed in order to remove water. The product was dissolved under nitrogen atmosphere in anhydrous dichloromethane (1 ml). Tetrazole N,N-diisopropylamine salt (17 mg) was added to the solution and then 2-cyanoethyl N,N,N',N'-tetraisopropylphophoramidite (32 μl, 0.1 mmol) was added dropwise in an ice bath. The mixture was stirred at room temperature overnight. The reaction mixture was washed with saturated aqueous sodium hydrogencarbonate solution and saturated aqueous sodium chloride solution and concentrated in vacuo. The residue was purified by chromatography on a silica gel column (using dichloromethane:ethyl acetate=2:1 as the eluant) to afford the title compound (40 mg, 0.0445 mmol, 89%) as a white solid.

$^1$H-NMR (400 MHz, CDCl$_3$): 1.1-1.2 (12H, m), 1.36 (3H, s), 1.37 (1H, m), 2.10 (1H, m), 2.36 (2H, m), 3.3-3.6 (6H, m), 3.81 (6H, m), 3.98 (2H, m), 4.42 (1H, m), 4.49 (1H, m), 6.11 (1H, s), 6.88 (4H, m), 7.2-7.5 (12H, m), 8.14 (1H, s), 8.28 (2H, m).

FAB-MAS (mNBA): 890 (M+H)30

Example 23

2'-O,4'-C-Ethylene-5-methylcytidine (Exemplification Compound Number 2-226)

A solution of the compound obtained in Example 20 (11.6 mg, 0.030 mmol) in methanol saturated with ammonia (2 ml) was allowed to stand overnight. The mixture was concentrated to afford a white solid (8.5 mg, 0.030 mmol).

$^1$H-NMR (400 MHz, d-DMSO): 1.20 (1H, m), 1.82 (3H, s), 1.97 (1H, m), 3.49 (1H, dd, 5 and 12 Hz), 3.58 (1H, dd, 5 and 12 Hz), 3.85 (2H, m), 5.23 (1H, d, 5 Hz), 5.32 (1H, t, 5 Hz), 5.84 (1H, s), 6.7 (1H, brs), 7.2 (1H, brs), 8.08 (1H, s).

FAB-MAS (mNBA): 284 (M+H)+

UV(λmax): 279(pH7), 289(pH1), 279 (pH13)

Example 24

3',5'-Di-O-benzyl-2'-O,4'-C-ethylene-2-N-isobutyrylguanosine (Exemplification Compound Number 1-24)

An aqueous 1N sodium hydroxide solution (2 ml) was added to a solution of the compound obtained in Reference example 15 (about 200 mg) in pyridine (2 ml) and the mixture was stirred at room temperature for 15 minutes. The reaction mixture was neutralized with 1N hydrochloric acid and extracted with ethyl acetate. The organic layer was washed with saturated aqueous sodium hydrogencarbonate solution and saturated aqueous sodium chloride solution, dried over anhydrous magnesium sulfate and then concentrated in vacuo. The residue was purified by chromatography on a silica gel column (using dichloromethane:methanol=50:1 as the eluant) to afford a colorless amorphous solid (20 mg, 0.036 mmol, 6%, 2 steps).

$^1$H-NMR (400 MHz, CDCl$_3$): 1.27 (3H, s), 1.29 (3H, s), 1.43 (1H, dd, 3 and 13 Hz), 2.28 (1H, m), 2.59 (1H, qui, 6.9 Hz), 3.54 (1H, d, 11 Hz), 3.68 (1H, d, 11 Hz), 4.03 (2H, m), 4.15 (1H, d, 3.0 Hz), 4.31 (1H, d, 3.0 Hz), 4.45 (1H, d, 12), 4.56 (1H, d, 12 Hz), 4.61 (1H, d, 12 Hz), 4.63 (1H, d, 12 Hz), 6.18 (1H, s), 7.2-7.4 (10H, m), 8.19 (1H, s), 11.93 (1H, brs).

FAB-MAS (mNBA): 560 (M+H)$^+$

Example 25

2'-O,4'-C-Ethylene-2-N-isobutyrylguanosine (Exemplification Compound Number 1-177)

A solution of the compound obtained in Example 24 (10 mg, 0.018 mmol) in methanol (2 ml) was stirred under hydrogen atmosphere at atmospheric pressure in the presence of 20 mg of 20% Pd(OH)$_2$ on carbon as a hydrogenation catalyst for 5 hours. The reaction mixture was filtered in order to remove catalyst and the filtrate was concentrated in vacuo. The residue was purified by chromatography on a silica gel column (using. dichloromethane:methanol=10:2 as the eluant) to afford a colorless oil (5 mg, 0.013 mmol, 72%).

$^1$H-NMR (400 MHz, CD$_3$OD): 1.21 (3H, s), 1.22 (3H, s), 1.41 (1H, dd, 4 and 13 Hz), 2.18 (1H, m), 2.69 (1H, qui, 6.9 Hz), 3.69 (1H, d, 12 Hz), 3.76 (1H, d, 12 Hz), 4.0 (2H, m), 4.26 (1H, d, 3.2 Hz), 4.30 (1H, d, 3.2 Hz), 6.30 (1H, s), 8.40 (1H, s).

FAB-MAS (mNBA): 380 (M+H)$^+$

Example 26

5'-O-Dimethoxytrityl-2'-O,4'-C-ethylene-2-N-isobutyrylguanosine (Exemplification Compound Number 1-35)

A solution of the compound obtained in Example 25 (5 mg, 0.013 mmol) in anhydrous pyridine was azeotropically refluxed in order to remove water. The product was dissolved in anhydrous pyridine (1 ml) under nitrogen atmosphere and to 4,4'-dimethoxytritylchloride (14 mg, 0.04 mmol) was added to the solution and the mixture was stirred at 40° C. for 3 hours. A small amount of methanol was added to the reaction mixture and then the solvent was evaporated in vacuo. The residue was purified by chromatography on a silica gel column (using dichloromethane:methanol=100:6 as the eluant) to afford the title compound (4 mg, 0.0059 mmol, 45%) as colorless solid.

$^1$H-NMR (400 MHz, CDCl$_3$): 1.26 (3H, d, 1.4 Hz), 1.28 (3H, d, 1.4 Hz), 1.66 (1H, m), 2.15 (1H, m), 2.59 (1H, qui, 6.9 Hz), 3.65 (1H, m), 3.78 (1H, m), 4.06 (2H, m), 4.35 (1H, m), 4.38 (1H, d, 3.2 Hz), 6.23 (1H, s), 6.8 (4H, m), 7.2-7.5(9H, m), 8.01 (1H, s), 8.19 (1H, brs).

FAB-MAS (mNBA): 682 (M+H)$^+$

Example 27

5'-O-Dimethoxytrityl-2'-O,4'-C-ethylene-2-N-isobutyrylguanosine-3'-O-(2-cyanoethyl N,N-diisopropyl) phosphoramidite (Exemplification Compound Number 1-185)

A solution of the compound obtained in Example 26 (4 mg, 0.0058 mmol) in anhydrous pyridine was azeotropically refluxed in order to remove water. The product was dissolved under nitrogen atmosphere in anhydrous dichloromethane (0.5 ml). Tetrazole N,N-diisopropylamine salt (5 mg) was added to the solution and then 2-cyanoethyl N,N, N',N'-tetraisopropylphophoramidite (9 µl, 0.03 mmol) was added dropwise in an ice bath. The mixture was stirred at room temperature for 1 hour. The reaction mixture was washed with saturated aqueous sodium hydrogencarbonate solution and saturated aqueous sodium chloride solution and concentrated in vacuo. The residue was purified by chromatography on a silica gel column (using dichloromethane: ethyl acetate=2:1 as the eluant) to afford the title compound (4 mg) as a white solid.

$^1$H-NMR (400 MHz, CDCl$_3$): 1.1-1.4 (19H, m), 2.1 (1H, m), 2.4 (2H, m), 2.6 (1H, m), 3.3-3.6 (6H, m), 3.8 (6H, s), 4.04.6 (4H, m), 6.2 (1H, s), 6.8 (4H, m), 7.2-7.5 (9H, m), 8.1 (1H, s).

Example 28

2'-O,4'-C-Ethyleneguanosine (Exemplification Compound Number 1-5)

A solution of the compound obtained in Example 25 (0.5 mg) in methanol saturated with ammonia (0.5 ml) was allowed to stand at 60° C. for 5 hours. The mixture was concentrated to afford a white powder (0.4 mg).

FAB-MAS (mNBA): 310 (M+H)$^+$ UV (λmax): 255 (pH7), 256 (pH1), 258-266 (pH13)

Example 29

Synthesis of Oligonucleotide Derivative

Synthesis of an oligonucleotide derivative was carried out using a mechanical nucleic acid synthesiser (ABI model392 DNA/RNA synthesiser: a product of Perkin-Elmer Corporation) on a scale of 1.0 µmole. The solvents, reagents and concentrations of phosphoramidite in every synthetic cycle are the same as those in the synthesis of natural oligonucleotides. Solvents, reagents and phosphoramidites of the natural type nucleosides are products of PE Biosystems Corporation. Every modified oligonucleotide derivative sequence was synthesized by repetition of condensation of the compound obtained in Example 9 or amidites containing the 4 species of nucleic acid bases for nucleotide synthesis with the 5'-hydroxy group of thymidine produced by deprotection of the DMTr group of 5'-O-DMTr-thymidine (1.0 µmole) using trichloroacetic acid, wherein the 3'-hydroxy group of the thymidine was attached to a CGP carrier. The synthetic cycle is as follows:

1) detritylation trichloroacetic acid/dichloromethane; 35 sec
2) coupling phosphoramidite (about 20 eq), tetrazole/acetonitrile; 25 sec or 10 min
3) capping 1-methylimidazole/tetrahydrofuran, acetic anhydride/pyridine/tetrahydrofuran; 15 sec
4) oxidation iodine/water/pyridine/tetrahydrofuran; 15 sec In the above cycle 2) when the compound obtained in Example 9 was used the reaction time was 10 minutes and when phosphoramidites were used the reaction time was 25 seconds.

After synthesis of a desired oligonucleotide derivative sequence, the 5'-DMTr group was removed and then the carrier containing the desired product was conventionally treated with concentrated aqueous ammonia solution in order to detach the oligomer from the carrier and to deprotect the cyanoethyl group which is protecting the phosphate group. The amino protecting group in adenine, guanine and cytosine was removed from the oligomer. The oligonucleotide derivative was purified by reverse-phase HPLC (HPLC: LC-VP: a product of Shimazu Corp.; column: Wakopak WS-DNA: a product of Wako Pure Chemical Industry Ltd.) to afford the desired oligonucleotide.

According to this synthetic method the following oligonucleotide sequence (which oligonucleotide is hereinafter referred to as "oligonucleotide 1") was obtained (0.23 μmol, yield 23%).

5'-gcgtttttgct-3' (exemplification of SEQ ID NO: 2 in the SEQUENCE LISTING) wherein the sugar moiety of the thymidines at base numbers 4 to 8 is 2'-O,4'-C ethylene.

Reference Example 1

3,5-Di-O-benzyl-4-trifluoromethanesulfonyloxymethyl-1,2-O-isopropylidene-α-D-erythropentofuranose Anhydrous pyridine (0.60 ml, 7.5 mmol) was added was added to a solution of 3,5-di-O-benzyl-4-hydroxymethyl-1,2-O-isopropylidene-α-D-erythropentofuranose (2000 mg, 5.0 mmol) in anhydrous dichloromethane (50 ml) and trifluoromethanesulfonic anhydride (1010 mg, 6.0 mmol) under nitrogen atmosphere at −78° C. and the mixture was stirred for 40 minutes. The reaction mixture was partitioned between the methylenechloride and saturated aqueous sodium hydrogencarbonate solution (about 100 ml). The organic layer was washed with saturated aqueous sodium hydrogencarbonate solution (about 100 ml) and saturated aqueous sodium chloride solution (about 100 ml), dried over anhydrous magnesium sulfate and then concentrated in vacuo to give a white powder (2520 mg, 4.73 mmol, 95%) which was used in the next reaction without further purification.

$^1$H-NMR (400 MHz, CDCl$_3$): 1.34 (3H, s), 1.63 (3H, s), 3.48 (1H, d, 10 Hz), 3.53 (1H, d, 10 Hz), 4.21 (1H, d, 5.0 Hz), 4.5 (4H, m), 4.74 (1H, d, 12 Hz), 4.80 (1H, d, 1H, d, 12 Hz), 5.01 (1H, d, 12 Hz), 5.73 (1H, d, 4.6 Hz), 7.3 (10H, m).

Reference Example 2

3,5-Di-O-benzyl-4-cyanomethyl-1,2-O-isopropylidene-α-D-erythropentofuranose

The compound obtained in Reference example 1 (2520 mg, 4.73 mmol) was dissolved in dimethylsulfoxide (50 ml) at 90° C. To the solution was added sodium cyanide (463 mg, 9.46 mmol) at room temperature and the mixture was stirred at 50° C. for 3 hours. The reaction mixture was partitioned between water (about 100 ml) and ethyl acetate (about 100 ml). The organic layer was washed with saturated aqueous sodium chloride solution (about 100 ml), dried over anhydrous magnesium sulfate and then concentrated in vacuo. The residue was purified by chromatography on silica gel (using hexane:ethyl acetate=4:1) to give a colorless oil (1590 mg, 3.89 mmol, 82%).

$^1$H-NMR (400 MHz, CDCl$_3$): 1.34 (3H, s), 1.62 (3H, s), 2.88 (1H, d, 17 Hz), 3.15 (1H, d, 17 Hz), 3.50 (1H, d, 10 Hz), 3.58 (1H, d, 10 Hz), 4.08 (1H, d, 5.1 Hz), 4.52 (1H, d, 12 Hz), 4.56 (1H, d, 12 Hz), 4.57 (1H, m), 4.58 (1H, d, 12 Hz), 4.76 (1H, d, 12 Hz), 5.73 (1H, d, 3.7 Hz), 7.3 (10H, m).

Reference Example 3

3,5-Di-O-benzyl-4-formylmethyl-1,2-O-isopropylidene-α-D-erythropentofuranose

A 1.5M toluene solution of isobutylaluminium hydride (2 ml, 3.0 mmol) was slowly added dropwise to a solution of the compound obtained in Reference example 2 (610 mg, 1.49 mmol) in dichloromethane (10 ml) under nitrogen atmosphere at −78° C. and the mixture was stirred for 1 hour at −78° C. and then warmed to room temperature. To the reaction mixture was added methanol (5 ml) and saturated aqueous ammonium chloride solution (about 20 ml) and this mixture was stirred for 30 minutes. The reaction mixture was extracted with ethyl acetate (about 30 ml). The organic layer was washed with saturated aqueous sodium hydrogencarbonate solution (about 30 ml) and saturated aqueous sodium chloride solution (about 30 ml), dried over anhydrous magnesium sulfate and then concentrated in vacuo to give a product which was used in the next reaction without further purification.

Reference Example 4

3,5-Di-O-benzyl-4-hydroxyethyl-1,2-O-isopropylidene-α-D-erythropentofiiranose

NaBH$_4$ (7.6 mg, 0.2 mmol) was added to a solution of the compound obtained in Reference example 3 (154 mg, 0.377 mmol) in ethanol (5 ml) and the mixture was stirred at room temperature for 1 hour. The reaction mixture was partitioned between ethyl acetate (about 10 ml) and water (about 10 ml) and the organic layer was washed with saturated aqueous sodium chloride solution (about 10 ml), dried over anhydrous magnesium sulfate and then concentrated in vacuo. The residue was purified by chromatography on silica gel (using hexane:ethyl acetate=2:1) to give a colorless oil (117 mg, 0.284 mmol, 75%).

$^1$H-NMR (400 MHz, CDCl$_3$): 1.33 (3H, s), 1.66 (3H, s), 1.78 (1H, ddd, 4.0, 8.5, 15 Hz), 2.51 (1H, ddd, 3.4, 6.4, 15 Hz), 3.31 (1H, d, 10 Hz), 3.54 (1H, d, 10 Hz), 3.80 (2H, m), 4.13 (1H, d, 5.3 Hz), 4.43 (1H, d, 12 Hz), 4.52 (1H, d, 12 Hz), 4.55 (1H, d, 12 Hz), 4.65 (1H, dd, 4.0, 5.3 Hz), 4.77 (1H, d, 12 Hz), 5.77 (1H, d, 4.0 Hz), 7.3 (10H, m).

FABMS (mNBA): 415 (M+H)$^+$, [α]$_D$+57.4° (0.91, methanol).

Reference Example 5

3,5-Di-O-benzyl-4-formyl-1,2-O-isopropylidene-α-D-erythropentofuranose

Oxalyl chloride (6.02 ml, 69.0 mmol) was added to methylenechloride (200 ml) cooled at −78° C. A solution of dimethylsulfoxide (7.87 ml, 110 mmol) in anhydrous methylenechloride (100 ml) was added dropwise to this solution. After stirring for 20 minutes a solution of 3,5-di-O-benzyl-1,2-O-isopropylidene-α-D-erythropentofuranose (9210 mg, 23.02 mmol) in anhydrous dichloromethane (100 ml) was added dropwise to this mixture and the mixture was stirred for 30 minutes. Triethylamine (28 ml, 200 mmol) was added to this reaction mixture and the mixture was slowly warmed to room temperature. The reaction mixture was partitioned between the dichloromethane and water (about 300 ml). The organic layer was washed with water (about 300 ml) and saturated aqueous sodium chloride solution (about 300 ml), dried over anhydrous magnesium sulfate and then concentrated in vacuo. The residue was purified by chromatography on silica gel (using hexane:ethyl acetate=5:1) to give a colorless oil (8310 mg, 20.88 mmol, 91%).

$^1$H-NMR (400 MHz, CDCl$_3$): 1.35 (3H, s), 1.60 (3H, s), 3.61 (1H, d, 11 Hz), 3.68 (1H, d, 11 Hz), 4.37 (1H, d, 4.4 Hz), 4.46 (1H, d, 12 Hz), 4.52 (1H, d, 12 Hz), 4.59 (1H, d, 12 Hz), 4.59 (1H, dd, 3.4, 4.4 Hz), 4.71 (1H, d, 12 Hz), 5.84 (1H, d, 3.4 Hz), 7.3 (10H, m), 9.91 (1H, s). FABMS (mNBA): 397 (M–H)$^+$, 421 (M+Na)$^+$, [α]$_D$+27.4° (0.51, methanol).

Reference Example 6

3,5-Di-O-benzyl-4-vinyl-1,2-O-isopropylidene-α-D-erythropentofuranose

A 0.5M toluene solution of Tebbe reagent (44 ml, 22 mmol) was added to a solution of the compound obtained in Reference example 5 (8310 mg, 20.88 mmol) in anhydrous tetrahydrofuran (300 ml) under nitrogen atmosphere at 0° C. and the mixture was stirred at 0° C. for 1 hour. Diethyl ether (300 ml) was added to the reaction mixture and then added 0.1N aqueous sodium hydroxide solution (20 ml) was slowly added. The mixture was filtrated through celite in order to remove precipitates and the precipitates were washed with diethyl ether (about 100 ml). The organic layer was dried over anhydrous magnesium sulfate and then concentrated in vacuo. The residue was purified by chromatography on basic alumina using dichloromethane to afford crude product which was further purified by chromatography on silica gel (using hexane:ethyl acetate=8:1-5:1) to give a colorless oil (5600 mg, 14.14 mmol, 68%).

$^1$H-NMR (400 MHz, CDCl$_3$): 1.28 (3H, s), 1.52 (3H, s), 3.31 (1H, d, 11 Hz), 3.34 (1H, d, 11 Hz), 4.25 (1H, d, 4.9 Hz), 4.40 (1H, d, 12 Hz), 4.52 (1H, d, 12 Hz), 4.57 (1H, dd, 3.9, 4.9 Hz), 4.59 (1H, d, 12 Hz), 4.76 (1H, d, 12 Hz), 5.25 (1H, dd, 1.8, 11 Hz), 5.52 (1H, dd, 1.8, 18 Hz), 5.76 (1H, d, 3.9 Hz), 6.20 (1H, dd, 11, 18 Hz), 7.3 (10H, m).
FABMS (mNBA): 419 (M+Na)$^+$.

Reference Example 7

3,5-Di-O-benzyl-4-hydroxyethyl-1,2-O-isopropylidene-α-D-erythropentofuranose

A 0.5M tetrahydrofuran solution of 9-BBN (9-borabicyclo[3.3.1]nonane) (80 ml, 40 mmol) was added dropwise to a solution of the compound obtained in Reference example 6 (5500 mg, 13.89 mmol) in anhydrous tetrahydrofuran (200 ml) under nitrogen atmosphere and the mixture was stirred at room temperature overnight. Water was added to the reaction mixture until evolution of gas ceased, 3N aqueous sodium hydroxide solution (30 ml) was added and then slowly 30% aqueous hydrogen peroxide solution was added keeping between 30 and 50° C. This mixture was stirred for 30 minutes and partitioned between saturated aqueous sodium chloride solution (about 200 ml) and ethyl acetate (200 ml). The organic layer was washed with neutral phosphoric acid buffer solution (about 200 ml) and saturated aqueous sodium chloride solution (about 200 ml) and dried over anhydrous magnesium sulfate and then concentrated in vacuo. The residue was purified by chromatography on silica gel (using hexane:ethyl acetate=2:1-1:1) to give a colorless oil (5370 mg, 12.97 mmol, 93%).

$^1$H-NMR (400 MHz, CDCl$_3$): 1.33 (3H, s), 1.66 (3H, s), 1.78 (1H, ddd, 4.0, 8.5, 15 Hz), 2.51 (1H, ddd, 3.4, 6.4, 15 Hz), 3.31 (1H, d, 10 Hz), 3.54 (1H, d, 10 Hz), 3.80 (2H, m), 4.13 (1H, d, 5.3 Hz), 4.43 (1H, d, 12 Hz), 4.52 (1H, d, 12 Hz), 4.55 (1H, d, 12 Hz), 4.65 (1H, dd, 4.0, 5.3 Hz), 4.77 (1H, d, 12 Hz), 5.77 (1H, d, 4.0 Hz), 7.3 (10H, m).
FABMS (mNBA): 415 (M+H)$^+$, [α]$_D$+57.4° (0.91, methanol).

Reference Example 8

3,5-Di-O-benzyl-4-(p-toluenesulfonyloxyethyl)-1,2-O-isopropylidene-α-D-erythropen tofuranose Triethylamine (1.8 ml, 13 mmol), dimethylaminopyridine (30 mg, 0.25 mmol), and p-toluenesulfonyl chloride (858 mg, 4.5 mmol) were added to a solution of the compound obtained in Reference example 4 which was azeotropically refluxed with toluene (1035 mg, 2.5 mmol) in anhydrous dichloromethane (35 ml) under nitrogen atmosphere at 0° C. and the mixture was stirred at room temperature overnight. The reaction mixture was partitioned between the dichloromethane and saturated aqueous sodium hydrogencarbonate solution (about 100 ml). The organic layer was washed with saturated aqueous sodium hydrogencarbonate solution (about 100 ml) and saturated aqueous sodium chloride solution (about 100 ml) and dried over anhydrous magnesium sulfate and then concentrated in vacuo. The residue was purified by chromatography on silica gel (using hexane:ethyl acetate=3:1) to give a colorless oil (1340 mg, 2.6 mmol, 94%).

$^1$H-NMR (400 MHz, CDCl$_3$): 1.33 (3H, s), 1.49 (3H, s), 1.99 (1H, dt, 7.6 and 15 Hz), 2.47 (3H, s), 2.60 (1H, ddd, 5.7, 7.6, 15 Hz), 3.28 (1H, d, 10 Hz), 3.45 (1H, d, 10 Hz), 4.11 (1H, d, 5.3 Hz), 4.32 (2H, m), 4.42 (1H, d, 12 Hz), 4.50 (1H, d, 12 Hz), 4.54 (1H, d, 12 Hz), 4.62 (1H, dd, 4.0, 5.2 Hz), 4.76 (1H, d, 12 Hz), 5.74 (1H, d, 4.0 Hz), 7.3 (12H, m), 7.78 (2H, d, 8.3 Hz).
FAB-MAS (mNBA): 569 (M+H)$^+$ Reference Example 9

1,2-Di-O-acetyl-3,5-di-O-benzyl-4-(p-toluenesulfonyloxyethyl)-α-D-erythropentofura nose Acetic anhydride (1.88 ml, 20 mmol) and concentrated sulfuric acid (0.01 ml) were added to a solution of the compound obtained in Reference example 8 (1340 mg, 2.36 mmol) in acetic acid (15 ml) and the mixture was stirred at room temperature for 1 hour. The reaction mixture was poured into water (60 ml) in an ice-bath and stirred for 30 minutes and then partitioned between saturated aqueous sodium chloride solution (about 100 ml) and ethyl acetate (about 100 ml). The organic layer was washed with neutral phosphoric acid buffer solution, saturated aqueous sodium hydrogencarbonate solution and saturated aqueous sodium chloride solution and dried over anhydrous magnesium sulfate and then concentrated. The residue was purified by chromatography on silica gel (using hexane:ethyl acetate=2:1) to give a colorless oil (1290 mg, 2.11 mmol, 89%, α:β=1:5).

$^1$H-NMR (400 MHz, CDCl$_3$): (β derivative) 1.86 (3H, s), 2.05 (3H, s), 2.08 (1H, m), 2.18 (1H, m), 2.42 (3H, s), 3.30 (1H, d, 10 Hz), 3.33 (1H, d, 10 Hz), 4.23 (1H, d, 5.1 Hz), 4.24 (2H, m), 4.42 (2H, s), 4.45 (1H, d, 12 Hz), 4.55 (1H, d, 12 Hz), 5.28 (1H, d, 5.1 Hz), 6.01 (1H, s), 7.3 (12H, m), 7.73 (2H, d, 8.3 Hz).

FAB-MAS (mNBA): 613 (M+H)$^+$

Reference Example 10

2'-O-Acetyl-3',5'-di-O-benzyl-4'-p-toluenesulfonyloxyethyl-5-methyluridine

Trimethylsilylated thymine (500 mg, about 2 mmol), which was prepared according to a method of H. Vorbrggen, K. Krolikiewicz and B. Bennua (Chem. Ber., 114, 1234-1255 (1981)), was added to a solution of the compound obtained in Reference example 9 (650 mg, 1.06 mmol) in anhydrous 1,2-dichloroethane (15 ml) at room temperature under nitrogen atmosphere. Trimethylsilyl trifluoromethanesulfonate (0.36 ml, 2 mmol) was added dropwise to the mixture and the mixture was stirred at 50° C. for 1 hour. Saturated aqueous sodium hydrogencarbonate solution (about 50 ml) was added to the reaction mixture and the mixture was filtered through celite. Dichloromethane (about 50 ml) was added to the filtrate. The organic layer was washed with saturated aqueous sodium hydrogencarbonate solution (about 50 ml) and saturated aqueous sodium chloride solution (about 50 ml) and dried over anhydrous magnesium sulfate and then concentrated in vacuo. The residue was purified by chromatography on silica gel (using hexane:ethyl acetate=1.2:1) to give a colorless amorphous solid (432 mg, 0.64 mmol, 60%).

hu 1H-NMR (400 MHz, CDCl$_3$): 1.52 (3H, d, 0.9 Hz), 1.94 (1H, dt, 7.5 and 15 Hz), 2.06 (3H, s), 2.23 (1H, dt, 6.0 and 15 Hz), 2.42 (3H, s), 3.38 (1H, d, 10 Hz), 3.67 (1H, d, 10 Hz), 4.17 (2H, m), 4.36 (1H, d, 6.0 Hz), 4.41 (1H, d, 12 Hz), 4.44 (1H, d, 12 Hz), 4.48 (1H, d, 12 Hz), 4.58 (1H, d, 12 Hz), 5.39 (1H, dd, 5.1 and 6.0 Hz), 6.04 (1H, d, 5.1 Hz), 7.3 (12H, m), 7.73 (2H, dt, 1.8 and 8.3 Hz), 8.18 (1H, s).

FAB-MAS (mNBA): 679 (M+H)$^+$

Reference Example 11

2'-O-Acetyl-3',5'-di-O-benzyl-4'-p-toluenesulfonyloxyethyl-4-N-benzoylcytidine

Trimethylsilylated benzoylcytosine (300 mg, about 1.0 mmol), which was prepared according to a method of H. Vorbrggen, K. Krolikiewicz and B. Bennua (Chem. Ber., 114, 1234-1255 (1981)), was added to a solution of the compound obtained in Reference example 9 (383 mg, 0.626 mmol) in anhydrous 1,2-dichloroethane (4 ml). Trimethylsilyl trifluoromethanesulfonate (0.18 ml, 0.995 mmol) at 0° C. was added to the mixture and the mixture was stirred at 50° C. for 1 hour. Saturated aqueous sodium hydrogencarbonate solution (about 10 ml) and methylenechloride (about 20 ml) was added to the mixture and then the mixture was stirred. The resulting white precipitates were filtered off through celite. The organic layer of the filtrate was washed with saturated aqueous sodium chloride solution (about 20 ml) and dried over anhydrous magnesium sulfate and then concentrated in vacuo to give a colorless amorphous solid (397 mg, 83%).

$^1$H-NMR (400 MHz, CDCl$_3$): 8.70 (1H, br), 8.18 (1H, d, 7.4 Hz), 7.87 (2H, d, 7.5 Hz), 7.72 (2H, d, 8.3 Hz), 7.61-7.57 (1H, m), 7.51-7.48 (2H, m), 7.43-7.21 (13H, m), 6.02 (1H, d, 2.9 Hz), 5.40 (1H, dd, 5.8, 2.9 Hz), 4.57 (1H, d, 11 Hz), 4.39 (1H, d, 11 Hz), 4.32-4.28 (3H, m), 4.19-4.16 (2H, m), 3.69 (1H, d, 11 Hz), 3.31 (1H, d, 11 Hz), 2.40 (3H, s), 2.30-2.23 (1H, m), 2.06 (3H, m), 1.95-1.89 (1H, m).

FAB-MAS (mNBA): 768 (M+H)$^+$

Reference Example 12

2'-O-Acetyl-3',5'-di-O-benzyl-4'-p-toluenesulfonyloxyethyl-6-N-benzoyladenosine

Trimethylsilylated benzoyladenosine (500 mg, about 2.0 mmol), which was prepared according to a method of H. Vorbrggen, K. Krolikiewicz and B. Bennua (Chem. Ber., 114, 1234-1255 (1981)), was added to a solution of the compound obtained in Reference example 9 (600 mg, 0.98 mmol) in anhydrous 1,2-dichloroethane (15 ml) at room temperature under nitrogen atmosphere. After dropwise addition of trimethylsilyl trifluoromethanesulfonate (0.36 ml, 2 mmol) to the mixture, the mixture was stirred at 50° C. for 4 hour. Saturated aqueous sodium hydrogencarbonate solution (about 50 ml) and dichloromethane (50 ml) were added to the reaction mixture and the mixture was partitioned between these two layers. The organic layer was washed with saturated aqueous sodium hydrogencarbonate solution (about 50 ml) and saturated aqueous sodium chloride solution (about 50 ml) and dried over anhydrous magnesium sulfate and then concentrated in vacuo. The residue was purified by chromatography on silica gel (using dichloromethane:methanol=50:1) to give a colorless amorphous solid (405 mg, 0.51 mmol, 52%).

$^1$H-NMR (400 MHz, CDCl$_3$): 2.0 (1H, m), 2.06 (3H, s), 2.32 (1H, dt, 6.0 and 15 Hz), 2.40 (3H, s), 3.36 (1H, d, 10 Hz), 3.58 (1H, d, 10 Hz), 4.22 (2H, m), 4.39 (1H, d, 12 Hz), 4.45 (1H, d, 12 Hz), 4.47 (1H, d, 12 Hz), 4.59 (1H, d, 12 Hz), 4.62 (1H, d, 5.6 Hz), 5.94 (1H, dd, 4.5 and 5.6 Hz), 6.21 (1H, d, 4.5 Hz), 7.2-7.3 (12H, m), 7.54 (2H, m), 7.62 (1H, dt, 1.2 and 6.2 Hz), 7.72 (2H, d, 8.3 Hz), 8.02 (2H, m), 8.21 (1H, s), 8.75 (1H, s), 8.97 (1H, brs).

FAB-MAS (mNBA): 792 (M+H)$^+$

Reference Example 13

2'-O-Acetyl-3',5'-di-O-benzyl-4'-p-toluenesulfonyloxyethyl-uridine

Trimethylsilylated uracil (200 mg, about 0.8 mmol), which was prepared according to a method of H. Vorbrggen, K. Krolikiewicz and B. Bennua (Chem. Ber., 114, 1234-1255 (1981)), was added to a solution of the compound obtained in Reference example 9 (200 mg, 0.327 mmol) in anhydrous 1,2-dichloroethane (8 ml) at room temperature under nitrogen atmosphere. After dropwise addition of trimethylsilyl trifluoromethanesulfonate (0.145 ml, 0.8 mmol) to the mixture, the mixture was stirred at 70° C. for 1 l hour. Saturated aqueous sodium hydrogencarbonate solution (about 10 ml) was added to the reaction mixture, the mixture was filtered through celite and dichloromethane (about 10 ml) was added to the filtrate. The organic layer was washed with saturated aqueous sodium hydrogencarbonate solution and saturated aqueous sodium chloride solution and dried over anhydrous magnesium sulfate and then concentrated in vacuo. The residue was purified by chromatography on silica gel (using dichloromethane:methanol=100:2) to give a colorless oil (199 mg, 0.299 mmol, 92%).

$^1$H-NMR (400 MHz, CDCl$_3$): 1.94 (1H, dt, 7.4 and 15 Hz), 2.07 (3H, s), 2.23 (1H, dt, 5.9 and 15 Hz), 2.43 (3H, s), 3.36 (1H, d, 10 Hz), 3.65 (1H, d, 10 Hz), 4.17 (2H, dd, 6 and 7 Hz), 4.31 (1H, d, 5.9 Hz), 4.38 (1H, d, 11 Hz), 4.39 (1H, d, 11 Hz), 4.40 (1H, d, 1H, d, 11 Hz), 4.58 (1H, d, 11 Hz), 5.29 (1H, dd, 2.4 and 8.2 Hz), 5.33 (1H, dd, 4.5 and 6 Hz), 6.00 (1H, d, 4.5 Hz), 7.2-7.4 (12H, m), 7.61 (1H, d, 8.2 Hz), 7.74 (1H, d, 8.3 Hz), 8.14 (1H, brs).

FAB-MAS (mNBA): 665 (M+H)$^+$

Reference Example 14

2'-O-Acetyl-3',5'-di-O-benzyl-4'-p-toluenesulfonyloxyethyl-4-N-benzoyl-5-methyloctyl dine Trimethylsilylated benzoyl 5-methylcytosine (400 mg, about 1.2 mmol), which was prepared according to a method of H. Vorbrggen, K. Krolikiewicz and B. Bennua (Chem. Ber., 114, 1234-1255 (1981)) was added to a solution of the compound obtained in Reference example 9 (400 mg, 0.653 mmol) in anhydrous 1,2-dichloroethane (6 ml). After addition of trimethylsilyl trifluoromethanesulfonate (0.180 μl, 1.0 mmol) to the mixture at 0° C., the mixture was stirred at 50° C. for 1 hour. The reaction mixture was warmed to room temperature. Saturated aqueous sodium hydrogencarbonate solution (about 5 ml) and methylenechloride (about 10 ml) were added to the reaction mixture and the mixture was stirred. The mixture was filtered through celite in order to remove white precipitates. The organic layer of the filtrate was washed with saturated aqueous sodium chloride solution and dried over anhydrous magnesium sulfate and then concentrated in vacuo to give a colorless amorphous solid (320 mg, 0.409 mmol, 63%).

$^1$H-NMR (400 MHz, CDCl$_3$): 1.68 (3H, s), 1.95 (1H, dt, 7.3 and 15 Hz), 2.07 (3H, s), 2.25 (1H, dt, 6 and 15 Hz), 2.43 (3H, s), 3.40 (1H, d, 10 Hz), 3.71 (1H, d, 10 Hz), 4.18 (2H, m), 4.37 (1H, d, 5.8 Hz), 4.42 (1H, d, 12 Hz), 4.46 (1H, d, 12 Hz), 4.51 (1H, d, 12 Hz), 4.61 (1H, d, 12 Hz), 5.42 (1H, dd, 4.9 and 5.8 Hz), 6.07 (1H, d, 4.9 Hz), 7.2-7.6 (17H, m), 7.74 (2H, d, 8.3 Hz), 8.28 (2H, d, 7.0 Hz).

FAB-MAS (mNBA): 782 (M+H)$^+$

Reference Example 15

2'-O-Acetyl-3',5'-di-O-benzyl-4'-p-toluenesulfonyloxyethyl-2-N-isobutyrylguanosine Trimethylsilylated isobutyrylguanosine (650 mg, about 1.5 mmol), which was prepared according to a method of H. Vorbrggen, K. Krolikiewicz and B. Bennua (Chem. Ber., 114, 1234-1255 (1981)), was added to a solution of the compound obtained in Reference example 9 (400 mg, 0.65 mmol) in anhydrous 1,2-dichloroethane (10 ml) at room temperature under nitrogen atmosphere. After addition of trimethylsilyl trifluoromethanesulfonate (0.2 ml, 1.2 mmol) to the mixture and the mixture was stirred at 50° C. for 4 hour. Saturated aqueous sodium hydrogencarbonate solution (about 5 ml) was added to the reaction mixture and the organic layer was washed with saturated aqueous sodium hydrogencarbonate solution and saturated aqueous sodium chloride solution and dried over anhydrous magnesium sulfate and then concentrated in vacuo to give a product which was used in the next reaction without further purification.

Test Example 1

Tm Measurement Test

A sample solution (1000 μL) having a final concentration of NaCl of 100 mM, sodium phosphate buffer solution (pH 7.2) of 10 mM, oligonucleotide (1) of 4 μM, and complementary DNA (hereinafter referred to as oligonucleotide (2)), having a sequence indicated by its complementary chain (sequence: 5'-agcaaaaaacgc-3' (SEQ ID NO: 1 of the SEQUENCE LISTING) or complementary RNA (hereinafter referred to as oligonucleotide (3)) having a sequence indicated by the sequence 5'-agaaaaaacgc-3' (SEQ ID NO: 1 of the SEQUENCE LISTING), of 4 μM was warmed in a boiling water bath and slowly cooled to room temperature over the course of about two hours. The sample solution was then heated and measured using a spectrophotometer (UV-3100PC: a product of Shimadzu Corp.). The sample was heated in a cell (cell thickness: 1.0 cm, cylindrical jacket type) by circulating water heated with an incubator (Haake FE2: a product of EKO Corp.), and the temperature was monitored using a digital thermometer (SATO SK1250MC). The temperature was raised from 20° C. to 95° C. and the intensity of ultraviolet absorbance at the maximum absorption wavelength in the vicinity of 260 nm was measured for each 1° C. increase in temperature. Naturally-occurring DNA (hereinafter referred to as oligonucleotide (4)) having the sequence indicated by the sequence 5'-gcgttttttgct-3' (Sequence No. 2 of the Sequence Listing), which is the same sequence as oligonucleotide (1) (compound of Example 29), was used as the control, and the same procedure was performed.

The temperature at which the amount of change per 1° C. reached a maximum was taken to be Tm (melting temperature), and the complementary chain formation ability of the oligonucleotide analogue was evaluated at this temperature.

The following shows the results of measuring the Tm values of oligonucleotide (4) (naturally-occurring DNA) and oligonucleotide (1) (Compound of Example 29) relative to oligonucleotide (2) (complementary DNA) and oligonucleotide (3) (complementary RNA).

TABLE 3

| | Tm (° C.) | |
|---|---|---|
| Compound | Oligonucleotide (2) | Oligonucleotide (3) |
| Oligonucleotide (4) | 48 | 44 |
| Oligonucleotide (1) | 61 | 75 |

As is clear from the above table, the oligonucleotide analogue of the present invention exhibited a remarkably higher Tm as well as remarkably higher complementary chain formation ability as compared with naturally-occurring DNA.

Test Example 2

Measurement of Nuclease Enzyme Resistance

Exonuclease or endonuclease was mixed into a buffer solution of oligonucleotide held at 37° C. for 15 minutes. The mixed solution was then held at 37° C. for a predetermined amount of time. Ethylenediamine tetraacetic acid (EDTA) was added to a portion of the mixed solution and the mixture was heated at 100° C. for 2 minutes in order to stop the reaction. The amount of oligonucleotide remaining in the mixture was determined by reverse phase high-performance liquid column chromatography, and the time-based changes in the amount of oligonucleotide in the presence of nuclease were measured.

The oligonucleotide analogues of the present invention demonstrate remarkable nuclease resistance.

Example 30

Synthesis of Oligonucleotide Derivative

According to the procedure of Example 29 the following oligonucleotide sequence (which oligonucleotide is hereinafter referred to as "oligonucleotide (5)") was obtained.

5'-tcctctgtgcttggttctggcct-3' (exemplification of SEQ ID NO: 3 in the SEQUENCE LISTING), wherein the sugar moiety of the thymidines and cytidines at base numbers 1 to 3 and 21 to 23 is 2'-O,4'-C ethylene.

Test Example 3

Inhibition of SNS/PN3 Gene Expression

Dorsal root ganglion (hereinafter "DRG") was delivered from SD (Sprague Dawley) rat of 16 fetal day age. DRG was incubated with PBS (sodium phosphate buffer; 12 ml) containing 1mg/ml collagenase for 30 min at 37° C. After incubation, the supernatant of DRG was removed by centrifugation. DRG was incubated with PBS (12 ml) containing 0.1% trypsin for 30 min at 37° C. After incubation DRG was dispersed by adding Dnase I solution (2 mg/ml in PBS, 60 µl) and pipetting in MEM (Minimum essential medium) containing 10% FCS (fetal calf serum), 28 mM glucose and 100 ng/ml NGF (resulting medium is hereinafter "FCS-MEM"). The resulting cell suspension (hereinafter "DRG cell") was plated to each well of 12 well plate in a ratio of 0.5 ml/well those well had been coated with Poly-D-Lysin and filled with FCS-MEM (0.5ml/well) containing 16 ng/ml laminin.

DRG cell was cultured in 5% $CO_2$ atmosphere at 37° C. On the day following the plating, half of medium (0.5 ml) was replaced with FCS-MEM containing 20 µM Ara-C.

On the 4th day following the plating, half of medium was replaced with FCS-MEM containing 40 µM oligonucleotide (5) (compound of Example 30).

After incubating 48 hours, RNA of the DRG cell was extracted. Using the RT-PCR (reverse transcript PCR) method, the quantity of the mRNA of the SNS/PN3 was measured (internal standard: TrkA (NGF receptor)). The inhibition ability was evaluated by the following formula.

A=mRNA quantity of the compound treated well
B=mRNA quantity of non treated well (control)
Inhibition rate (%)=(1−A/B)×100

TABLE 4

| Compound | inhibition rate (%) |
|---|---|
| Oligonucleotide (5) | 28 |

As is clear from the above table, the oligonucleotide analogue of the present invention exhibited a remarkably high inhibition ability of SNS/PN3 gene expression. The oligonucleotide analogue of the present invention is thus useful as a pain treatment drug.

INDUSTRIAL APPLICABILITY

The novel oligonucleotide analogue and nucleoside analogue of the present invention are useful as antisense or antigene pharmaceuticals having excellent stability, as detection agents (probes) of a specific gene, as primers for starting amplification or as intermediates for their production.

What is claimed is:

1. A compound of formula (1):

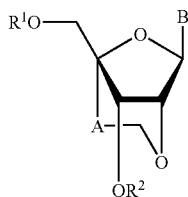

wherein:
- $R^1$ and $R^2$ are the same or different and are selected from the group consisting of hydrogen atoms, hydroxyl protecting groups, phosphate groups, protected phosphate groups and a group of formula —P($R^3$)$R^4$, wherein $R^3$ and $R^4$ are the same or different and are selected from the group consisting of hydroxyl groups, protected hydroxyl groups, mercapto groups, protected mercapto groups, amino groups, alkoxy groups having from 1 to 4 carbon atoms, alkylthio groups having from 1 to 4 carbon atoms, cyanoalkoxy groups having from 1 to 5 carbon atoms and amino groups substituted by an alkyl group having from 1 to 4 carbon atoms;
- A represents a methylene group; and
- B is selected from the group consisting of unsubstituted purin-9-yl groups, unsubstituted 2-oxo-pyrimidin-1-yl groups, and substituted purin-9-yl groups and substituted 2-oxo-pyrimidin-1-yl groups having at least one substituent α selected from the group consisting of hydroxyl groups, protected hydroxyl groups, alkoxy groups having from 1 to 4 carbon atoms, mercapto groups, protected mercapto groups, alkylthio groups having from 1 to 4 carbon atoms, amino groups, protected amino groups, amino groups substituted by an alkyl group having from 1 to 4 carbon atoms, alkyl groups having from 1 to 4 carbon atoms and halogen atoms;

or a salt thereof.

2. The compound according to claim 1 or a salt thereof, wherein $R^1$ is selected from the group consisting of hydrogen atoms, aliphatic acyl groups, aromatic acyl groups, methyl groups substituted by from 1 to 3 aryl groups, methyl groups substituted by from 1 to 3 aryl groups the aryl ring of which is substituted by a substituent selected from the group consisting of lower alkyl, lower alkoxy, halogen and cyano groups, and silyl groups.

3. The compound according to claim 1 or a salt thereof, wherein $R^1$ is selected from the group consisting of hydrogen atoms, acetyl groups, benzoyl groups, benzyl groups, p-methoxybenzyl, dimethoxytrityl, mono-methoxytrityl groups and tert-butyldiphenylsilyl groups.

4. The compound according to claim 1 or a salt thereof, wherein $R^2$ is selected from the group consisting of hydrogen atoms, aliphatic acyl groups, aromatic acyl groups, methyl groups substituted by from 1 to 3 aryl groups, methyl groups substituted by from 1 to 3 aryl groups the aryl ring of which is substituted by a substituent selected from the group consisting of lower alkyl, lower alkoxy, halogen and cyano groups, silyl groups, phosphoramidite groups, phosphonyl groups, phosphate groups and protected phosphate groups.

5. The compound according to claim 2 or a salt thereof, wherein $R^2$ is selected from the group consisting of hydrogen atoms, aliphatic acyl groups, aromatic acyl groups, methyl groups substituted by from 1 to 3 aryl groups, methyl groups substituted by from 1 to 3 aryl groups the aryl ring of which is substituted by a substituent selected from the group consisting of lower alkyl, lower alkoxy, halogen and cyano groups, silyl groups, phosphoramidite groups, phosphonyl groups, phosphate groups and protected phosphate groups.

6. The compound according to claim 3 or a salt thereof, wherein $R^2$ is selected from the group consisting of hydrogen atoms, aliphatic acyl groups, aromatic acyl groups, methyl groups substituted by from 1 to 3 aryl groups, methyl groups substituted by from 1 to 3 aryl groups the aryl ring of which is substituted by a substituent selected from the group consisting of lower alkyl, lower alkoxy, halogen and cyano groups, silyl groups, phosphoramidite groups, phosphonyl groups, phosphate groups and protected phosphate groups.

7. The compound according to claim 1 or a salt thereof, wherein $R^2$ is selected from the group consisting of hydrogen atoms, acetyl groups, benzoyl groups, benzyl groups, p-methoxybenzyl groups, tert-butyldiphenylsilyl groups, —P(OC$_2$H$_4$CN) (N(CH(CH$_3$)$_2$)$_2$), —P(OCH$_3$) (N(CH(CH$_3$)$_2$)$_2$), phosphonyl groups, 2-chlorophenyl phosphate groups and 4-chlorophenyl phosphate groups.

8. The compound according to claim 1 or a salt thereof, wherein $R^2$ is selected from the group consisting of hydrogen atoms, acetyl groups, benzoyl groups, benzyl groups, p-methoxybenzyl groups, tert-butyldiphenylsilyl groups, —P(OC$_2$H$_4$CN) (N(CH(CH$_3$)$_2$)$_2$), —P(OCH$_3$) (N(CH(CH$_3$)$_2$)$_2$), phosphonyl groups, 2-chlorophenyl phosphate groups and 4-chlorophenyl phosphate groups.

9. The compound according to claim 3 or a salt thereof, wherein $R^2$ is selected from the group consisting of hydrogen atoms, acetyl groups, benzoyl groups, benzyl groups, p-methoxybenzyl groups, tert-butyldiphenylsilyl groups, —P(OC$_2$H$_4$CN) (N(CH(CH$_3$)$_2$)$_2$), —P(OCH$_3$) (N(CH(CH$_3$)$_2$)$_2$), phosphonyl groups, 2-chlorophenyl phosphate groups and 4-chlorophenyl phosphate groups.

10. The compound according to claim 1 or a salt thereof, wherein B is selected from the group consisting of 6-aminopurin-9-yl; 6-aminopurin-9-yl, the amino group of which is protected; 2,6-diaminopurin-9-yl; 2-amino-6-chloropurin-9-yl; 2-amino-6-chloropurin-9-yl, the amino group of which is protected; 2-amino-6-fluoropurin-9-yl, 2-amino-6-fluoropurin-9-yl, the amino group of which is protected; 2-amino-6-bromopurin-9-yl; 2-amino-6-bromopurin-9-yl, the amino group of which is protected; 2-amino-6-hydroxypurin-9-yl; 2-amino-6-hydroxypurin-9-yl, the amino group of which is protected; 2-amino-6-hydroxypurin-9-yl, the amino group and hydroxyl group of which are protected; 6-amino-2-methoxypurin-9-yl; 6-amino-2-chloropurin-9-yl; 6-amino-2-fluoropurin-9-yl; 2,6-dimethoxypurin-9-yl; 2,6-dichloropurin-9-yl; 6-mercaptopurin-9-yl; 2-oxo-4-amino-pyrimidin-1-yl; 2-oxo-4-amino-pyrimidin-1-yl, the amino group of which is protected; 2-oxo-4-amino-5-fluoro-pyrimidin-1-yl; 2-oxo-4-amino-5-fluoro-pyrimidin-1-yl, the amino group of which is protected; 4-amino-2-oxo-5-chloro-pyrimidin-1-yl; 2-oxo-4-methoxy-pyrimidin-1-yl; 2-oxo-4-mercapto-pyrimidin-1-yl; 2-oxo-4-hydroxy-pyrimidin-1-yl, 2-oxo-4-hydroxy-5-methylpyrimidin-1-yl; 4amino-5-methyl-2-oxo-pyrimidin-1-yl group and 4-amino-5-methyl-2-oxo-pyrimidin-1-yl group, the amino group of which is protected.

11. The compound according to claim 2 or a salt thereof, wherein B is selected from the group consisting of 6-aminopurin-9-yl; 6-aminopurin-9-yl, the amino group of which is protected; 2,6-diaminopurin-9-yl; 2-amino-6-chloropurin-9-yl; 2-amino-6-chloropurin-9-yl, the amino group of which is protected; 2-amino-6-fluoropurin-9-yl; 2-amino-6-fluoropurin-9-yl, the amino group of which is protected; 2-amino-6-bromopurin-9-yl; 2-amino-6-bromopurin-9-yl, the amino group of which is protected; 2-amino-6-hydroxypurin-9-yl; 2-amino-6-hydroxypurin-9-yl, the amino group of which is protected; 2-amino-6-hydroxypurin-9-yl, the amino group and hydroxyl group of which are protected; 6-amino-2-methoxypurin-9-yl; 6-amino-2-chloropurin-9-yl; 6-amino-2-fluoropurin-9-yl; 2,6-dimethoxypurin-9-yl; 2,6-dichloropurin-9-yl; 6-mercaptopurin-9-yl; 2-oxo-4-amino-pyrimidin-1-yl; 2-oxo-4-amino-pyrimidin-1-yl, the amino group of which is protected; 2-oxo-4-amino-5-fluoro-pyrimidin-1-yl; 2-oxo-4-amino-5-fluoro-pyrimidin-1-yl, the amino group of which is protected; 4-amino-2-oxo-5-chloro-pyrimidin-1-yl; 2-oxo-4-methoxy-pyrimidin-1-yl; 2-oxo-4-mercapto-pyrimidin-1-yl; 2-oxo-4-hydroxy-pyrimidin-1-yl; 2-oxo-4-hydroxy-5-methylpyrimidin-1-yl; 4-amino-5-methyl-2-oxo-pyrimidin-1-yl group and 4-amino-5-methyl-2-oxo-pyrimidin-1-yl group, the amino group of which is protected.

12. The compound according to claim 3 or a salt thereof, wherein B is selected from the group consisting of 6-aminopurin-9-yl; 6-aminopurin-9-yl, the amino group of which is protected; 2,6-diaminopurin-9-yl; 2-amino-6-chloropurin-9-yl; 2-amino-6-chloropurin-9-yl, the amino group of which is protected; 2-amino-6-fluoropurin-9-yl; 2-amino-6-fluoropurin-9-yl, the amino group of which is protected; 2-amino-6-bromopurin-9-yl; 2-amino-6-bromopurin-9-yl, the amino group of which is protected; 2-amino-6-hydroxypurin-9-yl; 2-amino-6-hydroxypurin-9-yl, the amino group of which is protected; 2-amino-6-hydroxypurin-9-yl, the amino group and hydroxyl group of which are protected; 6-amino-2-methoxypurin-9-yl; 6-amino-2-chloropurin-9-yl; 6-amino-2-fluoropurin-9-yl; 2,6-dimethoxypurin-9-yl; 2,6-dichloropurin-9-yl; 6-mercaptopurin-9-yl; 2-oxo-4-amino-pyrimidin-1-yl; 2-oxo-4-amino-pyrimidin-1-yl, the amino group of which is protected; 2-oxo-4-amino-5-fluoro-pyrimidin-1-yl; 2-oxo-4-amino-5-fluoro-pyrimidin-1-yl, the amino group of which is protected; 4-amino-2-oxo-5-chloro-pyrimidin-1-yl; 2-oxo-4-methoxy-pyrimidin-1-yl; 2-oxo-4-mercapto-pyrimidin-1-yl; 2-oxo-4-hydroxy-pyrimidin-1-yl; 2-oxo-4-hydroxy-5-methylpyrimidin-1-yl; 4-amino-5-methyl-2-oxo-pyrimidin-1-yl group and 4-amino-5-methyl-2-oxo-pyrimidin-1-yl groups, the amino group of which is protected.

13. The compound according to claim 4 or a salt thereof, wherein B is selected from the group consisting of 6-aminopurin-9-yl; 6-aminopurin-9-yl, the amino group of which is protected; 2,6-diaminopurin-9-yl; 2-amino-6-chloropurin-9-yl; 2-amino-6-chloropurin-9-yl, the amino group of which is protected; 2-amino-6-fluoropurin-9-yl; 2-amino-6-fluoropurin-9-yl, the amino group of which is protected; 2-amino-6-bromopurin-9-yl; 2-amino-6-bromopurin-9-yl, the amino group of which is protected; 2-amino-6-hydroxypurin-9-yl; 2-amino-6-hydroxypurin-9-yl, the amino group of which is protected; 2-amino-6-hydroxypurin-9-yl, the amino group and hydroxyl group of which are protected; 6-amino-2-methoxypurin-9-yl; 6-amino-2-chloropurin-9-yl; 6-amino-2-fluoropurin-9-yl; 2,6-dimethoxypurin-9-yl; 2,6-dichloropurin-9-yl; 6-mercaptopurin-9-yl; 2-oxo-4-amino-pyrimidin-1-yl; 2-oxo-4-amino-pyrimidin-1-yl, the amino group of which is protected; 2-oxo-4-amino-5-fluoro-pyrimidin-1-yl; 2-oxo-4-amino-5-fluoro-pyrimidin-1-yl, the amino group of which is protected; 4-amino-2-oxo-5-chloro-pyrimidin-1-yl; 2-oxo-4-methoxy-pyrimidin-1-yl; 2-oxo-4-mercapto-pyrimidin-1-yl; 2-oxo-4-hydroxy-pyrimidin-1-yl; 2-oxo-4-hydroxy-5-methylpyrimidin-1-yl; 4-amino-5-methyl-2-oxo-pyrimidin-1-yl group and 4-amino-5-methyl-2-oxo-pyrimidin-1-yl group, the amino group of which is protected.

14. The compound according to claim 5 or a salt thereof, wherein B is selected from the group consisting of 6-aminopurin-9-yl; 6-aminopurin-9-yl, the amino group of which is protected; 2,6-diaminopurin-9-yl; 2-amino-6-chloropurin-9-yl; 2-amino-6-chloropurin-9-yl, the amino group of which is protected; 2-amino-6-fluoropurin-9-yl; 2-amino-6-fluoropurin-9-yl, the amino group of which is protected; 2-amino-6-bromopurin-9-yl; 2-amino-6-bromopurin-9-yl, the amino group of which is protected; 2-amino-6-hydroxypurin-9-yl; 2-amino-6-hydroxypurin9-yl, the amino group of which is protected; 2-amino-6-hydroxypurin-9-yl, the amino group and hydroxyl group of which are protected; 6-amino-2-methoxypurin-9-yl; 6-amino-2-chloropurin-9-yl; 6-amino-2-fluoropurin-9-yl; 2,6-dimethoxypurin-9-yl; 2,6-dichloropurin-9-yl; 6-mercaptopurin-9-yl; 2-oxo-4-amino-pyrimidin-1-yl; 2-oxo-4-amino-pyrimidin-1-yl, the amino group of which is protected; 2-oxo-4-amino-5-fluoro-pyrimidin-1-yl; 2-oxo-4-amino-5-fluoro-pyrimidin-1-yl, the amino group of which is protected; 4-amino-2-oxo-5-chloro-pyrimidin-1-yl; 2-oxo-4-methoxy-pyrimidin-1-yl; 2-oxo-4-mercapto-pyrimidin-1-yl; 2-oxo-4-hydroxy-pyrimidin-1-yl; 2-oxo-4-hydroxy-5-methylpyrimidin-1-yl; 4-amino-5-methyl-2-oxo-pyrimidin-1-yl group and 4-amino-5-methyl-2-oxo-pyrimidin-1-yl group, the amino group of which is protected.

15. The compound according to claim 6 or a salt thereof, wherein B is selected from the group consisting of 6-aminopurin-9-yl; 6-aminopurin-9-yl, the amino group of which is protected; 2,6-diaminopurin-9-yl; 2-amino-6-chloropurin-9-yl; 2-amino-6-chloropurin-9-yl, the amino group of which is protected; 2-amino-6-fluoropurin-9-yl; 2-amino-6-fluoropurin-9-yl, the amino group of which is protected; 2-amino-6-bromopurin-9-yl; 2-amino-6-bromopurin-9-yl, the amino group of which is protected; 2-amino-6-hydroxypurin-9-yl;

2-amino-6-hydroxypurin-9-yl, the amino group of which is protected; 2-amino-6-hydroxypurin-9-yl, the amino group and hydroxyl group of which are protected; 6-amino-2-methoxypurin-9-yl; 6-amino-2-chloropurin-9-yl; 6-amino-2-fluoropurin-9-yl; 2,6-dimethoxypurin-9-yl; 2,6-dichloropurin-9-yl; 6-mercaptopurin-9-yl; 2-oxo-4-aminopyrimidin-1-yl; 2-oxo-4-amino-pyrimidin-1-yl, the amino group of which is protected; 2-oxo-4-amino-5-fluoro-pyrimidin-1-yl; 2-oxo-4-amino-5-fluoro-pyrimidin-1-yl, the amino group of which is protected; 4-amino-2-oxo-5-chloro-pyrimidin-1-yl; 2-oxo-4-methoxy-pyrimidin-1-yl; 2-oxo-4-mercapto-pyrimidin-1-yl; 2-oxo-4-hydroxy-pyrimidin-1-yl; 2-oxo-4-hydroxy-5-methylpyrimidin-1-yl; 4-amino-5-methyl-2-oxo-pyrimidin-1-yl group and 4-amino-5-methyl-2-oxo-pyrimidin-1-yl group, the amino group of which is protected.

16. The compound according to claim 7 or a salt thereof, wherein B is selected from the group consisting of 6-aminopurin-9-yl; 6-aminopurin-9-yl, the amino group of which is protected; 2,6-diaminopurin-9-yl; 2-amino-6-chloropurin-9-yl; 2-amino-6-chloropurin-9-yl, the amino group of which is protected; 2-amino-6-fluoropurin-9-yl; 2-amino-6-fluoropurin-9-yl, the amino group of which is protected; 2-amino-6-bromopurin-9-yl; 2-amino-6-bromopurin-9-yl, the amino group of which is protected; 2-amino-6-hydroxypurin-9-yl; 2-amino-6-hydroxypurin-9-yl, the amino group of which is protected; 2-amino-6-hydroxypurin-9-yl, the amino group and hydroxyl group of which are protected; 6-amino-2-methoxypurin-9-yl; 6-amino-2-chloropurin-9-yl; 6-amino-2-fluoropurin-9-yl; 2,6-dimethoxypurin-9-yl; 2,6-dichloropurin-9-yl; 6-mercaptopurin-9-yl; 2-oxo-4-aminopyrimidin-1-yl; 2-oxo-4-amino-pyrimidin-1-yl, the amino group of which is protected; 2-oxo-4-amino-5-fluoro-pyrimidin-1-yl; 2-oxo-4-amino-5-fluoro-pyrimidin-1-yl, the amino group of which is protected; 4-amino-2-oxo-5-chloro-pyrimidin-1-yl; 2-oxo-4-methoxy-pyrimidin-1-yl; 2-oxo-4-mercapto-pyrimidin-1-yl; 2-oxo-4-hydroxy-pyrimidin-1-yl; 2-oxo-4-hydroxy-5-methylpyrimidin-1-yl; 4-amino-5-methyl-2-oxo-pyrimidin-1-yl group and 4-amino-5-methyl-2-oxo-pyrimidin-1-yl group, the amino group of which is protected.

17. The compound according to claim 8 or a salt thereof, wherein B is selected from the group consisting of 6-aminopurin-9-yl; 6-aminopurin-9-yl, the amino group of which is protected; 2,6-diaminopurin-9-yl; 2-amino-6-chloropurin-9-yl; 2-amino-6-chloropurin-9-yl, the amino group of which is protected; 2-amino-6-fluoropurin-9-yl; 2-amino-6-fluoropurin-9-yl, the amino group of which is protected; 2-amino-6-bromopurin-9-yl; 2-amino-6-bromopurin-9-yl, the amino group of which is protected; 2-amino-6-hydroxypurin-9-yl; 2-amino-6-hydroxypurin-9-yl, the amino group of which is protected; 2-amino-6-hydroxypurin-9-yl, the amino group and hydroxyl group of which are protected; 6-amino-2-methoxypurin-9-yl; 6-amino-2-chloropurin-9-yl; 6-amino-2-fluoropurin-9-yl; 2,6-dimethoxypurin-9-yl; 2,6-dichloropurin-9-yl; 6-mercaptopurin-9-yl; 2-oxo-4-aminopyrimidin-1-yl; 2-oxo-4-amino-pyrimidin-1-yl, the amino group of which is protected; 2-oxo-4-amino-5-fluoro-pyrimidin-1-yl; 2-oxo-4-amino-5-fluoro-pyrimidin-1-yl, the amino group of which is protected; 4-amino-2-oxo-5-chloro-pyrimidin-1-yl; 2-oxo-4-methoxy-pyrimidin-1-yl; 2-oxo-4-mercapto-pyrimidin-1-yl; 2-oxo-4-hydroxy-pyrimidin-1-yl; 2-oxo-4-hydroxy-5-methylpyrimidin-1-yl; 4-amino-5-methyl-2-oxo-pyrimidin-1-yl group and 4-amino-5-methyl-2-oxo-pyrimidin-1-yl group, the amino group of which is protected.

18. The compound according to claim 9 or a salt thereof, wherein B is selected from the group consisting of 6-aminopurin-9-yl; 6-aminopurin-9-yl, the amino group of which is protected; 2,6-diaminopurin-9-yl; 2-amino-6-chloropurin-9-yl; 2-amino-6-chloropurin-9-yl, the amino group of which is protected; 2-amino-6-fluoropurin-9-yl; 2-amino-6-fluoropurin-9-yl, the amino group of which is protected; 2-amino-6-bromopurin-9-yl; 2-amino-6-bromopurin-9-yl, the amino group of which is protected; 2-amino-6-hydroxypurin-9-yl; 2-amino-6-hydroxypurin-9-yl, the amino group of which is protected; 2-amino-6-hydroxypurin-9-yl, the amino group and hydroxyl group of which are protected; 6-amino-2-methoxypurin-9-yl; 6-amino-2-chloropurin-9-yl; 6-amino-2-fluoropurin-9-yl; 2,6-dimethoxypurin-9-yl; 2,6-dichloropurin-9-yl; 6-mercaptopurin-9-yl; 2-oxo-4-aminopyrimidin-1-yl; 2-oxo-4-amino-pyrimidin-1-yl, the amino group of which is protected; 2-oxo-4-amino-5-fluoro-pyrimidin-1-yl; 2-oxo-4-amino-5-fluoro-pyrimidin-1-yl, the amino group of which is protected; 4-amino-2-oxo-5-chloro-pyrimidin-1-yl; 2-oxo-4-methoxy-pyrimidin-1-yl; 2-oxo-4-mercapto-pyrimidin-1-yl; 2-oxo-4-hydroxy-pyrimidin-1-yl; 2-oxo-4-hydroxy-5-methylpyrimidin-1-yl; 4-amino-5-methyl-2-oxo-pyrimidin-1-yl group and 4-amino-5-methyl-2-oxo-pyrimidin-1-yl group, the amino group of which is protected.

19. The compound according to claim 1 or a salt thereof, wherein B is selected from the group consisting of 6-benzoylaminopurin-9-yl, adeninyl, 2-isobutyrylamino-6-hydroxypurin-9-yl, guaninyl, 2-oxo-4-benzoylamino-pyrimidin-1-yl, cytosinyl, 2-oxo-5-methyl-4-benzoylaminopyrimidin-1-yl, 5-methylcytosinyl, uracinyl and thiminyl groups.

20. The compound according to claim 2 or a salt thereof, wherein B is selected from the group consisting of 6-benzoylaminopurin-9-yl, adeninyl, 2-isobutyrylamino-6-hydroxypurin-9-yl, guaninyl, 2-oxo-4-benzoylamino-pyrimidin-1-yl, cytosinyl, 2-oxo-5-methyl-4-benzoylaminopyrimidin-1-yl, 5-methylcytosinyl, uracinyl and thyminyl groups.

21. The compound according to claim 3 or a salt thereof, wherein B is selected from the group consisting of 6-benzoylaminopurin-9-yl, adeninyl, 2-isobutyrylamino-6-hydroxypurin-9-yl, guaninyl, 2-oxo-4-benzoylamino-pyrimidin-1-yl, cytosinyl, 2-oxo-5-methyl-4-benzoylaminopyrimidin-1-yl, 5-methylcytosinyl, uracinyl and thyminyl groups.

22. The compound according to claim 4 or a salt thereof, wherein B is selected from the group consisting of 6-benzoylaminopurin-9-yl, adeninyl, 2-isobutyrylamino-6-hydroxypurin-9-yl, guaninyl, 2-oxo-4-benzoylamino-pyrimidin-1-yl, cytosinyl, 2-oxo-5-methyl-4-benzoylaminopyrimidin-1-yl, 5-methylcytosinyl, uracinyl and thyminyl groups.

23. The compound according to claim 5 or a salt thereof, wherein B is selected from the group consisting of 6-benzoylaminopurin-9-yl, adeninyl, 2-isobutyrylamino-6-hydroxypurin-9-yl, guaninyl, 2-oxo-4-benzoylamino-pyrimidin-1-yl, cytosinyl, 2-oxo-5-methyl-4-benzoylaminopyrimidin-1-yl, 5-methylcytosinyl, uracinyl and thyminyl groups.

24. The compound according to claim 6 or a salt thereof, wherein B is selected from the group consisting of 6-benzoylaminopurin-9-yl, adeninyl, 2-isobutyrylamino-6-hydroxypurin-9-yl, guaninyl, 2-oxo-4-benzoylamino-pyrimidin-1-yl, cytosinyl, 2-oxo-5-methyl-4-benzoylaminopyrimidin-1-yl, 5-methylcytosinyl, uracinyl and thyminyl groups.

25. The compound according to claim 7 or a salt thereof, wherein B is selected from the group consisting of 6-benzoylaminopurin-9-yl, adeninyl, 2-isobutyrylamino-6-hydroxypurin-9-yl, guaninyl, 2-oxo-4-benzoylamino-pyrimidin-1-yl, cytosinyl, 2-oxo-5-methyl-4-benzoylamino-pyrimidin-1-yl, 5-methylcytosinyl, uracinyl and thyminyl groups.

26. The compound according to claim 8 or a salt thereof, wherein B is selected from the group consisting of 6-benzoylaminopurin-9-yl, adeninyl, 2-isobutyrylamino-6-hydroxypurin-9-yl, guaninyl, 2-oxo-4-benzoylamino-pyrimidin-1-yl, cytosinyl, 2-oxo-5-methyl-4-benzoylamino-pyrimidin-1-yl, 5-methylcytosinyl, uracinyl and thyminyl groups.

27. The compound according to claim 9 or a salt thereof, wherein B is selected from the group consisting of 6-benzoylaminopurin-9-yl, adeninyl, 2-isobutyrylamino-6-hydroxypurin-9-yl, guaninyl, 2-oxo-4-benzoylamino-pyrimidin-1-yl, cytosinyl, 2-oxo-5-methyl-4-benzoylamino-pyrimidin-1-yl, 5-methylcytosinyl, uracinyl and thyminyl groups.

28. A compound or a salt thereof selected from the group consisting of
2'-O,4'-C-ethyleneguanosine,
2'-O,4'-C-ethyleneadenosine,
3',5'-di-O-benzyl-2'-O,4'-C-ethylene-6-N-benzoyladenosine,
3',5'-di-O-benzyl-2'-O,4'-C-ethylene-2-N-isobutyrylguanosine,
5'-O-dimethoxytrityl-2'-O,4'-C-ethylene-6-N-benzoyladenosine,
5'-O-dimethoxytrityl-2'-O,4'-C-ethylene-2-N-isobutyrylguanosine,
2'-O,4'-C-ethylene-2-N-isobutyrylguanosine,
2'O,4'-C-ethylene-6-N-benzoyladenosine,
5'-O-dimethoxytrityl-2'-O,4'-C-ethylene-6-N-benzoyladenosine-3'-O-(2-cyanoethyl N,N-diisopropyl)phosphoramidite,
5'-O-dimethoxytrityl-2'-O,4'-C-ethylene-2-N-isobutyrylguanosine-3'-O-(2-cyanoethyl N,N-diisopropyl) phosphoramidite,
2'-O,4'-C-ethyleneuridine,
2'-O,4'-C-ethylene-5-methyluridine,
2'-O,4'-C-ethylenecytidine,
2'-O,4'-C-ethylene-5-methylcytidine,
3',5'-di-O-benzyl-2'-O,4'-C-ethyleneuridine,
5'-O-dimethoxytrityl-2'-O,4'-C-ethyleneuridine,
3',5'-di-O-benzyl-2'-O,4'-C-ethylene-5-methyluridine,
5'-O-dimethoxytrityl-2'-O,4'-C-ethylene-5-methyluridine,
3',5'-di-O-benzyl-2'-O,4'-C-ethylene-4-N-benzoylcytidine,
5'-O-dimethoxytrityl-2'-O,4'-C-ethylene-4-N-benzoylcytidine,
3',5'-di-O-benzyl-2'-O,4'-C-ethylene-4-N-benzoyl-5-methylcytidine,
5'-O-dimethoxytrityl-2'-O,4'-C-ethylene-4-N-benzoyl-5-methylcytidine,
2'-O,4'-C-ethylene-4-N-benzoylcytidine,
2'-O,4'-C-ethylene-4-N-benzoyl-5-methylcytidine,
5'-O-dimethoxytrityl-2'-O,4'-C-ethylene-uridine-3'-O-(2-cyanoethyl N,N-diisopropyl)phosphoramidite,
5'-O-dimethoxytrityl-2'-O,4'-C-ethylene-5-methyluridine-3'-O-(2-cyanoethyl N,N-diisopropyl)phosphoramidite,
5'-O-dimethoxytrityl-2'-O,4'-C-ethylene-4-N-benzoylcytidine-3'-O-(2-cyanoethyl N,N-diisopropyl)phosphoramidite, and
5'-O-dimethoxytrityl-2'-O,4'-C-ethylene-4-N-benzoyl-5-methylcytidine-3'-O-(2-cyanoethyl N,N-diisopropyl) phosphoramidite.

29. 5'-O-Dimethoxytrityl-2'-O,4'-C-ethylene-5-methyluridine-3'-O-(2-cyanoethyl N,N-diisopropyl)phosphoramidite or a salt thereof.

30. 5'-O-Dimethoxytrityl-2'-O,4'-C-ethylene-6-N-benzoyladenosine-3'-O-(2-cyanoethyl N,N-diisopropyl)phosphoramidite or a salt thereof.

31. 5'-O-Dimethoxytrityl-2'-O,4'-C-ethylene-2-N-isobutyrylguanosine-3'-O-(2-cyanoethyl N,N-diisopropyl)phosphoramidite or a salt thereof.

32. 5'-O-Dimethoxytrityl-2'-O,4'-C-ethylene-uridine-3'-O-(2-cyanoethyl N,N-diisopropyl)phosphoramidite or a salt thereof.

33. 5'-O-Dimethoxytrityl-2'-O,4'-C-ethylene-4-N-benzoylcytidine-3'-O-(2-cyanoethyl N,N-diisopropyl)phosphoramidite or a salt thereof.

34. 5'-O-Dimethoxytrityl-2'-O,4'-C-ethylene-4-N-benzoyl-5-methylcytidine-3'-O-(2-cyanoethyl N,N-diisopropyl) phosphoramidite or a salt thereof.

35. An oligonucleotide analogue comprising two or more nucleoside units wherein at least one of said nucleoside units is a structure of the formula (2):

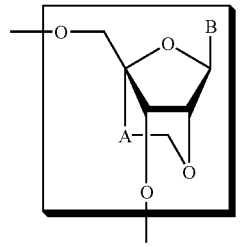

(2)

wherein:
A represents a methylene group; and
B is selected from the group consisting of an unsubstituted purin-9-yl group, an unsubstituted 2-oxo-pyrimidin-1-yl group, a purin-9-yl group substituted with at least one substituent α and a 2-oxo-pyrimidin-1-yl group substituted with at least one substituent α, said substituent α being selected from the group consisting of an unprotected hydroxyl group, a protected hydroxyl group, an alkoxy group having from 1 to 4 carbon atoms, an unprotected mercapto group, a protected mercapto group, an alkylthio group having from 1 to 4 carbon atoms, an unprotected amino group, a protected amino group, an amino group substituted by an alkyl group having from 1 to 4 carbon atoms, an alkyl group having from 1 to 4 carbon atoms and a halogen atom; or a salt thereof.

36. The oligonucleotide analogue according to claim 35 or a salt thereof, which comprises up to 100 nucleoside units and wherein nucleoside units are bonded to each other through a phosphodiester bond or a phosphorothioate bond.

37. The oligonucleotide analogue according to claim 35 or a salt thereof which comprises 2 to 50 nucleoside units; and when said oligonucleotide analogue contains two or more nucleoside units of the structure of said formula (2), said nucleoside units of the structure of formula (2) are the same or different, and wherein said salt is a pharmaceutically acceptable salt.

38. The oligonucleotide analogue according to claim 37 or a salt thereof which comprises 10 to 30 nucleoside units.

39. The oligonucleotide analogue according to claim 35 or a salt thereof, wherein said nucleoside units are bonded to each other through a phosphoric acid diester bond or a phosphorothioate bond.

40. The oligonucleotide analogue according to claim 35 or a salt thereof, wherein B is selected from the group consisting of 6-aminopurin-9-yl; 6-aminopurin-9-yl, the amino group of which is protected; 2,6-diamino-purin-9-yl; 2-amino-6-chloropurin-9-yl, 2-amino-6-chloropurin-9-yl, the amino group of which is protected; 2-amino-6-fluoropurin-9-yl; 2amino-6-fluoropurin-9-yl, the amino group of which is protected; 2-amino-6-bromopurin-9-yl; 2-amino-6-bromopurin-9-yl, the amino group of which is protected; 2-amino-6-hydroxypurin-9-yl; 2-amino-6-hydroxypurin-9-yl, the amino group of which is protected; 2-amino-6-hydroxypurin-9-yl, the amino group and hydroxyl group of which are protected; 6-amino-2-methoxypurin-9-yl; 6-amino-2-chloropurin-9-yl; 6-amino-2-fluoropurin-9-yl; 2,6-dimethoxypurin-9-yl; 2,6-dichloro-purin-9-yl; 6-mercaptopurin-9-yl; 2-oxo-4-amino-pyrimidin-1-yl; 2-oxo-4-amino-pyrimidin-1-yl, the amino group of which is protected; 2-oxo-4-amino-5-fluoro-pyrimidin-1-yl; 2-oxo-4-amino-5-fluoro-pyrimidin-1-yl, the amino group of which is protected; 4-amino-2-oxo-5-chloro-pyrimidin-1-yl; 2-oxo-4-methoxy-pyrimidin-1-yl; 2-oxo-4-mercapto-pyrimidin-1-yl; 2-oxo-4-hydroxy-pyrimidin-1-yl; 2-oxo-4-hydroxy-5-methylpyrimidin-1-yl; 4-amino-5-methyl-2-oxo-pyrimidin-1-yl group and 4-amino-5-methyl-2-oxo-pyrimidin-1-yl group, the amino group of which is protected.

41. The oligonucleotide analogue according to claim 35 or a salt thereof, wherein B is selected from the group consisting of 6-benzoylaminopurin-9-yl, adeninyl, 2-isobutyrylamino-6-hydroxypurin-9-yl, guaninyl, 2-oxo-4-benzoylamino-pyrimidin-1-yl, cytosinyl, 2-oxo-5-methyl-4-benzoylamino-pyrimidin-1yl, 5-methylcytosinyl, uracinyl and thyminyl groups.

42. A pharmaceutical composition comprising a pharmaceutically effective amount of a pharmacologically active compound together with a carrier therefor, wherein said pharmacologically active compound is an oligonucleotide analogue comprising two or more nucleoside units, wherein at least one of said nucleoside units is a structure of the formula (2):

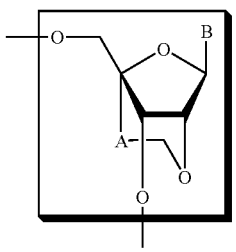

(2)

wherein:
A represents a methylene group; and
B is selected from the group consisting of an unsubstituted purin-9-yl group, an unsubstituted 2-oxo-pyrimidin-1-yl group, a purin-9-yl group substituted with at least one substituent α and a 2-oxo-pyrimidin-1-yl group substituted with at least one substituent α, said substituent α being selected from the group consisting of an unprotected hydroxyl group, a protected hydroxyl group, an alkoxy group having from 1 to 4 carbon atoms, an unprotected mercapto group, a protected mercapto group, an alkylthio group having from 1 to 4 carbon atoms, an unprotected amino group, a protected amino group, an amino group substituted by an alkyl group having from 1 to 4 carbon atoms, an alkyl group having from 1 to 4 carbon atoms and a halogen atom; or a pharmacologically acceptable salt thereof.

43. A pharmaceutical composition according to claim 42, wherein B is selected from the group consisting of 6-aminopurin-9-yl; 6-aminopurin-9-yl, the amino group of which is protected; 2,6-diamino-purin-9-yl; 2-amino-6-chloropurin-9-yl; 2-amino-6-chloropurin-9-yl, the amino group of which is protected; 2-amino-6-fluoropurin-9-yl; 2-amino-6-fluoropurin-9-yl, the amino group of which is protected; 2-amino-6-bromopurin-9-yl; 2-amino-6-bromopurin-9-yl, the amino group of which is protected; 2-amino-6-hydroxypurin-9-yl; 2-amino-6-hydroxypurin-9-yl, the amino group of which is protected; 2-amino-6-hydroxypurin-9-yl, the amino group and hydroxyl group of which are protected; 6-amino-2-methoxypurin-9-yl; 6-amino-2-chloropurin-9-yl; 6-amino-2-fluoropurin-9-yl; 2,6-dimethoxypurin-9-yl; 2,6-dichloro-purin-9-yl; 6-mercaptopurin-9-yl; 2-oxo-4-amino-pyrimidin-1-yl; 2-oxo-4-amino-pyrimidin-1-yl, the amino group of which is protected; 2-oxo-4-amino-5-fluoro-pyrimidin-1-yl; 2-oxo-4-amino-5-fluoro-pyrimidin-1-yl, the amino group of which is protected; 4-amino-2-oxo-5-chloro-pyrimidin-1-yl; 2-oxo-4-methoxy-pyrimidin-1-yl; 2-oxo-4-mercapto-pyrimidin-1-yl; 2-oxo-4-hydroxy-pyrimidin-1-yl; 2-oxo-4-hydroxy-5-methylpyrimidin-1-yl; 4-amino-5-methyl-2-oxo-pyrimidin-1-yl group and 4-amino-5-methyl-2-oxo-pyrimidin-1-yl group, the amino group of which is protected.

44. A pharmaceutical composition according to claim 42, wherein B is selected from the group consisting of 6-benzoylaminopurin-9-yl, adeninyl, 2-isobutyrylamino-6-hydroxypurin-9-yl, guaninyl, 2-oxo-4-benzoylamino-pyrimidin-1-yl, cytosinyl, 2-oxo-5-methyl-4-benzoylamino-pyrimidin1-yl, 5-methylcytosinyl, uracinyl and thyminyl groups.

45. 5'-O-Dimethoxytrityl-2'-O,4'-C-ethylene-6-N-benzoyladenosine or a salt thereof.

46. 5'-O-Dimethoxytrityl-2'-O,4'-C-ethylene-2-N-isobutyrylguanosine or a salt thereof.

47. 5'-O-Dimethoxytrityl-2'-O,4'-C-ethyleneuridine or a salt thereof.

48. 5'-O-Dimethoxytrityl-2'-O,4'-C-ethylene-5-methyluridine or a salt thereof.

49. 5'-O-Dimethoxytrityl-2'-O,4'-C-ethylene-4-N-benzoylcytidine or a salt thereof.

50. 5'-O-Dimethoxytrityl-2'-O,4'-C-ethylene-4-N-benzoyl-5-methylcytidine or a salt thereof.

51. The oligonucleotide analogue according to claim 35 or a salt thereof, wherein B is a 6-an adeninyl group.

52. The oligonucleotide analogue according to claim 35 or a salt thereof, wherein B is a 2-guaninyl group.

53. The oligonucleotide analogue according to claim 35 or a salt thereof, wherein B is a uracinyl group.

54. The oligonucleotide analogue according to claim 35 or a salt thereof, wherein B is a 2-oxo-4-hydroxy-5-methylpyrimidin-1-yl group.

55. The oligonucleotide analogue according to claim 35 or a salt thereof, wherein B is a 2-oxo-4-cytosinyl group.

56. The oligonucleotide analogue according to claim 35 or a salt thereof, wherein B is a 5-methylcytosinyl group.

57. The compound according to claim 2 or a salt thereof, wherein $R^1$ is selected from the group consisting of benzyl, 4-methylbenzyl, 2,4,6-trimethylbenzyl, 3,4,5-trimethylbenzyl and 4-methoxybenzyl.

58. The compound according to claim 4 or a salt thereof, wherein $R^2$ is selected from the group consisting of benzyl, 4-methylbenzyl, 2,4,6-trimethylbenzyl, 3,4,5-trimethylbenzyl and 4-methoxybenzyl.

59. The compound according to claim 5 or a salt thereof, wherein $R^2$ is selected from the group consisting of benzyl, 4-methylbenzyl, 2,4,6-trimethylbenzyl, 3,4,5-trimethylbenzyl and 4 methoxybenzyl.

60. The compound according to claim 6 or a salt thereof, wherein $R^2$ is selected from the group consisting of benzyl, 4-methylbenzyl, 2,4,6-trimethylbenzyl, 3,4,5-trimethylbenzyl and 4-methoxybenzyl.

* * * * *

SEQUENCE LISTING

<160> NUMBER OF SEQ ID NOS: 3

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthesized
      oligonucleotide for testing Tm value

<400> SEQUENCE: 1
agcaaaaaac gc                                                        12

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthesized
      oligonucleotide for testing Tm value

<400> SEQUENCE: 2
gcgttttttg ct                                                        12

<210> SEQ ID NO 3

```
-continued
<211> LENGTH: 23
<212> TYPE: DNA
<213> ORGANISM: Artificial Sequence
<220> FEATURE:
<223> OTHER INFORMATION: Description of Artificial Sequence: Synthesized
      oligonucleotide

<400> SEQUENCE: 3
tcctctgtgc ttggttctgg cct                                           23
```